US008821863B2

(12) United States Patent
Kumar et al.

(10) Patent No.: US 8,821,863 B2
(45) Date of Patent: Sep. 2, 2014

(54) HUMANIZED ANTI-α 9 INTEGRIN ANTIBODIES AND THE USES THEREOF

(75) Inventors: Shankar Kumar, Pleasanton, CA (US); J. Yun Tso, Menlo Park, CA (US); Naoya Tsurushita, Palo Alto, CA (US); Shigeyuki Kon, Sapporo (JP)

(73) Assignees: Gene Techno Science Co., Ltd., Hokkaido (JP); Kaken Pharmaceutical Co., Tokyo (JP)

( * ) Notice: Subject to any disclaimer, the term of this patent is extended or adjusted under 35 U.S.C. 154(b) by 0 days.

(21) Appl. No.: 12/812,455

(22) PCT Filed: Jan. 13, 2009

(86) PCT No.: PCT/JP2009/050606
§ 371 (c)(1),
(2), (4) Date: Aug. 31, 2010

(87) PCT Pub. No.: WO2009/088105
PCT Pub. Date: Jul. 16, 2009

(65) Prior Publication Data
US 2010/0329980 A1 Dec. 30, 2010

Related U.S. Application Data

(60) Provisional application No. 61/020,527, filed on Jan. 11, 2008.

(51) Int. Cl.
*A61K 39/42* (2006.01)
*C07K 16/00* (2006.01)
*C07K 16/28* (2006.01)

(52) U.S. Cl.
USPC .............. 424/130.1; 424/143.1; 530/387.1; 530/388.22

(58) Field of Classification Search
None
See application file for complete search history.

(56) References Cited

U.S. PATENT DOCUMENTS

| | | | |
|---|---|---|---|
| 5,859,205 A * | 1/1999 | Adair et al. | 530/387.3 |
| 7,595,045 B2 | 9/2009 | Kurotaki et al. | |
| 2004/0234524 A1 | 11/2004 | Uede et al. | |
| 2008/0069815 A1 | 3/2008 | Uede et al. | |
| 2008/0152653 A1 | 6/2008 | Kurotaki et al. | |
| 2008/0292619 A1* | 11/2008 | Sehara et al. | 424/133.1 |
| 2009/0252734 A1 | 10/2009 | Kanayama et al. | |

FOREIGN PATENT DOCUMENTS

| | | |
|---|---|---|
| CN | 101103044 A | 1/2008 |
| EP | 1840135 A1 | 10/2007 |
| WO | WO-90/07861 | 7/1990 |
| WO | WO-91/09968 | 7/1991 |
| WO | WO 92/03918 | 3/1992 |
| WO | WO-02/081522 | 10/2002 |
| WO | WO 03/105782 | 12/2003 |
| WO | WO 2005/061540 | 7/2005 |
| WO | WO-2006/075784 | 7/2006 |
| WO | WO-2008/007804 | 1/2008 |

OTHER PUBLICATIONS

Amit et al. Three-dimensional structure of an antigen-antibody complex at 2.8 A resolution. Science vol. 233 747-753 1986.*
Eduardo Padlan, Anatomy of the antibody molecule. Mol Immunol. Feb. 1994;31(3):169-217.*
Vajdos et al. Comprehensive functional maps of the antigen-binding site of an anti-ErbB2 antibody obtained with shotgun scanning mutagenesis. J. Mol. Biol. Jul. 5, 2002, 320(2):415-28.*
Brown et al. Tolerance of single, but not multiple, amino acid replacements in antibody VH CDR 2: a means of minimizing B cell wastage from somatic hypermutation? J. Immuno. May 1996, 3285-91.*
Hynes, Cell (2002) 110:673-687.
Miyasaka, (2000) New edition of Adhesion Molecule Handbook, Shujunsya, pp. 24-65.
Palmer et al., J. Cell Biol. (1993) 123:1289-1297.
Yokosaki et al., J. Biol. Chem. (1999) 274:36328-36334.
Green et al., FEBS Letters (2001) 503:75-79.
Barry et al., Exp. Cell Res. (2000) 258:342-351.
Staniszewska et al., J. Cell Science (2008) 121:504-513.
Vlahakis et al., J. Biol. Chem. (2007) 282:15187-15196.
Eto et al., J. Biol. Chem. (2000) 275:34922-34930.
Eto et al., J. Biol. Chem. (2002) 277:17804-17810.
Schreiber et al., Haematologica 2009 (2009) doi:10.3324/haematol. 2009.006072.
De Hart et al., PNAS USA (2008) 105:7188-7193.
Staniszewska et al., Circ. Res. (2007) 100:1308-1316.
Singh et al., J. Invest. Dermatology (2008) doi:10.1038/jid.2008.201.
Silletti et al., J. Biol. Chem. (2000) 149:1485-1501.
Majundar et al., J. Biol. Chem. (2004) 279:37528-37534.
Yokosaki et al., J. Biol. Chem. (1998) 273:11423-11428.
Mishima et al., Molecular Biology of the Cell (2007) 18:1421-1429.
Silverman et al., Arthritis & Rheumatism (2007) 56:1817-1826.
Sun et al., Am. J. Physiol. Lung Cell Mol. Physiol. (2010) doi:10. 1152/ajplung.00039.2010.

(Continued)

*Primary Examiner* — Maher Haddad
(74) *Attorney, Agent, or Firm* — Morrison & Foerster, LLP

(57) ABSTRACT

The present invention provides humanized antibodies that immunospecifically recognize human α9 integrin. Some of these antibodies inhibit the biological functions of the α9 integrin, thereby exhibiting therapeutic effects on various disorders or diseases that are associated with α9 integrin, including cancer, e.g., the growth and metastasis of a cancer cell, and inflammatory diseases, e.g., rheumatoid arthritis, osteoarthritis, hepatitis, bronchial asthma, fibrosis, diabetes, arteriosclerosis, multiple sclerosis, granuloma, an inflammatory bowel disease (ulcerative colitis and Crohn's disease), an autoimmune disease, and so forth.

2 Claims, 24 Drawing Sheets

(56) References Cited

OTHER PUBLICATIONS

Nakayama, Laboratory Investigation (2010) doi:10.1038/labinvest.2010.69.
GenBank Public DNA Database, Accession No. NM_002207, Sep. 26, 2010.
GenBank Public DNA Database, Accession No. NM_133721, Aug. 4, 2010.
GenBank Public DNA Database, Accession No. NM_000885, Sep. 19, 2010.
GenBank Public DNA Database, Accession No. NM_010576, Sep. 12, 2010.
GenBank Public DNA Database, Accession No. X07979, Oct. 7, 2008.
GenBank Public DNA Database, Accession No. NM_010578, Sep. 26, 2010.
Office Action for Chinese Patent Application No. 200980102026.4, mailed Oct. 26, 2011, 15 pages (including English translation).
European Search Report for European Patent Application No. 11174722.6-2406, mailed Sep. 30, 2011, 11 pages.
Almagro et al., Frontiers in Bioscience: A Journal and Virtual Library (2008) 13(1):1619-1633.
Queen et al., Proceedings of the National Academy of Sciences of the USA (1989) 86(24):10029-10033.
Weiner, Louis M., Journal of Immunotherapy (2006) 29(1):1-9.
Supplementary European Search Report for European Application No. 09700470, dated Jan. 4, 2011, 14 pages.
The Third Office Action (including translation) for CN 200980102026.4, mailed Feb. 17, 2013.
European Search Report for EP 11174722.6, mailed Mar. 5, 2012, 14 pages.
Winter et al., "Humanized antibodies," Immunology Today (1993) 14(6):243-246.
European Search Report for European Application No. 11174722.6, dated Apr. 16, 2014, 7 pages.

\* cited by examiner

Fig. 1

```
ATGAAATGCAGCTGGGTTATCTTCTTCCTGATGGCAGTGGTTACAGGGGTCAATTCAGAG
 M  K  C  S  W  V  I  F  F  L  M  A  V  V  T  G  V  N  S  E

GTTCAGCTGCAGCAGTCTGGGGCAGAGCTTGTGAAGCCAGGGGCCTCAGTCAAGTTGTCC
 V  Q  L  Q  Q  S  G  A  E  L  V  K  P  G  A  S  V  K  L  S

TGCACAGCTTCTGGCTTCAACATTAAAGACACCTATGTGCACTGGGTGAAGCAGAGGCCT
 C  T  A  S  G  F  N  I  K  D  T  Y  V  H  W  V  K  Q  R  P

GAACAGGGCCTGGAGTGGATTGGAAATATTGATCCTGCGAATGGTAATACTAAATATGAC
 E  Q  G  L  E  W  I  G  N  I  D  P  A  N  G  N  T  K  Y  D

CCGAAGTTCCAGGGCAAGGCCACTATAACAGCAGACACATCCTCCAACACAGCCTACCTG
 P  K  F  Q  G  K  A  T  I  T  A  D  T  S  S  N  T  A  Y  L

CACCTCAGCAGCCTGACATCTGAGGACACTGCCGTCTATTACTGTGCTAGATGGTTACGA
 H  L  S  S  L  T  S  E  D  T  A  V  Y  Y  C  A  R  W  L  R

CATTTTTACTATGCTATGGACTACTGGGGTCAAGGAACCTCAGTCACCGTCTCCTCA
 H  F  Y  Y  A  M  D  Y  W  G  Q  G  T  S  V  T  V  S  S
```

Fig. 2

```
ATGAGTGTGCCCACTCAACTCCTGGGGTTGCTGCTGCTGTGGCTTACAGACGCAGGATGT
 M  S  V  P  T  Q  L  L  G  L  L  L  W  L  T  D  A  G  C

GACATCCAGATGACTCAGTCTCCAGCCTCCCTGGCTGCATCTGTGGGAGAAACTGTCACC
 D  I  Q  M  T  Q  S  P  A  S  L  A  A  S  V  G  E  T  V  T

ATCACATGTCGAGCAAGTGAGAACATTTACTACAGTTTAGCATGGTATCAGCAGAAGCAA
 I  T  C  R  A  S  E  N  I  Y  Y  S  L  A  W  Y  Q  Q  K  Q

GGGAAATCTCCTCAGCTCCTGATCTATAATGCAAACAGCTTGGAAGATGGTGTCCCATCG
 G  K  S  P  Q  L  L  I  Y  N  A  N  S  L  E  D  G  V  P  S

AGGTTCAGTGGCAGTGGATCTGGGACACAGTATTCTATGAAGATCAACAGCATGCAGCCT
 R  F  S  G  S  G  S  G  T  Q  Y  S  M  K  I  N  S  M  Q  P

GAAGATACCGCAACTTATTTCTGTAAACAGGCTTATGACGTTCCGTACACGTTCGGAGGG
 E  D  T  A  T  Y  F  C  K  Q  A  Y  D  V  P  Y  T  F  G  G

GGGACCAAGCTGGAAATAAAA
 G  T  K  L  E  I  K
```

Fig. 3

```
SpeI
ACTAGTACCACCATGAAATGCAGCTGGGTTATCTTCTTCCTGATGGCAGTGGTTACAGGG
         M  K  C  S  W  V  I  F  F  L  M  A  V  V  T  G

GTCAATTCAGAGGTTCAGCTGCAGCAGTCTGGGGCAGAGCTTGTGAAGCCAGGGGCCTCA
 V  N  S  E  V  Q  L  Q  Q  S  G  A  E  L  V  K  P  G  A  S

GTCAAGTTGTCCTGCACAGCTTCTGGCTTCAACATTAAAGACACCTATGTGCACTGGGTG
 V  K  L  S  C  T  A  S  G  F  N  I  K  D  T  Y  V  H  W  V

AAGCAGAGGCCTGAACAGGGCCTGGAGTGGATTGGAAATATTGATCCTGCGAATGGTAAT
 K  Q  R  P  E  Q  G  L  E  W  I  G  N  I  D  P  A  N  G  N

ACTAAATATGACCCGAAGTTCCAGGGCAAGGCCACTATAACAGCAGACACATCCTCCAAC
 T  K  Y  D  P  K  F  Q  G  K  A  T  I  T  A  D  T  S  S  N

ACAGCCTACCTGCACCTCAGCAGCCTGACATCTGAGGACACTGCCGTCTATTACTGTGCT
 T  A  Y  L  H  L  S  S  L  T  S  E  D  T  A  V  Y  Y  C  A

AGATGGTTACGACATTTTTACTATGCTATGGACTACTGGGGTCAAGGAACCTCAGTCACC
 R  W  L  R  H  F  Y  Y  A  M  D  Y  W  G  Q  G  T  S  V  T

HindIII
GTCTCCTCAGGTAAGAATGGCCTCTAAGCTT
 V  S  S
```

Fig. 4

```
NheI
GCTAGCACCACCATGAGTGTGCCCACTCAACTCCTGGGGTTGCTGCTGCTGTGGCTTACA
         M   S   V   P   T   Q   L   L   G   L   L   L   L   W   L   T

GACGCAGGATGTGACATCCAGATGACTCAGTCTCCAGCCTCCCTGGCTGCATCTGTGGGA
 D   A   G   C   D   I   Q   M   T   Q   S   P   A   S   L   A   A   S   V   G
             ‾

GAAACTGTCACCATCACATGTCGAGCAAGTGAGAACATTTACTACAGTTTAGCATGGTAT
 E   T   V   T   I   T   C   R   A   S   E   N   I   Y   Y   S   L   A   W   Y
                             ‾‾‾‾‾‾‾‾‾‾‾‾‾‾‾‾‾‾‾‾‾‾‾‾‾‾‾‾‾‾‾‾‾‾‾‾‾‾‾

CAGCAGAAGCAAGGGAAATCTCCTCAGCTCCTGATCTATAATGCAAACAGCTTGGAAGAT
 Q   Q   K   Q   G   K   S   P   Q   L   L   I   Y   N   A   N   S   L   E   D
                                                     ‾‾‾‾‾‾‾‾‾‾‾‾‾‾‾‾‾‾‾‾‾‾‾

GGTGTCCCATCGAGGTTCAGTGGCAGTGGATCTGGGACACAGTATTCTATGAAGATCAAC
 G   V   P   S   R   F   S   G   S   G   S   G   T   Q   Y   S   M   K   I   N

AGCATGCAGCCTGAAGATACCGCAACTTATTTCTGTAAACAGGCTTATGACGTTCCGTAC
 S   M   Q   P   E   D   T   A   T   Y   F   C   K   Q   A   Y   D   V   P   Y
                                             ‾‾‾‾‾‾‾‾‾‾‾‾‾‾‾‾‾‾‾‾‾‾‾‾‾‾‾‾‾
                                                                 EcoRI
ACGTTCGGAGGGGGGACCAAGCTGGAAATAAAACGTAAGTAGTCTTCTCAGAATTC
 T   F   G   G   G   T   K   L   E   I   K
‾
```

Fig. 6

```
                      1          2          3
            123456789 0123456789 0123456789 0123456789
24I11 VH    EVQLQQSGA ELVKPGASVK LSCTASGFNI KDTYVHWVKQ
Hu24I11 VH  QVQLVQSGA EVKKPGASVK VSCKASGFNI KDTYVHWVRQ
X65891      QVQLVQSGA EVKKPGASVK VSCKASGYTF T-----WVRQ 4          5           6          7
            0123456789 01223456789 0123456789 0123456789
                           a
24I11 VH    RPEQGLEWIG NIDPANGNTKY DPKFQGKATI TADTSSNTAY
Hu24I11 VH  APGQRLEWIG NIDPANGNTKY DPKFQGKATI TADTSASTAY
X65891      APGQRLEWMG ---------- ------RVTI TRDTSASTAY 1           1
            8            9            0           1
            0122223456789 0123456789 0000123456789 0123
              abc
24I11 VH    LHLSSLTSEDTAV YYCARWLRHF YYAMDYWGQGTSV TVSS
Hu24I11 VH  MELSSLRSEDTAV YYCARWLRHF YYAMDYWGQGTLV TVSS
X65891      MELSSLRSEDTAV YYCAR----- ------WGQGTLV TVSS
```

Fig. 7

```
                    1          2          3
          123456789 0123456789 0123456789 0123456789
24I11 VL  DIQMTQSPA SLAASVGETV TITCRASENI YYSLAWYQQK
Hu24I11 VL DIQMTQSPS SLSASVGDRV TITCRASENI YYSLAWYQQK
X72441    DIQMTQSPS SLSASVGDRV TITC------ -----WYQQK 4          5          6          7
          0123456789 0123456789 0123456789 0123456789
24I11 VL  QGKSPQLLIY NANSLEDGVP SRFSGSGSGT QYSMKINSMQ
Hu24I11 VL PGKAPKLLIY NANSLEDGVP SRFSGSGSGT QYTLTISSLQ
X72441    PGKAPKLLIY -------GVP SRFSGSGSGT DFTLTISSLQ 1
          8          9          0
          0123456789 0123456789 01234567
24I11 VL  PEDTATYFCK QAYDVPYTFG GGTKLEIK
Hu24I11 VL PEDFATYYCK QAYDVPYTFG QGTKVEIK
X72441    PEDFATYYC- --------FG QGTKVEIK
```

Fig. 8

| OLIGO-NUCLEO-TIDES | SEQUENCE | SEQ ID NO. |
|---|---|---|
| JNJ120 | GGGACTAGTACCACCATGAAATGCAGC | 101 |
| JNJ137 | GGGACTAGTACCACCATGAAATGCAGCTGGGTTATCTTCTTCCTGATGGCAGTGGTT | 102 |
| JNJ138 | AGACTGCACCAGCTGAACCTGTGAATTGACCCCTGTAACCACTGCCATCAGGAAGAA | 103 |
| JNJ139 | CAGGTTCAGCTGGTGCAGTCTGGGGCAGAGGTGAAGAAGCCAGGGGCCTCAGTCAAG | 104 |
| JNJ140 | GTCTTTAATGTTGAAGCCAGAAGCCTTGCAGGAAACCTTGACTGAGGCCCCTGGCTT | 105 |
| JNJ141 | TCTGGCTTCAACATTAAAGACACCTATGTGCACTGGGTGCGCCAGGCCCCTGGACAGAGG | 106 |
| JNJ142 | ACCATTCGCAGGATCAATATTTCCAATCCACTCCAGCCTCTGTCCAGGGGCCTGGCG | 107 |
| JNJ143 | AATATTGATCCTGCGAATGGTAATACTAAATATGACCCGAAGTTCCAGGGCAAGGCCACT | 108 |
| JNJ144 | CATGTAGGCTGTGCTCGCGGATGTGTCTGCTGTTATAGTGGCCTTGCCCTGGAACTT | 109 |
| JNJ145 | TCCGCGAGCACAGCCTACATGGAGCTCAGCAGCCTGAGATCTGAGGACACTGCCGTC | 110 |
| JNJ146 | ATAGTAAAAATGTCGTAACCATCTAGCACAGTAATAGACGGCAGTGTCCTCAGA | 111 |
| JNJ147 | TGGTTACGACATTTTTACTATGCTATGGACTACTGGGGTCAAGGAACCCTGGTCACC | 112 |
| JNJ148 | GGGAAGCTTTTGTGAGGACTCACCTGAGGAGACGGTGACCAGGGTTCCTTGACC | 113 |
| JNJ149 | GGGAAGCTTTTGTGAGGACTC | 114 |

Fig. 9

| OLIGO-NUCLEO-TIDES | SEQUENCE | SEQ ID NO. |
|---|---|---|
| JNJ150 | GGGGCTAGCACCACCATGAGT | 115 |
| JNJ126 | GGGGCTAGCACCACCATGAGTGTGCCCACTCAACTCCTGGGGTTGCTGCTGCTGTGG | 116 |
| JNJ127 | AGACTGAGTCATCTGGATGTCACATCGTGCGTCTGTAAGCCACAGCAGCAGCAACCCCAG | 117 |
| JNJ128 | GACATCCAGATGACTCAGTCTCCATCCTCCCTGTCTGCATCTGTGGGAGACAGA | 118 |
| JNJ129 | GTAAATGTTCTCACTTGCTCGACATGTGATGGTGACTCTGTCTCCCACAGATGCAGA | 119 |
| JNJ130 | CGAGCAAGTGAGAACATTTACTACAGTTTAGCATGGTATCAGCAGAAGCCAGGGAAA | 120 |
| JNJ131 | CAAGCTGTTTGCATTATAGATCAGGAGCTTAGGGGCTTTCCCTGGCTTCTGCTGATA | 121 |
| JNJ132 | ATCTATAATGCAAACAGCTTGGAAGATGGTGTCCCATCGAGGTTCAGTGGCAGTGGA | 122 |
| JNJ133 | CAGGCTGCTGATGGTGAGAGTATACTGTGTCCCAGATCCACTGCCACTGAACCTCGA | 123 |
| JNJ134 | ACTCTCACCATCAGCAGCCTGCAGCCTGAAGATTTTGCAACTTATTACTGTAAACAG | 124 |
| JNJ135 | GGTCCCTTGTCCGAACGTGTACGGAACGTCATAAGCCTGTTTACAGTAATAAGTTGC | 125 |
| JNJ136 | TACACGTTCGGACAAGGGACCAAGGTGGAAATCAAACGTGAGTAG | 126 |
| JNJ101 | GGGGAATTCTTTAAATTCTACTCACGTTTGATTTCCA | 127 |
| JNJ117 | GGGGAATTCTTTAAATTCTA | 128 |

Fig. 10

```
       SpeI
  1  GGGACTAGTACCACC ATG AAA TGC AGC TGG GTT ATC TTC TTC CTG ATG GCA GTG GTT ACA GGG
                  1▶ M   K   C   S   W   V   I   F   F   L   M   A   V   V   T   G
       ─────────────────────────────▶          ◀─────────────────────────
                                              JNJ137
       ─────────────▶
            JNJ120

64  GTC AAT TCA CAG GTT CAG CTG GTG CAG TCT GGG GCA GAG GTG AAG AAG CCA GGG GCC TCA
 17▶ V   N   S   Q   V   Q   L   V   Q   S   G   A   E   V   K   K   P   G   A   S
     ──────────────────────────────────────────────                    ◀────────────
                                               JNJ139
     ────────────
        JNJ138

124  GTC AAG GTT TCC TGC AAG GCT TCT GGC TTC AAC ATT AAA GAC ACC TAT GTG CAC TGG GTG
 37▶ V   K   V   S   C   K   A   S   G   F   N   I   K   D   T   Y   V   H   W   V
     ────────▶       ──────────────────────────────────────────────────
                                                                              JNJ141
     ──────────────────────────
              JNJ140

184  CGC CAG GCC CCT GGA CAG AGG CTG GAG TGG ATT GGA AAT ATT GAT CCT GCG AAT GGT AAT
 57▶ R   Q   A   P   G   Q   R   L   E   W   I   G   N   I   D   P   A   N   G   N
     ─────────────────────────▶                ───────────────────────────────────
     ◀───────────────────────────────────────
                     JNJ142

244  ACT AAA TAT GAC CCG AAG TTC CAG GGC AAG GCC ACT ATA ACA GCA GAC ACA TCC GCG AGC
 77▶ T   K   Y   D   P   K   F   Q   G   K   A   T   I   T   A   D   T   S   A   S
     ──────────────────────▶
          JNJ143              ◀──────────────────────
                                                         JNJ144

BglII
304  ACA GCC TAC ATG GAG CTC AGC AGC CTG AGA TCT GAG GAC ACT GCC GTC TAT TAC TGT GCT
 97▶ T   A   Y   M   E   L   S   S   L   R   S   E   D   T   A   V   Y   Y   C   A
     ──────────────────▶
                JNJ145              ◀──────────────────
                                                                         JNJ146

364  AGA TGG TTA CGA CAT TTT TAC TAT GCT ATG GAC TAC TGG GGT CAA GGA ACC CTG GTC ACC
117▶ R   W   L   R   H   F   Y   Y   A   M   D   Y   W   G   Q   G   T   L   V   T
     ────────────────────────────────────────▶
                          JNJ147                          ◀────────────────

HindIII
424  GTC TCC TCA GGTGAGTCCTCACAAAAGCTTCCC
137▶ V   S   S   ◀──────────────
                     JNJ149
     ──────────────────────────────
         JNJ148
```

Fig. 11

```
       NheI
       GGGGCTAGCACCACC ATG AGT GTG CCC ACT CAA CTC CTG GGG TTG CTG CTG CTG TGG CTT ACA
                       ► M   S   V   P   T   Q   L   L   G   L   L   L   L   W   L   T
                       ────────────────────────────────────────────────────────────►
       ──────────────────────►         ◄─────────────────────
                JNJ150              JNJ126

GAC GCA CGA TGT GAC ATC CAG ATG ACT CAG TCT CCA TCC TCC CTG TCT GCA TCT GTG GGA
     ► D   A   R   C   D   I   Q   M   T   Q   S   P   S   S   L   S   A   S   V   G
                       ──────────────────────────────────────────► 
                                                              JNJ128  ◄─────────
       ─────────────────────►
              JNJ127

GAC AGA GTC ACC ATC ACA TGT CGA GCA AGT GAG AAC ATT TAC TAC AGT TTA GCA TGG TAT
     ► D   R   V   T   I   T   C   R   A   S   E   N   I   Y   Y   S   L   A   W   Y
       ────────────►     ───────────────────────────────────────────────────────────
                                                                         JNJ130   ◄
       ──────────────────────────────────────►
                     JNJ129

CAG CAG AAG CCA GGG AAA GCC CCT AAG CTC CTG ATC TAT AAT GCA AAC AGC TTG GAA GAT
     ► Q   Q   K   P   G   K   A   P   K   L   L   I   Y   N   A   N   S   L   E   D
       ──────────────────────►          ─────────────────────────────────────────────
       ─────────────────────────────────────────────────────►
                              JNJ131

GGT GTC CCA TCG AGG TTC AGT GGC AGT GGA TCT GGG ACA CAG TAT ACT CTC ACC ATC AGC
     ► G   V   P   S   R   F   S   G   S   G   S   G   T   Q   Y   T   L   T   I   S
       ──────────    ────────────────────────────────────────   ──────────────────────
         JNJ132  ◄───────────
                              ──────────────────────────►
                                        JNJ133

PstI
       AGC CTG CAG CCT GAA GAT TTT GCA ACT TAT TAC TGT AAA CAG GCT TAT GAC GTT CCG TAC
     ► S   L   Q   P   E   D   F   A   T   Y   Y   C   K   Q   A   Y   D   V   P   Y
       ────────────────────────────────────────────────────►
       ────────────  ◄─────────────────────
              JNJ134                                ─────────────────────────
                                                             JNJ135

EcoRI
       ACG TTC GGA CAA GGG ACC AAG GTG GAA ATC AAA CGTGAGTAGAATTTAAAGAATTCCCC
     ► T   F   G   Q   G   T   K   V   E   I   K                   ◄──────────
                                                                      JNJ117
       ─────────────────────────────────────────►
                       JNJ136 ◄
                                   JNJ101
```

Fig. 12

```
SpeI
ACTAGTACCACCATGAAATGCAGCTGGGTTATCTTCTTCCTGATGGCAGTGGTTACAGGG
         M  K  C  S  W  V  I  F  F  L  M  A  V  V  T  G

GTCAATTCACAGGTTCAGCTGGTGCAGTCTGGGGCAGAGGTGAAGAAGCCAGGGGCCTCA
 V  N  S  Q  V  Q  L  V  Q  S  G  A  E  V  K  K  P  G  A  S

GTCAAGGTTTCCTGCAAGGCTTCTGGCTTCAACATTAAAGACACCTATGTGCACTGGGTG
 V  K  V  S  C  K  A  S  G  F  N  I  K  D  T  Y  V  H  W  V

CGCCAGGCCCCTGGACAGAGGCTGGAGTGGATTGGAAATATTGATCCTGCGAATGGTAAT
 R  Q  A  P  G  Q  R  L  E  W  I  G  N  I  D  P  A  N  G  N

ACTAAATATGACCCGAAGTTCCAGGGCAAGGCCACTATAACAGCAGACACATCCGCGAGC
 T  K  Y  D  P  K  F  Q  G  K  A  T  I  T  A  D  T  S  A  S

ACAGCCTACATGGAGCTCAGCAGCCTGAGATCTGAGGACACTGCCGTCTATTACTGTGCT
 T  A  Y  M  E  L  S  S  L  R  S  E  D  T  A  V  Y  Y  C  A

AGATGGTTACGACATTTTTACTATGCTATGGACTACTGGGGTCAAGGAACCCTGGTCACC
 R  W  L  R  H  F  Y  Y  A  M  D  Y  W  G  Q  G  T  L  V  T

HindIII
GTCTCCTCAGGTGAGTCCTCACAAAAGCTT
 V  S  S
```

Fig. 13

```
NheI
GCTAGCACCACCATGAGTGTGCCCACTCAACTCCTGGGGTTGCTGCTGCTGTGGCTTACA
        M  S  V  P  T  Q  L  L  G  L  L  L  L  W  L  T

GACGCACGATGTGACATCCAGATGACTCAGTCTCCATCCTCCCTGTCTGCATCTGTGGGA
 D  A  R  C  D  I  Q  M  T  Q  S  P  S  S  L  S  A  S  V  G

GACAGAGTCACCATCACATGTCGAGCAAGTGAGAACATTTACTACAGTTTAGCATGGTAT
 D  R  V  T  I  T  C  R  A  S  E  N  I  Y  Y  S  L  A  W  Y

CAGCAGAAGCCAGGGAAAGCCCCTAAGCTCCTGATCTATAATGCAAACAGCTTGGAAGAT
 Q  Q  K  P  G  K  A  P  K  L  L  I  Y  N  A  N  S  L  E  D

GGTGTCCCATCGAGGTTCAGTGGCAGTGGATCTGGGACACAGTATACTCTCACCATCAGC
 G  V  P  S  R  F  S  G  S  G  S  G  T  Q  Y  T  L  T  I  S

AGCCTGCAGCCTGAAGATTTTGCAACTTATTACTGTAAACAGGCTTATGACGTTCCGTAC
 S  L  Q  P  E  D  F  A  T  Y  Y  C  K  Q  A  Y  D  V  P  Y

EcoRI
ACGTTCGGACAAGGGACCAAGGTGGAAATCAAACGTGAGTAGAATTTAAAGAATTC
 T  F  G  Q  G  T  K  V  E  I  K
```

HUMANIZED ANTI-α 9 INTEGRIN ANTIBODIES AND THE USES THEREOF

CROSS-REFERENCE TO RELATED APPLICATIONS

This application is the national phase of PCT application PCT/JP2009/050606 having an international filing date of 13 Jan. 2009, which claims benefit of US provisional application No. 61/020,527 filed 11 Jan. 2008. The contents of the above patent applications are incorporated by reference herein in their entirety.

REFERENCE TO SEQUENCE LISTING FILED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
|---|---|---|
| 643102001200Seqlist.txt | Jul. 9, 2010 | 61,435 bytes |

1. FIELD OF THE INVENTION

The present invention relates to humanized antibodies that immunospecifically recognize human α9 integrin and to their therapeutic and diagnostic uses for various diseases or disorders that are associated with or involve α9 integrin, including cancer, inflammatory diseases, autoimmune diseases, and the like.

2. BACKGROUND OF THE INVENTION

Cells adhere to extracellular matrix (hereinafter abbreviated as ECM) mediated by a group of cell surface receptors which are termed integrins. Integrins perform their functions by forming 1:1 heterodimers of α and β chains. At least 18 types of α chain, 8 types of β chain and 24 types of αβ heterodimer have been identified and confirmed so far. It is known that each integrin recognizes a specific ligand. Integrins are classified into subfamilies depending upon their ligand specificities or functions, and divided into collagen receptors, laminin receptors, RGD receptors recognizing an Arg-Gly-Asp (RGD) sequence present in fibronectin, vitronectin, etc., and leukocyte-specific receptors present only in leukocytes (Hynes, R. O., 2002, Integrins: Bidirectional, Allosteric Signaling Machines. *Cell* 110: 673-87; Miyasaka, M., 2000, New edition of *Adhesion Molecule Handbook*, Shujunsya). The α4 and α9 integrins are members of a subfamily that does not belong to any of these types and called the α4 integrin subfamily (Elise L. Palmer, Curzio Rfiegg, Ronald Ferrando, Robert Pytela, Sheppard D., 1993, Sequence and Tissue Distribution of the Integrin α9 Subunit, a Novel Partner of β1 That Is Widely Distributed in Epithelia and Muscle. *The Journal of Cell Biology*, 123: 1289-97). Meanwhile, ECM used to be considered so far to serve as a mere cementing substance between cells. It has now become clear that the integrin-mediated ECM-cell interaction is significantly involved in regulating the growth, adhesion, movement, etc. of cells and associated with the onset of diseases including a progression of cancer, an exacerbation of inflammation, and the like.

For example, osteopontin (hereinafter abbreviated as OPN) which is one of the ECMs is a secreted, acidic phosphorylated glycoprotein with a molecular weight of about 41 kDa and is a molecule, whose expression is widely observed in breast milk, urine, renal tubules, osteoclasts, osteoblasts, macrophages, activated T cells, tumor tissues, and so forth. OPN has the adhesion sequences, GRGDS (SEQ ID NO:1) at the center of its molecule, the SVVYGLR (SEQ ID NO:2) sequence in human OPN or the SLAYGLR (SEQ ID NO:3) sequence in mouse OPN, and a thrombin-cleavage site in close proximity thereto, and binds through the GRGDS (SEQ ID NO:1) sequence to the RGD integrin or to the α4 (α4β1) and α9 (α9β1) integrins through the SVVYGLR (SEQ ID NO:2) sequence or the SLAYGLR (SEQ ID NO:3) sequence.

WO 02/081522 discloses a therapeutic effect on rheumatoid arthritis or hepatitis by inhibiting the OPN functions using OPN knockout mice or neutralizing antibodies against OPN. Moreover, this publication discloses that the SVVYGLR (SEQ ID NO:2) sequence is essential as recognizing the α9 and α4 integrins for pathogenesis of an inflammatory disease and that receptors for OPN are expressed in immunocompetent cells or the like and associated with an inflammatory disease.

Differences in binding profile have been found in that α4β1 binds both to OPN not cleaved with thrombin (uncleaved OPN) and to the N-terminal fragment of thrombin-cleaved OPN (cleaved OPN), whereas α9β1 binds only to the cleaved OPN (Y. Yokosaki, et al., (1999) *The Journal of Biological Chemistry*, 274: 36328-36334; P. M. Green, et al., (2001) *FEBS Letters*, 503: 75-79; S. T. Barry, et al., (2000) *Experimental Cell Research*, 258: 342-351).

The α4 and α9 integrins share many common ligands other than OPN. Known ligands are the EDA domain of fibronectin, propeptide-von Willebrand factor (pp-vWF), tissue transglutaminase (tTG), blood coagulation factor XIII, vascular cell adhesion molecule-1(VCAM-1), etc. In addition, the CS-1 domain of fibronectin, MadCAM-1 (α4β7), etc. are known as the ligands specifically recognized by the α4 integrin. Tenascin-C, plasmin, etc. are known as the ligands specifically recognized by the α9 integrin.

The amino acid sequences for the integrin subunits α9, α4 and β1 are publicly known. For instance, human α9 is registered as NM_002207, mouse α9 as NM_133721, human α4 as NM_000885, mouse α4 as NM_010576, human β1 as X07979, and mouse β1 as NM_010578, at the GenBank. These integrins are also known to have high similarities between species in amino acid sequence.

3. SUMMARY OF THE INVENTION

While a variety of drugs are known at present for the treatment of cancer, inflammatory diseases and autoimmune diseases, it has been desired to develop a preventive and/or therapeutic agent, etc. having more improved therapeutic effects on cancer, inflammatory diseases and autoimmune diseases. The present invention is based, in part, on the discovery by the present inventors that a specific inhibitory antibody against the α9 integrin has cancer-suppressing and anti-inflammatory effects.

Previously, the present inventors isolated mouse monoclonal antibodies that immunospecifically recognize human α9 integrin and are produced by hybridoma clones, 1K11, 21C5, 24I11, 25B6 and 28S1 (Depository Accession Nos. FERM BP-10510, FERM BP-10511, FERM BP-10512, FERM BP-10513 and FERM BP-10832, respectively), and those that immunospecifically recognize mouse α9 integrin and are produced by hybridoma clones, 18R18D, 12C4'58, 11L2B and 55A2C (Depository Accession Nos. FERM ABP-10195, FERM ABP-10196, FERM ABP-10197 and FERM ABP-10198, respectively). Herein, the hybridoma clone designations are interchangeably used as the designations of the monoclonal antibodies produced by the clones. All of these mouse anti-human α9 integrin antibodies were of IgG1 isotype. Some of these monoclonal antibodies inhibit the binding between human and/or mouse α9 integrin and a ligand of α9 integrin, such as osteopontin. Thus, these anti-α9 integrin antibodies inhibit the α9 integrin functions and exhibit therapeutic effects on cancer, e.g., the growth or metastasis of cancer cells, and on inflammatory diseases, e.g., rheumatoid arthritis, osteoarthritis, hepatitis, bronchial asthma, fibrosis, diabetes mellitus, arteriosclerosis, multiple sclerosis, granuloma, an inflammatory bowel disease (ulcerative colitis and Crohn's disease), an autoimmune disease, and the like.

Furthermore, the anti-α9 integrin antibodies of the present invention can be used as an in vivo diagnostic agent to detect the presence and the level of α9 integrin expression in a subject, thereby diagnosing a disorder or a disease involving α9 integrin.

However, since these monoclonal antibodies are of mouse origin, possible adverse effects due to their immunogenicity in humans have hampered their direct applications to diagnostic or therapeutic uses in humans. In order to reduce the immunogenicity, the present inventors have prepared a humanized antibody that have biological activities corresponding to those exhibited by the original mouse anti-α9 integrin antibody from which said humanized antibody was derived.

Accordingly, the present invention provides a humanized antibody or an antigen-binding fragment thereof, which immunospecifically recognizes human α9 integrin, said antibody comprising an antigen-binding region partially derived from a non-human origin and partially derived from a human origin. In a specific embodiment, the humanized antibody or an antigen-binding fragment thereof of the present invention comprises a complementarity determining region (CDR) derived from a non-human source (donor), such as 1K11, 21C5, 24I11, 25B6 and 28S1 monoclonal antibodies, and a framework region (FR) derived from a human source (acceptor). In one embodiment, said humanized antibody or an antigen-binding fragment thereof inhibits the binding between human α9 integrin and a ligand of human α9 integrin.

In a specific embodiment, said humanized antibody or an antigen-binding fragment thereof that immunospecifically recognizes human α9 integrin comprises: (i) a heavy chain (H-chain) comprising at least one H-chain FR (FRH) derived from a variable region (V-region) of a human H-chain, and at least one H-chain complementarity determining region (CDRH) derived from at least one of the CDRHs of a non-human antibody that immunospecifically recognizes human α9 integrin; or (ii) a light chain (L-chain) comprising at least one L-chain FR (FRL) derived from a V-region of a human L-chain, and at least one L-chain complementarity determining region (CDRL) derived from at least one of the CDRLs of a non-human antibody that immunospecifically recognizes human α9 integrin; or both (i) and (ii) above. For example, said non-human antibody, from which at least one of the CDRHs and/or at least one of the CDRLs of the humanized antibody of the invention is derived, is a monoclonal antibody produced by a hybridoma selected from the group consisting of Accession Nos. FERM BP-10510, FERM BP-10511, FERM BP-10512, FERM BP-10513 and FERM BP-10832.

In a preferred specific embodiment, the humanized antibody or an antigen-binding fragment thereof, of the present invention comprises: (i) at least one FRH derived from a human FRH, and at least one CDRH comprising an amino acid sequence selected from the group consisting of the amino acid sequences of SEQ ID NOS:4, 5 and 6; or (ii) at least one FRL derived from a human FRL, and at least one CDRL comprising an amino acid sequence selected from the group consisting of the amino acid sequences of SEQ ID NOS:11, 12 and 13; or (iii) both (i) and (ii) above. Said humanized antibody or an antigen-binding fragment thereof, of the present invention may comprise CDRH1, CDRH2 and CDRH3, which comprise the amino acid sequences of SEQ ID NOS:4, 5 and 6, respectively. In the alternative, said humanized antibody or an antigen-binding fragment thereof, of the present invention comprises CDRL1, CDRL2 and CDRL3, which comprise the amino acid sequences of SEQ ID NOS: 11, 12 and 13, respectively. In a preferred embodiment, said humanized antibody or an antigen-binding fragment thereof, of the present invention comprises CDRH1, CDRH2, CDRH3, CDRL1, CDRL2 and CDRL3, which comprise the amino acid sequences of SEQ ID NOS:4, 5, 6, 11, 12 and 13, respectively. In another alternative, said humanized antibody or an antigen-binding fragment thereof, of the present invention comprises a FRH derived from a variable region of a human H-chain encoded by GenBank Accession No. X65891 (SEQ ID NO:18), or a FRL derived from a variable region of a human κ-L-chain encoded by GenBank Accession No. X72441 (SEQ ID NO:23). In a preferred embodiment, the FRH of the humanized antibody of the present invention comprises at least one amino acid sequence selected from the group consisting of the amino acid sequences of SEQ ID NOS:19, 20, 21 and 22 (FRH1, FRH2, FRH3 and FRH4, respectively, encoded by the corresponding portions of X65891). In another preferred embodiment, the FRL of the humanized antibody of the present invention comprises at least one amino acid sequence selected from the group consisting of the amino acid sequences of SEQ ID NOS:24, 25, 26 and 27 (FRL1, FRL2, FRL3 and FRL4, respectively, encoded by the corresponding portions of X72441). In a most preferred embodiment, the humanized antibody or an antigen-binding fragment thereof, of the present invention comprises: (i) a H-chain variable region (VH region) comprising the amino acid sequence of SEQ ID NO:29; or (ii) a L-chain variable region (VL region) comprising the amino acid sequence of SEQ ID NO:31; or (iii) both (i) and (ii) above.

In another preferred specific embodiment, the humanized antibody or an antigen-binding fragment thereof, of the present invention comprises: (i) at least one FRH derived from a human FRH, and at least one CDRH comprising an amino acid sequence selected from the group consisting of the amino acid sequences of SEQ ID NOS:32, 33 and 34; or (ii) at least one FRL derived from a human FRL, and at least one CDRL comprising an amino acid sequence selected from the group consisting of the amino acid sequences of SEQ ID NOS:37, 38 and 39; or (iii) both (i) and (ii) above. Said humanized antibody or an antigen-binding fragment thereof, of the present invention may comprise CDRH1, CDRH2 and CDRH3, which comprise the amino acid sequences of SEQ ID NOS:32, 33 and 34, respectively. In the alternative, said humanized antibody or an antigen-binding fragment thereof, of the present invention comprises CDRL1, CDRL2 and CDRL3, which comprise the amino acid sequences of SEQ ID NOS:37, 38 and 39, respectively. In a preferred embodiment, said humanized antibody or an antigen-binding fragment thereof, of the present invention comprises CDRH1, CDRH2, CDRH3, CDRL1, CDRL2 and CDRL3, which comprise the amino acid sequences of SEQ ID NOS:32, 33, 34, 37, 38 and 39, respectively.

In another preferred specific embodiment, the humanized antibody or an antigen-binding fragment thereof, of the present invention comprises: (i) at least one FRH derived from a human FRH, and at least one CDRH comprising an amino acid sequence selected from the group consisting of the amino acid sequences of SEQ ID NOS:42, 43 and 44; or (ii) at least one FRL derived from a human FRL, and at least one CDRL comprising an amino acid sequence selected from the group consisting of the amino acid sequences of SEQ ID NOS:47, 48 and 49; or (iii) both (i) and (ii) above. Said humanized antibody or an antigen-binding fragment thereof, of the present invention may comprise CDRH1, CDRH2 and CDRH3, which comprise the amino acid sequences of SEQ ID NOS:42, 43 and 44, respectively. In the alternative, said humanized antibody or an antigen-binding fragment thereof, of the present invention comprises CDRL1, CDRL2 and CDRL3, which comprise the amino acid sequences of SEQ ID NOS:47, 48 and 49, respectively. In a preferred embodiment, said humanized antibody or an antigen-binding fragment thereof, of the present invention comprises CDRH1, CDRH2, CDRH3, CDRL1, CDRL2 and CDRL3, which comprise the amino acid sequences of SEQ ID NOS: 42, 43, 44, 47, 48 and 49, respectively.

In another preferred specific embodiment, the humanized antibody or an antigen-binding fragment thereof, of the present invention comprises: (i) at least one FRH derived from a human FRH, and at least one CDRH comprising an amino acid sequence selected from the group consisting of the amino acid sequences of SEQ ID NOS:52, 53 and 54; or (ii) at least one FRL derived from a human FRL, and at least one CDRL comprising an amino acid sequence selected from the group consisting of the amino acid sequences of SEQ ID NOS:57, 58 and 59; or (iii) both (i) and (ii) above. Said humanized antibody or an antigen-binding fragment thereof, of the present invention may comprise CDRH1, CDRH2 and CDRH3, which comprise the amino acid sequences of SEQ ID NOS:52, 53 and 54, respectively. In the alternative, said humanized antibody or an antigen-binding fragment thereof, of the present invention comprises CDRL1, CDRL2 and CDRL3, which comprise the amino acid sequences of SEQ ID NOS:57, 58 and 59, respectively. In a preferred embodiment, said humanized antibody or an antigen-binding fragment thereof, of the present invention comprises CDRH1, CDRH2, CDRH3, CDRL1, CDRL2 and CDRL3, which comprise the amino acid sequences of SEQ ID NOS:52, 53, 54, 57, 58 and 59, respectively.

In another preferred specific embodiment, the humanized antibody or an antigen-binding fragment thereof, of the present invention comprises: (i) at least one FRH derived from a human FRH, and at least one CDRH comprising an amino acid sequence selected from the group consisting of the amino acid sequences of SEQ ID NOS:62, 63 and 64; or (ii) at least one FRL derived from a human FRL, and at least one CDRL comprising an amino acid sequence selected from the group consisting of the amino acid sequences of SEQ ID NOS:67, 68 and 69; or (iii) both (i) and (ii) above. Said humanized antibody or an antigen-binding fragment thereof, of the present invention may comprise CDRH1, CDRH2 and CDRH3, which comprise the amino acid sequences of SEQ ID NOS:62, 63 and 64, respectively. In the alternative, said humanized antibody or an antigen-binding fragment thereof, of the present invention comprises CDRL1, CDRL2 and CDRL3, which comprise the amino acid sequences of SEQ ID NOS:67, 68 and 69, respectively. In a preferred embodiment, said humanized antibody or an antigen-binding fragment thereof, of the present invention comprises CDRH1, CDRH2, CDRH3, CDRL1, CDRL2 and CDRL3, which comprise the amino acid sequences of SEQ ID NOS:62, 63, 64, 67, 68 and 69, respectively.

The present invention further provides an isolated nucleic acid molecule comprising a nucleotide sequence encoding the humanized antibody or an antigen-binding fragment thereof of the present invention which immunospecifically recognizes human α9 integrin. Specifically, the present invention provides an isolated nucleic acid molecule comprising a nucleotide sequence encoding a humanized H-chain comprising at least one amino acid sequence selected from the group consisting of SEQ ID NOS:4, 5, 6, 32, 33, 34, 42, 43, 44, 52, 53, 54, 62, 63 and 64, or a humanized L-chain comprising at least one amino acid sequence selected from the group consisting of SEQ ID NOS:11, 12, 13, 37, 38, 39, 47, 48, 49, 57, 58, 59, 67, 68 and 69, or both said humanized H-chain and said humanized L-chain. In a preferred specific embodiment, such an isolated nucleic acid molecule comprises the nucleotide sequence of SEQ ID NO:28, which encodes a VH region, or a nucleotide sequence encoding the amino acid sequence of SEQ ID NO:29. In another preferred specific embodiment, such an isolated nucleic acid molecule comprises the nucleotide sequence of SEQ ID NO:30, which encodes a VL region, or a nucleotide sequence encoding the amino acid sequence of SEQ ID NO:31. In yet another preferred specific embodiment, the isolated nucleic acid molecule of the present invention comprises the nucleotide sequences of both SEQ ID NO:28 and 30. In yet another preferred specific embodiment, the isolated nucleic acid molecule of the present invention further comprises a nucleotide sequence encoding a signal peptide of donor origin, such as the amino acid sequences of SEQ ID NOS:10 and 17, respectively, or of heterologous origin.

The present invention further provides a vector, e.g., an expression vector, comprising a nucleotide sequence encoding a H-chain or a L-chain, or both, of the humanized antibody or an antigen-binding fragment thereof of the present invention that immunospecifically recognizes human α9 integrin. In such a vector, the nucleotide sequence of the present invention may be operably linked to one or more regulatory elements. The nucleotide sequence of the present invention may include a nucleotide sequence encoding a signal peptide native to a non-human donor antibody from which a CDR is derived, or a signal peptide of heterologous origin.

Furthermore, the present invention provides a host cell comprising the nucleic acid molecule of the present invention, including a vector comprising the nucleic acid molecule of the present invention. In one embodiment, the present invention provides an isolated host cell comprising a first nucleic acid molecule encoding a humanized H-chain of the present invention and a second nucleic acid molecule encoding a humanized L-chain of the present invention, said first and second nucleic acid molecules are each operably linked to a regulatory element in such a way that the biologically functional humanized antibody or antigen-binding fragment thereof of the present invention is expressed.

Accordingly, the present invention further provides a method for preparing the humanized antibody of the present invention, comprising culturing the host cell of the invention under conditions so that the humanized antibody is expressed; and collecting the produced humanized antibody.

The present invention further provides a composition comprising at least one of the humanized antibodies of the present invention. In addition, the present invention provides a pharmaceutical composition for preventing or treating a disorder or disease that is associated with α9 integrin, comprising at least one of the humanized antibodies of the present invention, and a pharmaceutically acceptable carrier. Either of said compositions can further comprise another active compound that can additively or synergistically ameliorate the disorder or disease. Such an active compound includes, but not by way of limitation, anti-inflammatory compounds, chemotherapeutic compounds, and the like, as well as an antibody or an antigen-binding fragment thereof, such as an antibody that can immunospecifically bind human α4 integrin.

In another aspect, the present invention provides a method for preventing or treating a disorder or disease that is associated with or involves α9 integrin, said method comprising administering a prophylactically or therapeutically effective amount of at least one of the humanized antibodies of the present invention to a subject in need thereof. For such uses, the humanized antibody of the present invention may be conjugated to a therapeutic moiety that enhances the biological effect of the humanized antibody. Examples of such a therapeutic moiety include another antibody, such as anti-α4 antibody (e.g., to form a bispecific antibody), cytotoxins that are cytostatic or cytocidal, radioactive elements, and/or other therapeutic agents, including anti-inflammatory agents, antibiotics, and the like.

In yet another aspect, the present invention provides a method for diagnosing a disorder or disease, in a subject, that is associated with or involves α9 integrin, said method comprising administering a diagnostically effective amount of the humanized antibody of the present invention to a subject to be examined. For such diagnostic uses, the humanized antibody of the present invention may be labeled with detectable markers, such as radioactive elements.

3.1. Definitions

As used herein, the term "antibody" refers to an antibody molecule capable of immunospecifically binding to a desired antigen, such as the α9 integrin, and encompasses an antibody molecule as a whole or a fragment thereof, including an antigen-binding fragment.

The term "immunospecifically recognize" used herein refers to an ability of an antibody or an antigen-binding fragment thereof to bind specifically to a target polypeptide or protein, in particular, human α9 integrin. Such an antibody does not non-specifically bind to other polypeptides or proteins. However, an antibody or an antigen-binding fragment thereof that immunospecifically binds to the target polypeptide or protein (e.g., human α9 integrin) may cross-react with other antigens. For example, the humanized antibody or an antigen-binding fragment of the present invention that immunospecifically recognizes human α9 integrin may cross-react with, for example, murine α9 integrin. Preferably, an antibody or an antigen-binding fragment thereof that immunospecifically binds to human α9 integrin does not cross-react with other antigens.

The term "an antigen-binding fragment" used herein refers to any fragment of an antibody that retains an ability to immunospecifically bind to a target polypeptide or protein, in particular, human α9 integrin and/or mouse α9 integrin, and includes single chain antibodies, Fab fragments, F(ab')$_2$ fragments, disulfide-linked Fvs, and fragments containing either a variable region of a light chain (VL) and/or a variable region of a heavy chain (VH) or even a complementary determining region (CDR) that specifically binds to a target polypeptide or protein. Thus, such antigen-binding fragments of humanized antibody may or may not include partial or full-length human constant regions. Various methods for obtaining the antibody fragments described above are well known in the art.

The term "derived from a human source" or "derived from a non-human source" used herein refers to an antibody portion whose amino acid sequence is derived from a corresponding portion of a human antibody or of a non-human antibody.

The term "an acceptor sequence" used herein refers to a nucleotide sequence or an amino acid sequence of framework regions from a human antibody VH or VL region that serves as an acceptor for CDRs from a donor antibody, which is usually a non-human antibody.

4. BRIEF DESCRIPTION OF THE FIGURES

FIG. 1 shows the nucleotide sequence (SEQ ID NO:7) of mouse 24I11 VH cDNA along with the deduced amino acid sequence (SEQ ID NO:8). Amino acid residues are shown in single letter code. The signal peptide sequence (SEQ ID NO:10) is in italic. The N-terminal amino acid residue (E) of the mature VH is double-underlined. CDR sequences according to the definition of Kabat et al. (Sequences of Proteins of Immunological Interests, Fifth edition, NIH Publication No. 91-3242, U.S. Department of Health and Human Services, 1991) are underlined.

FIG. 2 shows the nucleotide sequence (SEQ ID NO:14) of mouse 24I11 VL cDNA along with the deduced amino acid sequence (SEQ ID NO:15). Amino acid residues are shown in single letter code. The signal peptide sequence (SEQ ID NO:17) is in italic. The N-terminal amino acid residue (D) of the mature VL is double-underlined. CDR sequences according to the definition of Kabat et al. (1991) are underlined.

FIG. 3 shows the nucleotide sequence (SEQ ID NO:72) of the designed 24I11 VH gene flanked by SpeI and HindIII sites (underlined), along with the deduced amino acid sequence (SEQ ID NO:8). Amino acid residues are shown in single letter code. The signal peptide sequence (SEQ ID NO:10) is in italic. The N-terminal amino acid residue (E) of the mature VH is double-underlined. CDR sequences according to the definition of Kabat et al. (1991) are underlined. The intron sequence is in italic.

FIG. 4 shows the nucleotide sequence (SEQ ID NO:73) of the designed 24I11 VL gene flanked by NheI and EcoRI sites (underlined), along with the deduced amino acid sequence (SEQ ID NO:15). Amino acid residues are shown in single letter code. The signal peptide sequence (SEQ ID NO:17) is in italic. The N-terminal amino acid residue (D) of the mature VL is double-underlined. CDR sequences according to the definition of Kabat et al. (1991) are underlined. The intron sequence is in italic.

FIG. 5 shows the schematic structure of pCh24I11 and pHu24I11 (collectively Expression Vector). Proceeding clockwise from the SaiI site at the top, the plasmid contains the heavy chain transcription unit starting with the human cytomegalovirus (CMV) major immediate early promoter and enhancer (CMV promoter) to initiate transcription of the antibody heavy chain gene. The CMV promoter is followed by the VH exon, a genomic sequence containing the human gamma-1 heavy chain constant region including the CH1, hinge, CH2 and CH3 exons with the intervening introns, and a polyadenylation site of the gamma-1 gene for mRNA processing following CH3. After the heavy chain gene sequence, the light chain transcription unit begins with the CMV promoter, followed by the VL exon and a genomic sequence containing the human kappa chain constant region exon (CL) with part of the intron preceding it, and a poly A signal of the kappa gene. The light chain gene is then followed by the SV40 early promoter (SV40 promoter), the *E. coli* xanthine guanine phosphoribosyl transferase gene (gpt), and a segment containing the SV40 polyadenylation site (SV40 poly(A) site). Finally, the plasmid contains a part of the plasmid pUC19, comprising the bacterial origin of replication (pUC ori) and beta-lactamase gene (beta lactamase).

FIG. 6 shows the alignment of the amino acid sequences of 24I11 VH (SEQ ID NO:9), humanized 24I11 (Hu24I11) VH (SEQ ID NO:29) and FRH1 (SEQ ID NO:19), FRH2 (SEQ ID NO:20), FRH3 (SEQ ID NO:21) and FRH4 (SEQ ID NO:22) of human acceptor sequences, derived from the amino acid sequence encoded by the nucleotide sequence of GenBank Accession No. X65891. Amino acid residues are shown in single letter code. Numbers above the sequences indicate the positions according to Kabat et al. (1991). CDR sequences defined by Kabat et al. (1991) are underlined. Double-underlined residues were predicted to contact with the CDRs and the mouse residues were retained at these locations in the humanized form. CDR residues in X65891 are omitted in the figure.

FIG. 7 shows the alignment of the amino acid sequences of 24I11 VL (SEQ ID NO:16), humanized 24I11 (Hu24I11) VL (SEQ ID NO:31) and FRL1 (SEQ ID NO:24), FRL2 (SEQ ID NO:25), FRL3 (SEQ ID NO:26) and FRL4 (SEQ ID NO:27) of human acceptor sequences, derived from the amino acid sequence encoded by the nucleotide sequence of GenBank Accession No. X72441. Amino acid residues are shown in single letter code. Numbers above the sequences indicate the positions according to Kabat et al. (1991). CDR sequences defined by Kabat et al. (1991) are underlined. Double-underlined residues were predicted to contact with the CDRs and the mouse residues were retained at these locations in the humanized form. CDR residues in X72441 are omitted in the figure.

FIG. 8 shows the oligonucleotides used for construction of the Hu24I11 VH gene.

FIG. 9 shows the oligonucleotides used for construction of the Hu24I11 VL gene.

FIG. 10 shows the oligonucleotides used for construction of the Hu24I11 VH gene flanked by SpeI and HindIII sites (SEQ ID NO:74 with 5'-GGG tail at 5'-terminal and CCC-3' tail at 3'-terminal). An arrow denotes the position and orientation (5' to 3') of each oligonucleotide. Amino acid residues of the signal peptide (SEQ ID NO:10) and the VH region (SEQ ID NO:29) are shown in single letter code.

FIG. 11 shows oligonucleotides used for construction of the Hu24I11 VL gene flanked by NheI and EcoRI sites (SEQ ID NO:75 with 5'-GGG tail at 5'-terminal and CCC-3' tail at 3'-terminal). An arrow denotes the position and orientation (5' to 3') of each oligonucleotide. Amino acid residues of the signal peptide (SEQ ID NO:17) and the VL region (SEQ ID NO:31) are shown in single letter code.

FIG. 12 shows the nucleotide sequence (SEQ ID NO:74) of the Hu24I11 VH gene flanked by SpeI and HindIII sites (underlined), along with the deduced amino acid sequence of the signal peptide (SEQ ID NO:10; shown in italic) and the VH region (SEQ ID NO:29). Amino acid residues are shown in single letter code. The N-terminal amino acid residue (Q) of the mature VH is double-underlined. CDR sequences according to the definition of Kabat et al. (1991) are underlined. The intron sequence is in italic.

FIG. 13 shows the nucleotide sequence (SEQ ID NO:75) of the Hu24I11 VL gene flanked by NheI and EcoRI sites (underlined), along with the deduced amino acid sequence of the signal peptide (SEQ ID NO:17; shown in italic) and the VL region (SEQ ID NO:31). Amino acid residues are shown in single letter code. The N-terminal amino acid residue (D) of the mature VL is double-underlined. CDR sequences according to the definition of Kabat et al. (1991) are underlined. The intron sequence is in italic.

Figure 14:
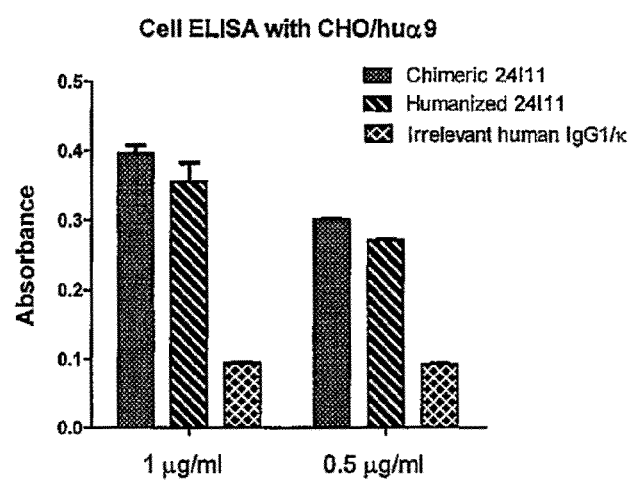

FIG. 14 shows the comparison of the affinity of chimeric and humanized 24I11 antibodies to human α9 integrin. The binding of chimeric and humanized 24I11 at 1 and 0.5 µg/ml to CHO/α9 cells was examined by cell ELISA. Experiments were carried out in triplicate. The mean absorbance value with SEM is shown in the figure.

Figure 15:
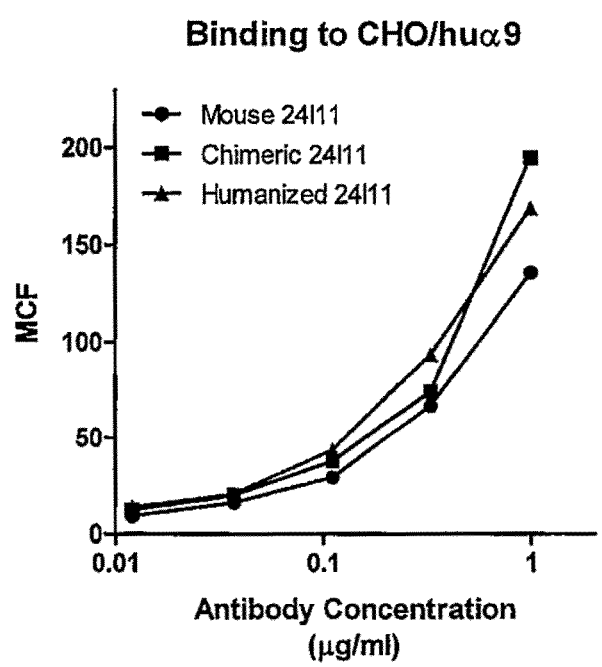

FIG. 15 shows the result of the FACS analysis of the binding of mouse, chimeric and humanized 24I11 antibodies to human α9 integrin. Each antibody was tested at 1, 0.33, 0.11, 0.037 and 0.012 µg/ml for binding to CHO/huα9 cells. Geometric mean channel fluorescence values (MCF; Y-axis) are plotted at each antibody concentration tested (X-axis) in the figure.

Figure 16:
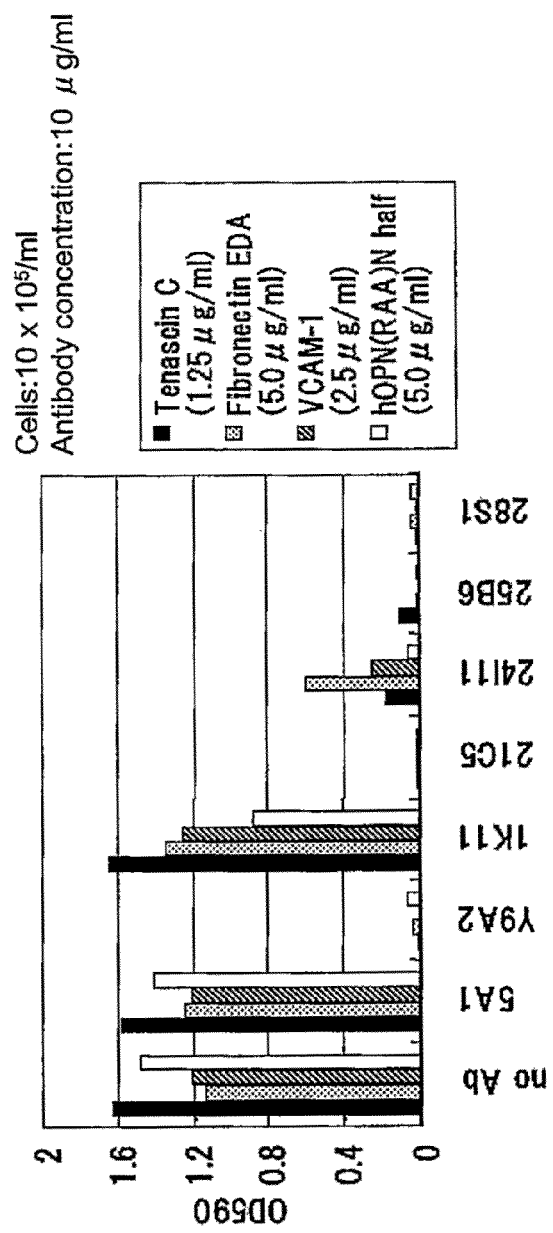

FIG. 16 shows the result of cell adhesion inhibitory activity of anti-human α9 integrin antibodies, between Human α9/CHO-K1 cells and hOPN(RAA)N-half, Tenascin-C, VCAM-1, or human fibronectin.

Figure 17:
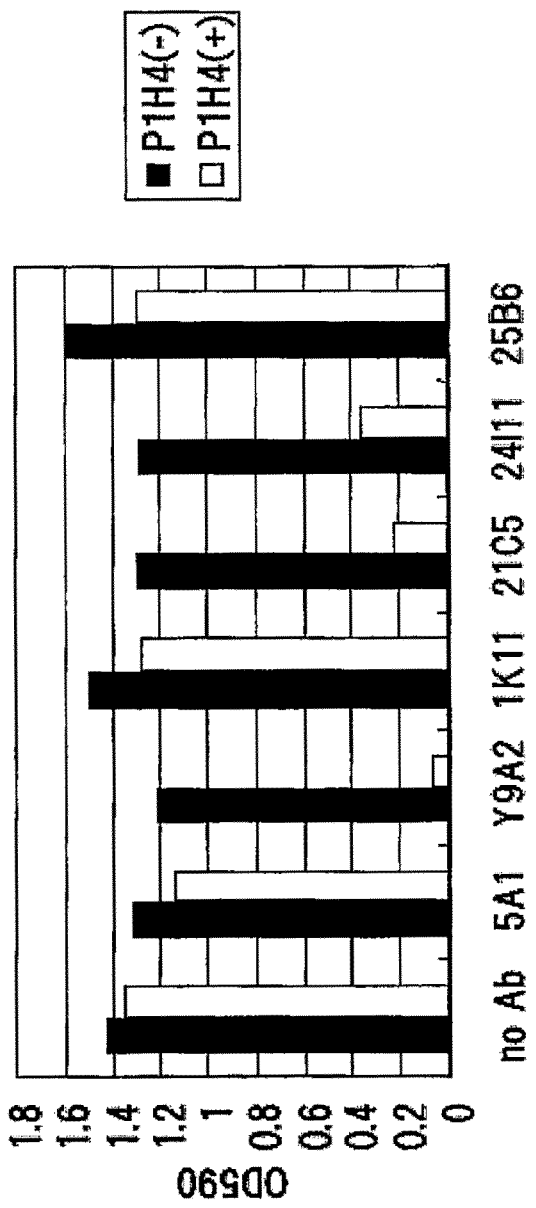

FIG. 17 shows the result of cell adhesion inhibitory effects of anti-human α9 integrin antibodies on human melanoma cells in the presence of anti-human α4 integrin.

Figure 18:
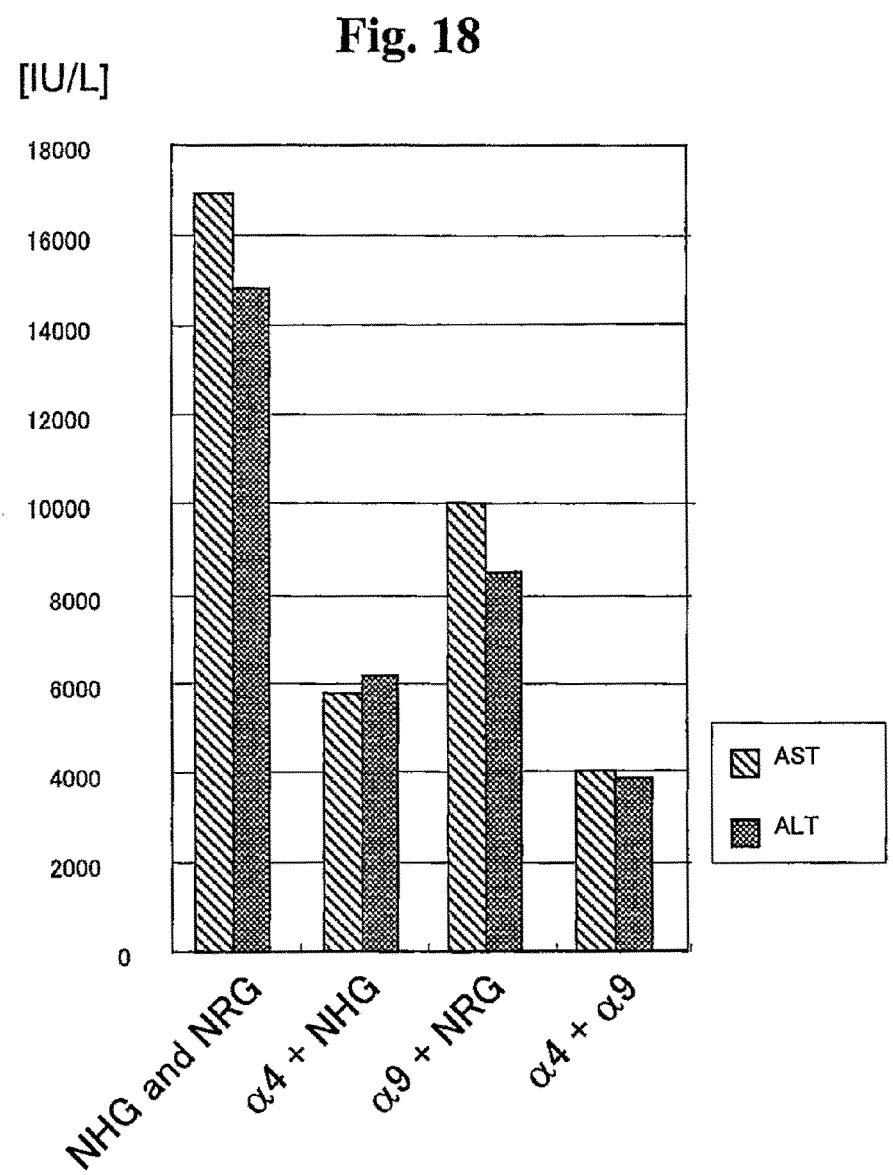

FIG. 18 shows therapeutic effects on hepatitis by the anti-α4 integrin antibodies and the anti-α9-integrin antibodies. In the Figure, NHG indicates normal hamster antibody and NRG indicates normal rat antibody.

Figure 19:
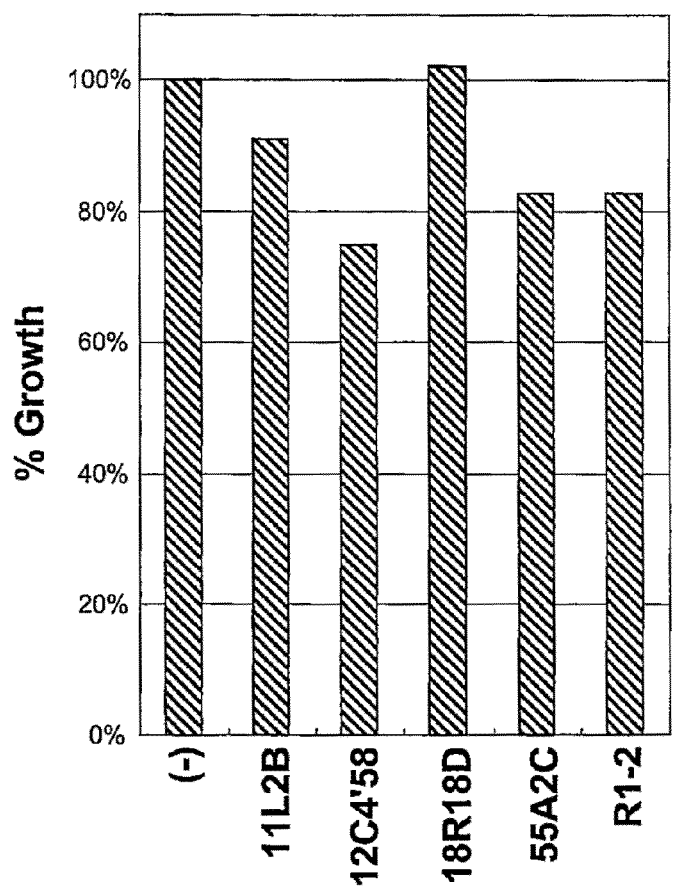

FIG. 19 shows that growth of the B16-BL6 cells was inhibited by the anti-α9 integrin antibodies.

Figure 20A:
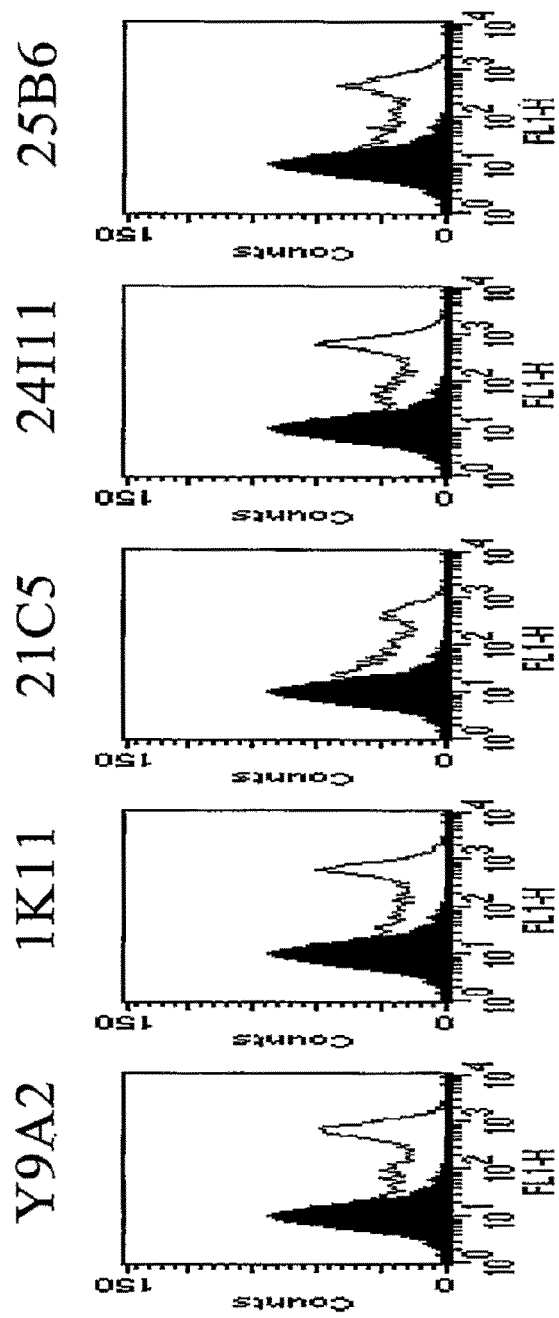
Figure 20B:
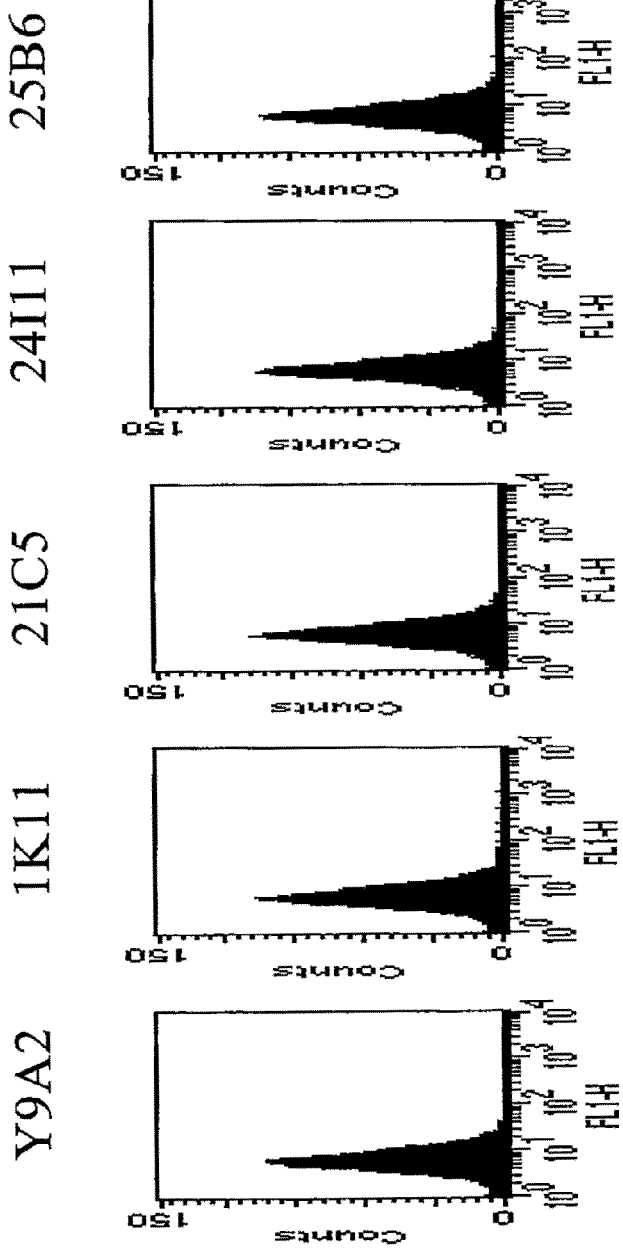
Figure 20C:
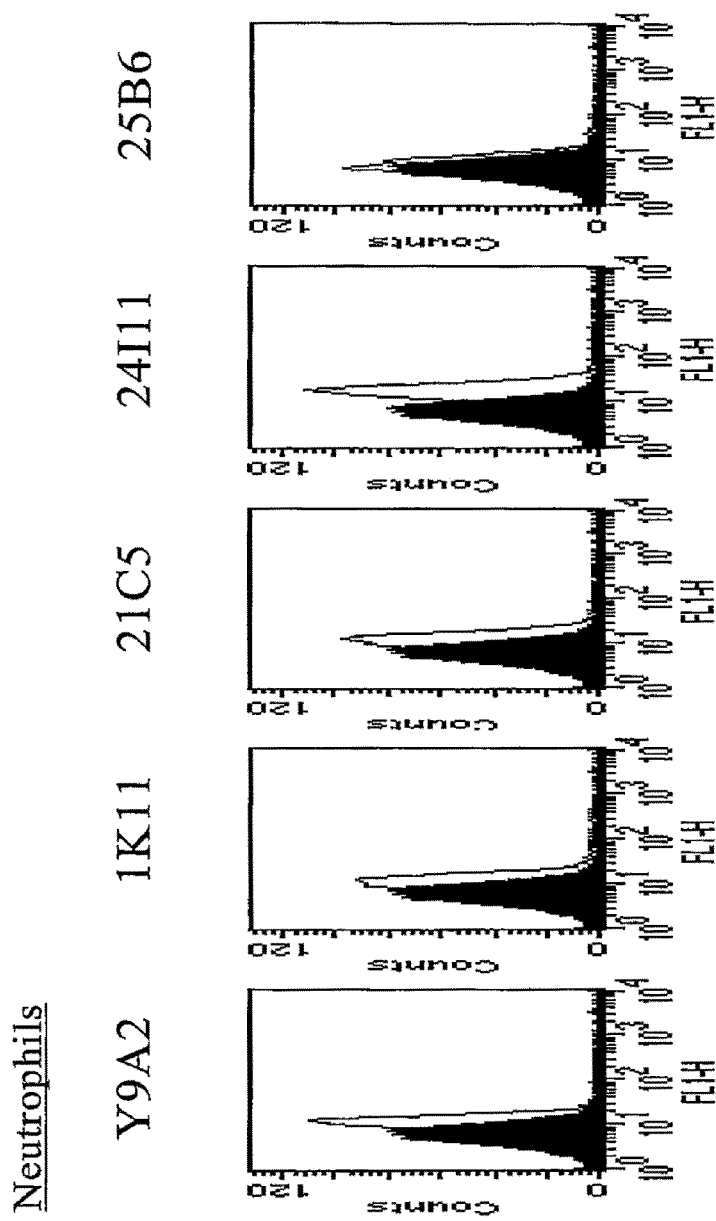

FIG. 20 shows the results of FACS analysis using anti-human α9 integrin antibodies for Human α9/CHO-K1 cells (FIG. 20a), Human α4/CHO-K1 (FIG. 20b) and human neutrophils (FIG. 20c).

Figure 21:
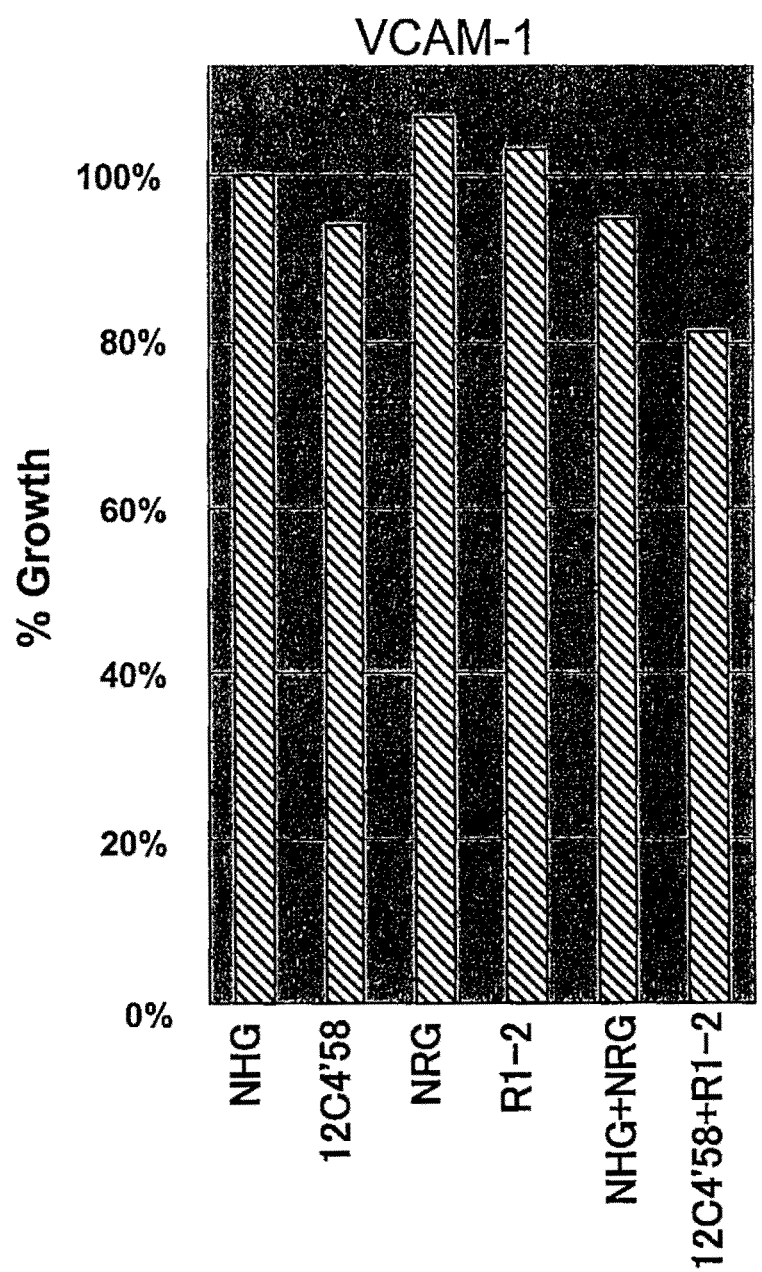

FIG. 21 shows the cell growth inhibition of the B16-BL6 cells by the anti-α9 integrin antibodies using immobilized VCAM-1 as an ECM.

Figure 22:
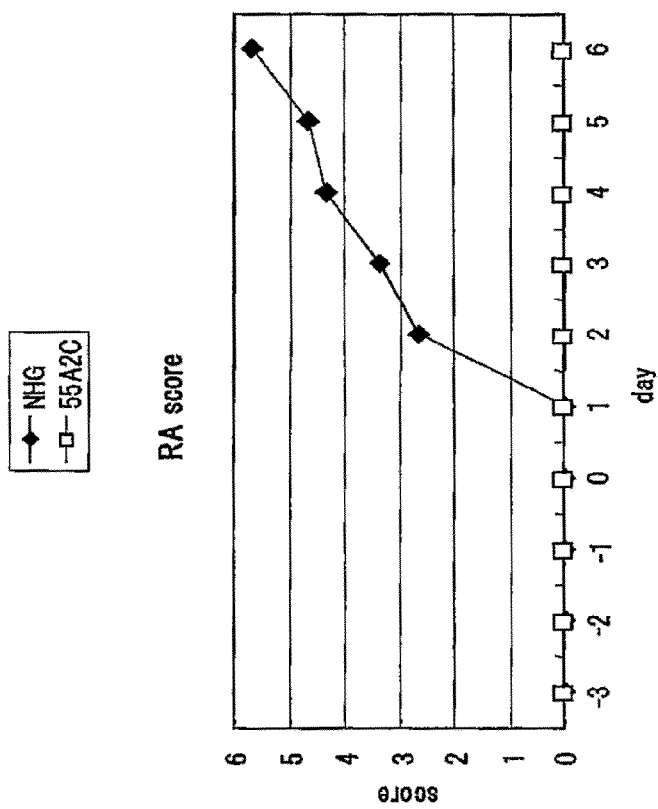

FIG. 22 shows the therapeutic effect of anti-α9 integrin in a mouse rheumatoid arthritis model.

5. DETAILED DESCRIPTION OF THE INVENTION 5.1. Preparation of Antibodies Against Human α9 Integrin Antibodies that immunospecifically recognize human α9 integrin or any epitope thereof may be generated by any suitable method known in the art.

The α9 integrin used as an antigen in the present invention may be (1) proteins derived from all cells from human that express α9 integrin, or all tissues where these cells are present, (2) recombinant proteins in which the α9 integrin-encoding gene DNA, preferably cDNA, is transfected into bacteria, yeast, cell lines including animal cells, etc. and expressed, or (3) synthetic proteins.

The α9 integrin includes polypeptides comprising substantially the same amino acid sequences as the amino acid sequences of human α9 integrins (SEQ ID NO:76, wherein 1-29 residues are the signal peptide).

Herein, the term "polypeptides comprising substantially the same amino acid sequence" means variant polypeptides comprising an amino acid sequence, in which multiple amino acids, preferably 1 to 10 amino acids and more preferably 1 to several (e.g., 1 to 5) amino acids are substituted, deleted and/or modified, as long as these variant polypeptides have biological properties substantially equivalent to the naturally occurring human α9 integrin; and variant polypeptides comprising an amino acid sequence, wherein multiple amino acids, preferably 1 to 10 amino acids and more preferably 1 to several (e.g., 1 to 5) amino acids are added to the amino acid sequence of naturally occurring human α9 integrin. Furthermore, the variant polypeptides may be those having a plurality of these substitutions, deletions, modifications and additions of amino acids.

The human α9 integrin as an antigen in the present invention can be produced by methods well known in the art, such as chemical synthesis method, cell culture method, etc., or their modifications, in addition to the gene recombinant techniques.

Examples of the methods for producing variant polypeptides include a synthetic oligonucleotide site-directed mutagenesis (gapped duplex method), a point mutagenesis method which involves introducing a point mutation at random by treatment with nitrite or sulfite, a method which involves preparing a deletion mutant with Bal31 enzyme, or other enzymes, a cassette mutagenesis, a linker scanning method, a miss incorporation method, a mismatch primer method, a DNA segment synthesis method, and the like.

The human α9 integrin to be used as an antigen in the present invention also includes a "part" of said α9 integrin. As used herein, the "part" refers to a part comprising a region required for binding to a ligand of the α9 integrin, for example, OPN, VCAM-1, tenascin-C, etc.; specifically, a part comprising the 14th-980th amino acid residues, and a part comprising the 11th-981st amino acid residues, of the mature human α9 integrin (the 30th-1035th amino acid residues of SEQ ID NO:76). The "part" of said α9 integrin can be produced by gene recombination or chemical synthesis according to methods known in the art described below, or modifications thereof, or can be produced by appropriately digesting the human α9 integrin isolated by the cell culture method with a proteolytic enzyme or the like.

As an antigen, a cell per se that overexpresses the α9 integrin on the cell membrane, or a membrane fraction thereof, can be also used. Cells overexpressing human α9 integrin can be prepared by recombinant DNA technologies well known in the art.

Using appropriate antigens prepared as described above, antibodies specific for human α9 integrin or any epitope thereof may be prepared by various methods well known in the art. Polyclonal antibodies to human α9 integrin can be produced by various procedures well known in the art. For example, an antigen of interest can be administered to various host animals including, but not limited to, rabbits, mice, rats, etc., to induce the production of antisera containing polyclonal antibodies specific for the antigen. Various adjuvants may be used to increase the immunological response, depending on the host species, and include but are not limited to, Freund's (complete and incomplete) adjuvant, mineral gels such as aluminum hydroxide, surface active substances such as lysolecithin, pluronic polyols, polyanions, peptides, oil emulsions, keyhole limpet hemocyanins, dinitrophenol, and potentially useful adjuvants for humans such as BCG (Bacille Calmette-Guerin) and *Corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas, pp. 563-681 (Elsevier, N.Y., 1981) (both of which are incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. In a non-limiting example; mice can be immunized with an antigen of interest or a cell expressing such an antigen. Once an immune response is detected, e.g., antibodies specific for the antigen are detected in the mouse serum, the mouse spleen is harvested and splenocytes isolated. The splenocytes are then fused by well known techniques to any suitable myeloma cells (e.g., P3U1, P3X63-Ag8, P3X63-Ag8-U1, P3NS1-Ag4, SP2/0-Ag14, P3X63-Ag8-653, etc.). Hybridomas are selected and cloned by limiting dilution. The hybridoma clones are then assayed by methods known in the art for cells that secrete antibodies capable of binding the antigen. Ascites fluid, which generally contains high levels of antibodies, can be generated by inoculating mice intraperitoneally with positive hybridoma clones.

Antibody fragments what recognize specific epitopes may be generated by known techniques. For example, Fab and F(ab')$_2$ fragments may be produced by proteolytic cleavage of immunoglobulin molecules, using enzymes such as papain (to produce Fab fragments) or pepsin (to produce F(ab')$_2$ fragments). F(ab')$_2$ fragments contain the complete light chain, and the variable region, the CH1 region and the hinge region of the heavy chain.

The antibodies of the invention or an antigen-binding fragment thereof can be also produced by any method known in the art for the synthesis of antibodies, in particular, by chemical synthesis or preferably, by recombinant expression techniques.

The nucleotide sequence encoding an antibody may be obtained from any information available to those skilled in the art (i.e., from Genbank, the literature, or by routine cloning and sequence analysis). If a clone containing a nucleic acid encoding a particular antibody or an epitope-binding fragment thereof is not available, but the sequence of the antibody molecule or epitope-binding fragment thereof is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from any tissue or cells expressing the antibody, such as hybridoma cells selected to express an antibody) by PCR amplification using synthetic primers hybridizable to the and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

5.2. Preparation of Recombinant Antibodies

Once the nucleotide sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., supra; and Ausubel et al., eds., 1998, Current Protocols in Molecular Biology, John Wiley & Sons, NY, which are both incorporated by reference herein in their entireties), to generate antibodies having a different amino acid sequence by, for example, introducing amino acid substitutions, deletions, and/or insertions into the epitope-binding domain regions of the antibodies or any portion of antibodies which may enhance or reduce biological activities of the antibodies.

Recombinant expression of an antibody requires construction of an expression vector containing a nucleotide sequence that encodes the antibody. Once a nucleotide sequence encoding an antibody molecule or a heavy or light chain of an antibody, or portion thereof has been obtained, the vector for the production of the antibody molecule may be produced by recombinant DNA technology using techniques well known in the art as discussed in the previous sections. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The nucleotide sequence encoding the heavy-chain variable region, light-chain variable region, both the heavy-chain and light-chain variable regions, an epitope-binding fragment of the heavy- and/or light-chain variable region, or one or more complementarity determining regions (CDRs) of an antibody may be cloned into such a vector for expression. Such a sequence may be fused with a polynucleotide encoding a signal peptide native to the original antibody or a heterologous signal peptide. Thus-prepared expression vector can be then introduced into appropriate host cells for the expression of the antibody. Accordingly, the invention includes host cells containing a polynucleotide encoding a humanized antibody or an antigen-binding fragment thereof that immunospecifically recognizes human α9 integrin.

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides or different selectable markers to ensure maintenance of both plasmids. Alternatively, a single vector may be used which encodes, and is capable of expressing, both heavy and light chain polypeptides. The coding sequences for the heavy and light chains may comprise cDNA or genomic DNA.

In another embodiment, antibodies can also be generated using various phage display methods known in the art. In phage display methods, functional antibody domains are displayed on the surface of phage particles which carry the polynucleotide sequences encoding them. In a particular embodiment, such phage can be utilized to display antigen binding domains, such as Fab and Fv or disulfide-bond stabilized Fv, expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage, including fd and M13. The antigen binding domains are expressed as a recombinantly fused protein to either the phage gene III or gene VIII protein. Examples of phage display methods that can be used to make the immunoglobulins, or fragments thereof, of the present invention include those disclosed in Brinkman et al., J. Immunol. Methods, 182:41-50, 1995; Ames et al., J. Immunol. Methods, 184:177-186, 1995; Kettleborough et al., Eur. J. Immunol., 24:952-958, 1994; Persic et al., Gene, 187:9-18, 1997; Burton et al., Advances in Immunology, 57:191-280, 1994; PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired fragments, and expressed in any desired host, including mammalian cells, insect cells, plant cells, yeast, and bacteria, e.g., as described in detail below. For example, techniques to recombinantly produce Fab, Fab' and F(ab)2 fragments can also be employed using methods known in the art such as those disclosed in PCT publication WO 92/22324; Mullinax et al., BioTechniques, 12(6):864-869, 1992; and Sawai et al., AJRI, 34:26-34, 1995; and Better et al., Science, 240:1041-1043, 1988 (each of which is incorporated by reference in its entirety). Examples of techniques which can be used to produce single-chain Fvs and antibodies include those described in U.S. Pat. Nos. 4,946,778 and 5,258,498; Huston et al., Methods in Enzymology, 203:46-88, 1991; Shu et al., PNAS, 90:7995-7999, 1993; and Skerra et al., Science, 240:1038-1040, 1988.

Once an antibody molecule of the invention has been produced by any methods described above, it may then be purified by any method known in the art for purification of an immunoglobulin molecule, for example, by chromatography (e.g., ion exchange, affinity, particularly by affinity for the specific antigen after Protein A or Protein G purification, and sizing column chromatography), centrifugation, differential solubility, or by any other standard techniques for the purification of proteins. Further, the antibodies of the present invention or fragments thereof may be fused to heterologous polypeptide sequences described herein or otherwise known in the art to facilitate purification.

For some uses, including in vivo use of antibodies in humans and in vitro detection assays, it may be preferable to use chimeric, humanized, or human antibodies. Chimeric antibodies and humanized antibodies are discussed in details in Section 5.3, infra.

Antibodies fused or conjugated to other compounds or heterologous polypeptides may be used in in vitro immunoassays, in purification methods (e.g., affinity chromatography), as well as in vivo therapeutic or diagnostic uses. See e.g., PCT publication Number WO 93/21232; EP 439,095; Naramura et al., Immunol. Lett., 39:91-99, 1994; U.S. Pat. No. 5,474,981; Gillies et al., PNAS, 89:1428-1432, 1992; and Fell et al., J. Immunol., 146:2446-2452, 1991, which are incorporated herein by reference in their entireties. For example, antibodies can be labeled in various ways using a known method or commercially available kit (e.g., biotin labeling, FITC labeling, APC labeling). As another example, antibodies may be conjugated to a therapeutic moiety that enhances the biological effect of the antibodies in vivo. Examples of such a therapeutic moiety include another antibody, cytotoxins that are cytostatic or cytocidal, radioactive element, and/or other therapeutic agents, including anti-inflammatory agents, antibiotics, and the like. In the present invention, the humanized anti-human α9 integrin may be conjugated to another antibody, such as anti-α4 antibody (e.g., to form a bispecific antibody). As another example, the humanized antibody of the present invention may be labeled with detectable markers, such as radioactive elements, for in vivo diagnostic uses.

5.3. Chimeric and Humanized Antibodies

A chimeric antibody is a molecule in which different portions of the antibody are derived from different animal species, such as antibodies having a variable region derived from a murine monoclonal antibody and a constant region derived from a human immunoglobulin. Methods for producing chimeric antibodies are known in the art. See e.g., Morrison, Science, 229:1202,.1985; Oi et al., BioTechniques, 4:214 1986; Gillies et al., J. Immunol. Methods, 125:191-202, 1989; U.S. Pat. Nos. 5,807,715; 4,816,567; and 4,816,397, which are incorporated herein by reference in their entireties.

A humanized antibody is a molecule that binds a desired antigen and comprises a variable region containing one or more complementarity determining regions (CDRs) derived from a non-human species and one or more framework regions derived from a human immunoglobulin molecule. The typical methods for humanizing non-human antibodies have been described in various references, such as those: by Queen et al., 1989, *Proc. Natl. Acad Sci. USA* 86:10029-10033 and U.S. Pat. Nos. 5,585,089 and 5,693,762; by Riechmann et al., *Nature,* 332:323, 1988; and by Tsurushita et al., *Methods* 36:69-83, 2005, all of which are incorporated herein by reference in their entireties). For example, the reference by Tsurushita et al. (2005, supra; hereafter "Tsurushita") provides a practical and instructive protocol for the humanization of mouse monoclonal antibodies based on the antibody-humanization method originally developed by Queen et al. (1989, supra). The general protocol disclosed in Tsurushita is briefly summarized below.

5.3.1. General Protocol for Preparing Humanized Antibodies

Cloning and Sequencing of Mouse V Genes

Various methods are available for cloning cDNAs encoding the VH and VL regions of a target mouse monoclonal antibody. For example, 5' RACE (rapid amplification of cDNA ends) method using SMART RACE cDNA Amplification Kit (BD Biosciences, CA) or the GeneRacer Kit (Invitrogen, CA) has been commonly used. A gene-specific primer for 5' RACE can be prepared based on the isotypes of the H-chain and the L-chain of the target monoclonal antibody so that it can bind immediately downstream of the variable region for each of the H-chain and L-chain. Thus, 5' RACE primer may be designed to be specific for each subtype in mouse, such as γ1, γ2a, γ2b or γ3. Alternatively, a common primer for all subtypes may be designed based on the consensus or highly homologous region among the subtypes. In Tsurushita, the following 5' RACE primers are disclosed as examples:

```
(i) 5'-GCCAGTGGATAGACTGATGG-    (SEQ ID NO: 129)
```

(for cloning of mouse γ1, γ2a, γ2b and γ3 H-chains)

```
(ii)   5'-GATGGATACAGTTGGTGCAGC-   (SEQ ID NO: 130)
```

(for cloning of mouse κ light chains).

PCR-amplified V gene fragments can be directly cloned into a plasmid vector, for example, using the Zero Blunt TOPO PCR Cloning Kit (Invitrogen), and their DNA sequences determined. The obtained sequences should be confirmed by, for example, comparing their encoding amino acid sequences with those of the target monoclonal antibody determined by the N-terminal amino acid sequencing, using, for example a Model 241 Protein Sequencer (Hewlett-Packard, CA). Typically, the determination of at least 15-20 amino acid residues at the N-terminus of the target antibody, for example, by Edman degradation, is sufficient to confirm the authenticity of the cloned DNA sequences. Tsurushita cautions that when glutamine, which is one of the two most common N-terminal amino acid in mouse, is the N-terminal amino acid, it might have been converted to pyroglutamine and blocks the sequencing at the N-terminus. In that case, it is necessary to deblock the N-terminus to obtain the sequence.

Three-Dimensional Modeling of V Regions

Based on the sequences of the VH and VL regions, the framework residues of the target antibody that are potentially important for maintaining the conformational structure of the CDRs, are first identified by the method, for example, described by R. Levy et al., 1989, *Biochemistry* 28:7168-7175; and by B. Zilber et al., 1990, *Biochemistry* 29:10032-10041. Typically, each of the VH and VL regions is divided into 14 structurally meaningful segments, which are β strands and loop-like structures comprising the domain structure of the immunoglobulin superfamily. The amino acid sequence of each of the segments from the target antibody is aligned with the corresponding segments of antibodies of known structures, in the PDB database (see H. M. Berman et at, 2000, *Nucleic Acids Res.* 28:235-342). By multiple sequence alignment, a corresponding segment having the highest sequence homology to each of the target segment is selected and the three-dimensional model of the V-region is constructed. In order to optimize the structure, the model is subjected to multiple cycles of conjugate gradient energy minimization (e.g., using ENCAD, or as described by Press et al., 1990, in "*Numerical Recipes,* Cambridge University Press, Cambridge; AMBER by Weiner et al., 1981, *J. Comp. Chem.* 2:287-303; 3D-JIG-SAW available at BioMolecularModelling or "BMM" web site run by Cancer Research UK; or SWISS-MODEL available at ExPASy Proteomics Server web site run by Swiss Institute of Bioinformatics, Geneva).

Selection of Human Frameworks

In parallel with modeling the structure of the V regions, the amino acid sequences deduced from the cDNA cloning of the mouse VH and VL regions, respectively, are compared to human V region sequences in the databases, for example, the Kabat database (see Johnson et al., 2000, *Nucleic Acids Res.* 28:214-218.), GenBank, and so forth. Human framework regions that have overall sequence identity of at least about 65%, at least about 70%, at least about 75%, at least about 80%, at least about 85%, at least about 90%, or at least 95% identity, with the mouse sequence, can be searched using, for example, the Smith-Waterman algorithm (by Gusfield, 1997, in "*Algorithms on Strings, Trees, and Sequences*", Cambridge University Press, Cambridge), or BLAST (by Karlin et al., 1990, *Proc. Natl. Acad Sci. USA* 87:2264-2268), and the like. These human sequences may be based on cDNA-based and protein-derived sequences; however, the use of germline is often preferable as it may be useful in eliminating potential immunogenicity associated with somatic hypermutations in cDNA-based, protein-derived sequences. In the alternative, as described in Queen et al. (1989, supra), the use of a consensus framework sequence can also identify and remove such hypermutated residues in the framework obtained from cDNA-based or protein-derived sequences. In the case where a germline VH segment is used as an acceptor framework, VH segments encoded on chromosome 14, rather than 15 and 16, should be used as only those on chromosome 14 produce functional VH regions.

Design of Humanized V Regions

According to Queen et al. (1989, supra), it is necessary to identify framework amino acids within about 4-6 Å of the CDRs as these residues are considered to be potential key framework residues that support the correct CDR structures. Such a process can be achieved using a computer program, such as RASMOL available at Molecular Visualization Freeware web site supported by National Science Foundation (NSF), that calculates interatomic distances from the atomic coordinates or, through manual inspection of a computer model. If amino acids at key framework positions are different between mouse donor and human acceptor sequences, those of mouse donor usually replace the human residues. However, if such residues have minimal contribution to support the CDR structures, the corresponding human residues are typically used. Also, if the selected human acceptor contains "atypical" amino acids, which occur in less than about 10-20% of the V region sequences, they may be the result of somatic hypermutation during affinity maturation and should be replaced with the donor residues in order to avoid potential immunogenicity in humans.

In addition, other factors, such as residues of potential N-linked glycosylation signals, need to be carefully considered in order to design humanized V regions (see Tsurushita for details).

Humanized antibodies may contain a human constant region or a portion thereof from the human κ or λ light chain, and/or the γ1, γ2, γ3, γ4, μ, α1, α2, δ, or ε heavy chain of human antibodies, or variants thereof, depending on the effector functions required or to be eliminated for therapeutic uses. For example, a Fc portion of the constant region containing a mutation may be fused to the variable region of the chimeric or humanized antibody of the present invention so as to reduce the binding of the antibody to Fc receptors and/or to reduce its ability to fix complement (see, for example, Winter et al., GB 2,209,757 B; Morrison et al., WO 89/07142, Morgan et al., WO 94/29351). Such manipulations of antibody molecules can be carried out by recombinant DNA technology as described in Section 5.2.

Preferably the resulting chimeric or humanized antibody has the same specificity as the non-human donor antibody and an affinity similar to or at least about ⅓, at least about ½, or at least about ⅔, of that of the non-human donor antibody. In another aspect, the resulting chimeric or humanized antibody has an affinity constant of at least about $1\times10^7$ $M^{-1}$, preferably at least about $1\times10^8$ $M^{-1}$, and most preferably at least about $1\times10^9$ $M^{-1}$.

In addition to the general protocol described above, antibodies can be humanized using a variety of techniques known in the art including, for example, CDR-grafting (EP 239,400; PCT publication WO 91/09967; U.S. Pat. Nos. 5,225,539; 5,530,101 and 5,585,089), veneering or resurfacing (EP 592, 106; EP 519,596; Padlan, Molecular Immunology, 28(4/5): 489-498, 1991; Studnicka et al., Protein Engineering, 7(6): 805-814, 1994; Roguska et al., Proc Natl. Acad. Sci. USA, 91:969-973, 1994), and chain shuffling (U.S. Pat. No. 5,565, 332), all of which are hereby incorporated by reference in their entireties.

5.3.2. Additional Considerations for Preparing Humanized Antibodies as Pharmaceuticals To offer humanized antibodies as pharmaceuticals, an efficient and consistent production system therefor needs to be prepared. For example, an appropriate expression vector for humanized antibodies is prepared by inserting H- and L-chain sequences, and a high-productivity cell line transfected with the expression vector can be obtained as a seed cell for a master cell bank (MCB), which serves as a stable and semi-permanent source for a working cell bank (WCB). Humanized antibodies can be then prepared by culturing working cells from the WCB and collecting the culture medium.

Various expression vectors with appropriate regulatory genes can be used for the preparation of such a production cell line. As a host cell, those commonly used for expressing mammalian proteins can be used for the expression of humanized antibodies. Examples of such host cells include, but are not limited to, Chinese Hamster Ovary (CHO) cells, SP2/0-Ag14.19 cells, NSO cells, and the like. The productivity of humanized antibodies can be maximized by selecting the best combination of an expression vector and a host cell. Furthermore, the composition of culture media should be explored in order to select suitable media, from various serum-free culture media and supplements, so that the expression of humanized antibodies by the host cell can be optimized.

Based on the efficiency and the final yield, the humanized antibodies produced by the host cell can be purified from the culture supernatant using various methods well known in the art, including affinity chromatography, ion-exchange chromatography, hydrophobic interaction chromatography, and the like.

5.4. Pharmaceutical Composition and Therapeutic Uses

The present invention provides a pharmaceutical composition comprising the humanized antibody or an antigen-binding fragment thereof, described above, that immunospecifically recognizes human α9 integrin. The pharmaceutical composition comprising the humanized antibody of the present invention as an active ingredient can be used as an agent for preventing and/or treating a disorder or disease that is associated with α9 integrin, including, but not limited to, cancer, e.g., the growth or metastasis of cancer cells, and an inflammatory disease, e.g., rheumatoid arthritis, osteoarthritis, hepatitis, bronchial asthma, fibrosis, diabetes mellitus, arteriosclerosis, multiple sclerosis, granuloma, an inflammatory bowel disease (ulcerative colitis and Crohn's disease), an autoimmune disease, and the like.

The pharmaceutical composition comprising the humanized antibody of the present invention can also be used to treat chronic rejection after organ transplantation, and an autoimmune disease such as systemic autoimmune disease, erythematosus, uveitis, Behcet's disease, polymyositis, glomerular proliferative nephritis, sarcoidosis, and the like.

The preventive and/or therapeutic agent for preventing or treating the disorders or diseases described above, comprising the humanized antibody of the present invention, has low toxicity and can be administered to humans orally or parenterally, directly as a liquid preparation by mixing in a suitable solvent, or as a pharmaceutical composition in an appropriate dosage form.

The pharmaceutical composition used for the administration described above contains the aforesaid antibody or salts thereof and pharmaceutically acceptable carriers, diluents or excipients. Such a composition is provided in a dosage form suitable for oral or parenteral administration.

The dose may vary depending upon the age and the size of a subject to be administered, target disease, conditions, route of administration, and the like. When the antibody is used for preventing and/or treating, for example, rheumatoid arthritis in an adult patient, it is advantageous to intravenously administer the antibody of the present invention normally at a single dose of about 0.01 to about 20 mg/kg body weight, preferably about 0.1 to about 10 mg/kg body weight, and more preferably about 0.1 to about 5 mg/kg body weight, approximately 1 to 5 times per day, preferably approximately 1 to 3 times per day. In other parenteral administration and oral administration, the antibody can be administered in a dose corresponding to the dose given above. When the condition is especially severe, the dose may be increased according to the condition.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu and Wu, 1987, J. Biol. Chem. 262:4429 4432). Methods of introduction include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, by means of nasal spray, or by means of an implant, said implant being of a porous, non porous, or gelatinous material, including membranes, such as sialastic membranes, or fibers. In one embodiment, administration can be by direct injection at the site (or former site) infected tissues.

In another embodiment, the pharmaceutical composition can be delivered in a vesicle, in particular a liposome (see Langer, 1990, Science 249:1527-1533; Treat et al., in Liposomes in the Therapy of Infectious Disease and Cancer, Lopez Berestein and Fidler (eds.), Liss, New York, pp. 353-365 (1989); Lopez-Berestein, ibid., pp. 317-327; see generally ibid.).

In yet another embodiment, the pharmaceutical composition can be delivered in a controlled release system. In one embodiment, a pump may be used (see Langer, supra; Sefton, 1987, CRC Crit. Ref. Biomed. Eng. 14:201; Buchwald et al.,1980, Surgery 88:507; and Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. Macromol. Sci. Rev. Macromol. Chem. 23:61 (1983); see also Levy et al., 1985, Science 228:190; During et al., 1989, Ann. Neurol. 25:351; Howard et al., 1989, J. Neurosurg. 71:105). In yet another embodiment, a controlled release system can be placed in proximity of the composition's target, thus requiring only a fraction of the systemic dose (see, e.g., Goodson, in Medical Applications of Controlled Release, supra, vol. 2, pp. 115-138 (1984)). Other controlled release systems are discussed in the review by Langer (Science 249:1527-1533 (1990)).

Examples of the composition for oral administration include solid or liquid dosage forms, specifically, tablets (including dragees and film-coated tablets), pills, granules, powdery preparations, capsules (including soft capsules), syrup, emulsions, suspensions, etc. Such a composition is manufactured by publicly known methods and contains a vehicle, a diluent or an excipient conventionally used in the field of pharmaceutical preparations. Examples of the vehicle or excipient for tablets are lactose, starch, sucrose, magnesium stearate, and the like.

The injectable preparations may include dosage forms for intravenous, subcutaneous, intracutaneous and intramuscular injections, drip infusions, etc. These injectable preparations may be prepared by methods publicly known. The injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule. The suppository used for rectal administration may be prepared by blending the aforesaid antibody or its salt with conventional bases for suppositories.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to 500 mg per dosage form in a unit dose; especially in the form of injection, it is preferred that the aforesaid antibody is contained in about 5 to 100 mg and in about 10 to 250 mg for the other dosage forms.

Each composition described above may further contain other active components unless formulation causes any adverse interaction with the antibodies described above.

The present invention also relates to an inhibitor and/or promoter for cell and/or tissue remodeling, which comprises an α9 integrin-binding functional molecule (e.g., OPN, VCAM-1, tenascin-C, fibronectin, pp-vWF, tTG, etc.) as an active ingredient; and a method for inhibiting and/or promoting cell and/or tissue remodeling, which comprises contacting the α9 integrin-expressing cell and/or tissue (e.g., a tumor cell, neutrophil, smooth muscle, etc.) with the α9 integrin-binding functional molecule. The dose, method for administration, pharmaceutical preparation, etc. of the active ingredient in such a therapeutic agent can be appropriately determined by referring to the foregoing description of medicaments comprising the humanized antibodies of the present invention.

As described above, the present invention further provides a method for preventing or treating a disorder or disease that is associated with or involves α9 integrin, said method comprising administering an effective amount of at least one of the humanized antibodies of the present invention to a subject in need thereof 5.5. Diagnostic Uses The pharmaceutical composition comprising the humanized antibody of the present invention can be used as a diagnostic agent for cancer, e.g., the growth or metastasis of cancer cells, and an inflammatory disease, e.g., rheumatoid arthritis, osteoarthritis, hepatitis, bronchial asthma, fibrosis, diabetes mellitus, cancer metastasis, arteriosclerosis, multiple sclerosis, granuloma, etc., or as a diagnostic agent for chronic rejection after organ transplantation, an autoimmune disease such as systemic autoimmune disease, erythematosus, uveitis, Behcet's disease, polymyositis, glomerular proliferative nephritis, sarcoidosis, and so forth. The humanized antibodies of the present invention are capable of specifically recognizing the α9 integrin and hence can be used to quantify the α9 integrin in a test fluid, especially for quantification by the sandwich immunoassay, competitive assay, immunometry, nephrometry, etc., immunostaining, or the like. In applying these immunological methods to the assay methods of the present invention, it is not required to set forth any particular conditions, procedures, etc. It is sufficient to construct assay systems by adding ordinary technical consideration in the art to conventional conditions and procedures. For details of these general technical means, reference can be made to reviews, texts or the like.

As described above, the α9 integrin can be quantified with high sensitivity by using the antibodies of the present invention. The humanized antibodies of the present inventions are particularly useful for diagnosing various diseases associated with the α9 integrin by applying the method for quantifying the α9 integrin in vivo. For instance, where an increase or decrease in the expression level of the α9 integrin is detected, it can be diagnosed that it is highly likely that one now suffers from diseases associated with the α9 integrin, e.g., cancer or an inflammatory disease, or it is highly likely that one will suffer from these diseases in the future. Thus, the present invention also provides a method for diagnosing a disorder or disease associated with or involve α9 integrin in a subject, said method comprising administering an effective amount of at least one of the humanized antibodies of the present invention or both to a subject in need thereof. Required dosages for such an in vivo diagnosis may be less than those required for therapeutic uses and can be determined by one skilled in the art according to routine procedures.

The humanized antibodies of the present invention can also be used for specifically detecting the α9 integrin present in a test fluid such as a body fluid, a tissue, etc. The humanized antibodies can also be used for preparation of antibody columns for purification of the α9 integrin, for detection of the α9 integrin contained in each fraction upon purification or for analysis of behaviors of the α9 integrin in cells to be tested.

6. EXAMPLES

The following examples illustrate the preparation of monoclonal antibodies that immunospecifically recognize human and/or mouse α9 integrin, the sequencing of the variable regions of the monoclonal antibodies, the epitope mapping and other characterization of the antibodies and the chimerization and the humanization of such antibodies, as well as the characterization of the resulting chimeric and humanized antibodies. These examples should not be construed as limiting.

6.1. Preparation of Mouse Antibody Against Human α9 Integrin

Mouse monoclonal antibodies against human α9 integrin were prepared according to the subtractive immunization method (by Williams C. V., et al., 1992, *Biotechniques* 12:842-847). Briefly, three Balb/c mice were injected intraperitoneally with CHO-K1 cells at $4 \times 10^6$ per mouse. In the following two days, the mice received 4 mg/mouse of cyclophosphamide intraperitoneally. At two weeks after the cyclophosphamide injection, the mice were injected intraperitoneally with $2 \times 10^6$ cells/mouse of CHO-K1 cells expressing human α9 integrin (Human α9/CHO-K1 cells), followed by another intraperitoneal injection of the same cells at $3 \times 10^6$ cell/mouse two weeks later. Hybridomas were prepared by the methods well known in the art (see, for example, Harlow et al., Antibodies: A Laboratory Manual, (Cold Spring Harbor Laboratory Press, 2nd ed. 1988); Hammerling, et al., in: Monoclonal Antibodies and T-Cell Hybridomas, pp. 563-681 (Elsevier, N.Y., 1981). Hybridoma clones producing monoclonal antibodies that were immunospecifically reactive with Human α9/CHO-K1 cells but not with CHO K1 cells expressing human α4 integrin were established and five hybridoma clones (i.e., 1K11, 21C5, 24I11, 25B6 and 28S1) producing monoclonal antibodies immunospecifically recognizing human α9 integrin were isolated.

6.2. Epitope Analysis for Anti-Human α9 Integrin Monoclonal Antibodies

Twelve-residue polypeptides, starting from N-terminal of human α9 integrin and every three residues thereafter (i.e., amino acid residues 1-12, 4-15, 7-18, and so forth) were prepared and coupled to a cellulose membrane via C6-spacer and 2 βAla residues at 5 nmol/spot. The membrane was blocked with a blocking buffer (milk/0.05% Tween20 in PBS) and reacted with 10 ml of solution containing 1.0 μg/ml of each of the anti-human α9 integrin monoclonal antibodies (i.e., 1K11, 21C5, 24I11 and 25 B6, respectively) labeled with peroxidase for three hours at room temperature. After washing with T-TBS, the membrane was reacted with enhanced chemiluminescence (ECL) detecting reagent for 1 minute at room temperature. The luminescence emitted as a result of the enzymatic reaction is measured and epitopes of the antibodies were determined based on the luminescence intensities. As a control, Y9A2 (see Wang et al., 1996, *Am J Respir Cell Mol Biol* 15, 664-672), a commercially available monoclonal antibody against human α9 integrin, was used.

Table 1 below shows the result of the epitope mapping, which indicated that the monoclonal antibodies isolated by the present inventors have epitopes that are distinct from that of Y9A2.

TABLE 1

| Human α9 integrin sequences | 1K11 | 21C5 | 24I11 | 25B6 | Y9A2 |
|---|---|---|---|---|---|
| FQGPADSFFGYA (SEQ ID NO: 77) | − | − | − | ++ | − |
| KSPGAVFKCRVHTNPDRR (SEQ ID NO: 78) | ++ | +++ | ++++ | − | + |
| WMGVSLARQPKADGRVLA (SEQ ID NO: 79) | + | +++ | + | − | + |
| CAHRWKNIYYEADHI (SEQ ID NO: 80) | + | + | +++ | + | + |
| GFCYIIPSNLQAKGRTLI (SEQ ID NO: 81) | +++ | +++++ | +++++ | +++++ | +++++ |
| VMGAPGSFYWAGTIKVLN (SEQ ID NO: 82) | + | + | + | +++ | + |
| VIMNRRYTYLGYAVT (SEQ ID NO: 83) | +++++ | ++ | +++++ | +++++ | +++ |
| VYIFRADRRSGTLIKIFQ (SEQ ID NO: 84) | ++++ | +++++ | +++ | − | + |
| QYSMKLSGQKINPVLRMFGQSISG (SEQ ID NO: 85) | + | ++++ | − | − | + |
| VVLLRARPVITVDVSIFL (SEQ ID NO: 86) | ++ | ++ | − | − | +++++ |
| RHYVAHVKRRVQDVISPI (SEQ ID NO: 87) | +++ | +++ | +++++ | + | ++ |
| ELPPLTPVLRWKKGQKIAQKNQTVFERNCR (SEQ ID NO: 88) | + | +++++ | + | − | ++ |
| YLALGAVKNISL (SEQ ID NO: 89) | + | + | − | ++ | +++++ |
| CSVGFPFMRSKSKYEFSV (SEQ ID NO: 90) | + | ++ | ++ | − | +++ |
| SSSVIQFMSRAKVKVDPALRV (SEQ ID NO: 91) | + | ++ | +++ | − | + |

6.3. CDR Analysis of Anti-Human α9 Integrin Antibodies

The amino acid sequences of CDRs of the monoclonal antibodies (i.e., 1K11, 21 C5, 24I11, 25B6 and 28S1) were determined by reverse transcription of the mRNA extracted from the corresponding hybridomas to prepare cDNAs. Using the cDNAs as templates, the variable regions of the H-chains and L-chains were extended and amplified by PCR using ScFv-cloning primers (Light Primer Mix and Heavy Primer Mix; by Amersham Biosciences Corp., IL). The PCR products were cloned into pCRII TOPO vector, sequenced and the amino acid sequences were determined. This process was repeated three times for each antibody. The results are shown in Table 2.

stand at room temperature for 30 minutes and 20% acetic acid solution was added thereto to effect dissolution. The adhesion activity was quantified by measuring OD at 590 nm wavelength.

As shown in FIG. 16, the cell adhesion involving Tenascin-C was inhibited by 21C5, 24I11, 25B6 and 28S1, but not by 1K11. The cell adhesion involving fibronectin was inhibited by 21C5, 25B6 and 28S1 and by 24I11 to a less degree, but no inhibition was observed with 1K11. The cell adhesion involving VCAM-1 was inhibited by 21C5, 24I11, 25B6 and 28S1, but not by 1K11. Likewise, the cell adhesion involving hOPN(RAA)N-half was inhibited by 21C5, 24I11, 25B6 and 28S1, but not by 1K11.

TABLE 2

| CDRs | 1K11 | 21C5 | 24I11 | 25B6 | 28S1 |
|---|---|---|---|---|---|
| CDRH1 | DYNMD (SEQ ID NO: 32) | DYYMY (SEQ ID NO: 42) | DTYVH (SEQ ID NO: 4) | SYGVH (SEQ ID NO: 52) | GYGVN (SEQ ID NO: 62) |
| CDRH2 | DINPNNGGTIYNQKFQG (SEQ ID NO: 33) | TISDGGNYTYYPDSVKG (SEQ ID NO: 43) | NIDPANGNTKYDPKFQG (SEQ ID NO: 5) | VIWSGGSTNYNSALMS (SEQ ID NO: 53) | MIWGDGITEYNSALKS (SEQ ID NO: 63) |
| CDRH3 | SGVISTDY (SEQ ID NO: 34) | DRDGSSLFAY (SEQ ID NO: 44) | WLRHFYYAMDY (SEQ ID NO: 6) | DYGNYPWFAY (SEQ ID NO: 54) | RDASSGYGFA (SEQ ID NO: 64) |
| CDRL1 | RASQEISGYLI (SEQ ID NO: 37) | KASQDVNIAVA (SEQ ID NO: 47) | RASENIYYSLA (SEQ ID NO: 11) | KASQDVNTAVA (SEQ ID NO: 57) | TASSSVSSSYLH (SEQ ID NO: 67) |
| CDRL2 | AASTLDS (SEQ ID NO: 38) | WASTRHT (SEQ ID NO: 48) | NANSLED (SEQ ID NO: 12) | SASYRYT (SEQ ID NO: 58) | STSNLAS (SEQ ID NO: 68) |
| CDRL3 | LQYANYPPT (SEQ ID NO: 39) | QQHYNTPW (SEQ ID NO: 49) | KQAYDVPYT (SEQ ID NO: 13) | QQHYSTPCA (SEQ ID NO: 59) | HQYHRSPYT (SEQ ID NO: 69) |

6.4. Cell Adhesion Inhibitory Activity (1) Since it is known that cell adhesion involves the binding of α9 integrin to its ligands, i.e., various ECMs, including OPN, fibronectin, Tenascin-C, VCAM-1, and the like, the isolated anti-human α9 integrin antibodies were examined for their cell adhesion inhibitory activity.

Briefly, hOPN(RAA)N-half was prepared as a Glutathione S-transferase (GST)-fusion protein by isolating from *E. coli* host cells an N-terminal portion down to the thrombin-cleavage site of OPN, in which the GRD sequence has been replaced with the RAA sequence, and cleaving the GST portion with Precision protease (Amersham Biosciences). VCAM-1 was purchased from R&D Systems, Inc. (Minneapolis, Minn.). Tenascin-C and human fibronectin were prepared by synthesizing polypeptides containing AEIDGIEL (SEQ ID NO:92); the α9 integrin-binding region of Tenascin-C) and CPEDGIHELFP (SEQ ID NO:93); the α9 integrin-binding region of human fibronectin), respectively, and subsequently attaching them to bovine serum albumin (BSA). For human α9 integrin, CHO-K1 cells that abundantly expressed human α9 integrin (Human α9/CHO-K1) were used.

Fifty microliters of Tenascin-C, fibronectin, VCAM-1 or hOPN(RAA)N-half were added to a 96-well plate at 1.25-5.0 μg/ml and incubated at 37° C. for 1 hour to coat the plate. After blocking the plate with a blocking solution (0.5% BSA/PBS) and washing it with PBS once, the mixture of human α9/CHO-K1 cells ($1.0 \times 10^5$ cells/ml) and the isolated monoclonal antibodies (10 g/ml in 0.25% BSA-Minimum Essential Media (MEM) was added to the plate at 200 μl/well and incubated at 37° C. for 1 hour under 5% $CO_2$. Non-adherent cells were rinsed off with PBS and adherent cells were fixed and stained with 0.5% Crystal Violet (by WAKO, Osaka, Japan)/20% methanol. The stained cells were allowed to (2) Since α4 integrin and α9 integrin have many common ECM ligands, the presence of both anti-α4 integrin and anti-α9 integrin antibodies is expected to enhance the cell adhesion inhibitory activity. Thus, the effect of the both types of antibodies in combination was examined in vitro for a possible inhibitory effect on metastatic cancer, based on the cell adhesion between human melanoma cells (G361) expressing α4 integrin as well as α9 integrin and VCAM-1 (1.25 μg/ml) as an ECM; a rat monoclonal antibody, P1H4 (Cat. No. MAB16983Z, Chemicon International Inc., CA) was used as an anti-human α4 integrin antibody.

As shown in FIG. 17, the adhesion involving VCAM-1 was not inhibited by any of the anti-human α9 integrin antibodies alone, but was inhibited by the positive control (Y9A2), 21C5 and 24I11, in the co-presence of the anti-human α4 integrin antibody. Since cells expressing many α9 integrin molecules usually express α4 integrin molecules also, this result indicates that the inhibition of cell adhesion can be effectively achieved by the combination use of anti-human α9 integrin antibody and anti-human α4 integrin antibody, thereby enhancing the suppression of various disorders and diseases, including metastatic cancer involving these integrin molecules.

6.5. Use of Anti-Human α9 Integrin Antibodies in FACS Analysis

Whether the anti-human α9 integrin antibodies were usable for FACS was examined using Human α9/CHO-K1 cells, CHO-K1 cells and human neutrophils endogenously expressing the α9 integrin. In human neutrophils, FACS analysis was conducted at the cell count of $1.0 \times 10^5$ and antibodies were reacted on ice. Non-specific reaction with the Fc receptor was blocked with 50% goat serum. FITC-labeled anti-mouse IgG antibody was used as a secondary antibody. As a result (see FIGS. 20*a*, 20*b* and 20*c*), all of the anti-human α9 integrin antibodies could detect the α9 integrin on Human α9/CHO-K1 and human neutrophils. None of the antibodies reacted with Human α4/CHO-K1 cells (see FIGS. 20a, 20b and 20c). These results revealed that all of the anti-human α9 integrin antibodies could detect the human α9 integrin proteins expressed on cells using FACS.

6.6. Therapeutic Effects of Anti-α9 Integrin Antibody

Therapeutic effects of anti-α9 integrin antibodies were examined in a mouse system.

The anti-mouse α9 integrin monoclonal antibodies (11L2B, 12C4'58, 18R18D and 55A2C) were prepared substantially in the same manner as described for mouse anti-human α9 integrin antibodies (see Section 6.1, supra), except that hamsters were immunized with CHO-K1 cells expressing mouse α9 integrin (mouse α9/CHO-K1 cells) and the resulting monoclonal antibodies that reacted with mouse α9/NIH3T3 cells but not with mouse α4/NIH3T3 were selected.

6.6.1. Therapeutic Effect on Hepatitis

WO 02/081522 discloses that hepatitis can be treated by inhibiting the OPN functions. Accordingly, therapeutic effects of anti-α9 integrin antibody was studied in a mouse hepatitis model using a hamster anti-mouse α9 integrin antibody, 11L2B, and a rat anti-mouse α4 integrin antibody, R1-2 (Pharmingen). The blood AST and ALT levels in the mice were measured using GPT/ALT-PIII and GOT/AST-PIII (Fuji Film), 12 hours after an intravenous injection of 200 µg of concanavalin A (Con A) (Vector). Three hours before the Con A injection, 200 µg of the antibody were administered. As shown in FIG. 18, the AST and ALT levels were found to be decreased by the anti-α9 integrin antibody, and the therapeutic effects could be noted. In addition, the therapeutic effects could be boosted by concomitant use with the anti-α4 integrin antibody. The results revealed that hepatitis could be treated by the anti-α9 integrin antibody.

6.6.2. Effect of Anti-α9 Integrin Antibodies on Growth of Mouse Cancer Cell Line Murine melanoma cell line B16-BL6 expresses abundant α9 integrin. Accordingly, cell growth inhibitory activities of the established anti-mouse α9 integrin antibodies against cancer cells were examined.

The B16-BL6 cells were prepared on a 96-well plate for cell culture (Becton Dickinson) at $5 \times 10^4$ cells/mL in 10% FCS/DMEM. After 10 µg/ml of the anti-mouse α9 integrin antibody and anti-mouse α4 integrin antibody were added, 100 µL each of the cell-antibody suspension was added to each well. Incubation was conducted at 37° C. for 24 hours under 5% $CO_2$, and 10 µL each of Cell Counting Kit 8 (Dojin Kagaku Kenkyu-sho) was added, followed by incubation at 37° C. for an hour under 5% $CO_2$. Absorbance at O.D. 450 was measured and the cell count was quantitatively analyzed. As shown in FIG. 19, 12C4'58 gave the highest inhibitory activity and inhibited the growth of B16-BL6 cells by about 35%. Both 55A2C and R1-2 could inhibit the growth by about 20%.

Next, for analysis of inhibitory effects against cell growth under conditions closer to the in vivo conditions, VCAM-1 was immobilized on a solid phase and assayed in a similar fashion. VCAM-1 is a ligand for α9 integrin and a recombinant soluble form of VCAM-1 protein, rhVCAM-1-Fc chimera (Roche), was used. Using the rhVCAM-1-Fc chimera immobilized on a solid phase with 10 µg/mL, non-specific reaction was blocked with 0.5% BSA/PBS. The chimera was added in a concentration of 10 pg/ml in single use of the antibody, and in 5 µg each/ml in concomitant use. Thereafter, the same procedures as in FIG. 19 were followed. As a result, the effect was not obtained at all or only an imperceptible effect was obtained by single administration of 12C4'58 and by single use of the α4 inhibitory antibody clone R1-2, whereas in simultaneous administration of 12C4'58 with R1-2 the cell growth inhibitory effect showed a marked increase by about 20%, as shown in FIG. 21.

6.6.3. Therapeutic Effect of Anti-α9 Integrin in Mouse Rheumatoid Arthritis Model Seven-week old female mice (Balb/c) (3 mice per group) were injected intraperitoneally with the hamster anti-mouse α9 integrin antibody (55A2C), or normal hamster IgG (NHG) at 400 µg/mouse. After 24 hours, 2 mg/mouse of the arthritis-inducing cocktail of type II collagen-specific monoclonal antibody (Chondrex Inc.) was injected intravenously. After 72 hours, 400 µg/mouse of 55A2C or NHG as well as 50 µg./mouse of LPS were injected intraperitoneally. The mice were observed from 3 days before the LPS injection until 6 days after the LPS injection and the levels of arthritis were scored according to the method by Wood et al. (1969, *Int. Arch. Allergy Appl. Immunol.* 35:456). The result is shown in FIG. 22. The mice injected with control NHG had a high score and developed rheumatoid arthritis, whereas in those injected with anti-mouse α9 integrin antibody, the development of rheumatoid arthritis was completely blocked. Thus, anti-α9 integrin antibodies were indicated to have prophylactic and therapeutic effects on rheumatoid arthritis.

6.7. Humanization of Non-Human Antibodies

6.7.1. Cloning and Sequencing of Mouse 24I11 V Genes

Mouse 24I11 hybridoma cells were grown in TIL Media I (Immuno-Biological Laboratories, Gunma, Japan) containing 10% fetal bovine serum (FBS; HyClone, Logan, Utah) at 37° C. in a 7.5% $CO_2$ incubator. Total RNA was extracted from approximately $3 \times 10^6$ hybridoma cells using TRIzol reagent (Invitrogen, Carlsbad, Calif.) according to the supplier's protocol. Oligo dT-primed cDNA was synthesized using the GeneRacer Kit (Invitrogen) following the supplier's protocol. The variable region cDNAs for 24I11 heavy and light chains were amplified by polymerase chain reaction (PCR) with Phusion DNA polymerase (New England Biolabs, Beverly, Mass.) using primers that anneal respectively to the mouse gamma-1 and kappa chain constant regions, and a GeneRacer 5' primer (5'-CGACTGGAGCACGAGGA-CACTGA-) (SEQ ID NO:94) provided in the GeneRacer Kit. For PCR amplification of heavy chain variable region (VH), the primer has the sequence 5'-GCCAGTGGATAGACA-GATGG-(SEQ ID NO:95). For PCR amplification of light chain variable region (VL), the primer has the sequence 5'-GATGGATACAGTTGGTGCAGC-(SEQ ID NO:96). The amplified VH and VL cDNAs were subcloned into the pCR4Blunt-TOPO vector (Invitrogen) for sequence determination. DNA sequencing of the variable regions was carried out at Tocore (Menlo Park, Calif.). Several heavy and light chain clones were sequenced and unique sequences homologous to typical mouse heavy and light chain variable regions were identified. The consensus cDNA sequences along with deduced amino acid sequences of 24I11 VH and VL are shown in FIGS. 1 and 2, respectively.

6.7.2. Construction of Chimeric 24I11 IgG1/κ Antibody

Figure 5:
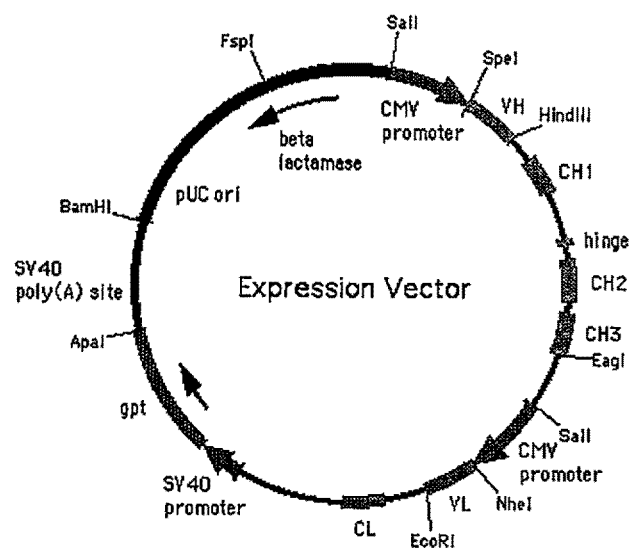

A gene encoding 24I11 VH was generated as an exon including a splice donor signal and appropriate flanking restriction enzyme sites by PCR using 24I11 VH cDNA as a template, 5'-GGG<u>ACTAGT</u>ACCACCATGAAA-TGCAGCTGGGTTATCTTC-(SEQ ID NO:97) (SpeI site is underlined) as a 5' primer, and 5'-GGG<u>AAGCTT</u>AGAGGCCATTCTTACCTGAGGAGACGGT-GACTGAGGTTC C-(SEQ ID NO:98) (HindIII site is underlined) as a primer (FIG. 3). Likewise, a gene encoding 24I11 VL was generated as an exon including a splice donor signal and appropriate flanking restriction enzyme sites by PCR using 24I11 VL cDNA as a template, 5'-GGG<u>GCTAGC</u>ACCACCATGAGTGTGCCCACTCAACT-CCTG-(SEQ ID NO:99) (NheI site is underlined) as a 5' primer, and 5'-GGG<u>GAATTC</u>TGAGAAGAC-TACTTACGTTTTATTTCCAGCTTGGTCCCCCC-(SEQ ID NO:100) (EcoRI site is underlined) as a primer (FIG. 4). The splice donor signals of the 24I11 VH and VL exons were derived from the mouse germline JH4 and Jκ2 sequences, respectively. PCR-amplified fragments were gel-purified using QIAquick Gel Extraction Kit (Qiagen, Valencia, Calif.), digested with SpeI and HindIII (for VH) or NheI and EcoRI (for VL), and cloned into a mammalian expression vector carrying human gamma-1 and kappa constant regions for production of chimeric 24I11 IgG1/κ antibody. The schematic structure of the resulting expression vector, pCh24I11, is shown in FIG. 5.

6.7.3. Generation of Humanized 24I11 V Genes

Humanization of the 24I11 variable regions was carried out as outlined by Queen et al. (Proc. Natl. Acad. Sci. USA 86: 10029-10033, 1989). First, a molecular model of the 24I11 variable regions was constructed with the aid of computer programs. Next, based on a homology search against human variable region sequences, the human amino acid sequence encoded by the nucleotide sequence of GenBank Accession No. X65891, which has a high homology [72.4% (63/87) amino acid identity in the FRHs] to 24I11 VH, was chosen as an acceptor to provide the frameworks for humanized 24I11 VH. Likewise, the human amino acid sequence encoded by the nucleotide sequence of GenBank Accession No. X72441 [77.5% (62/80) amino acid identity in the FRLs] was chosen as an acceptor for humanization of 24I11 VL.

At framework positions where the computer model suggested significant contact with the complementarity determining regions (CDRs), the amino acids from the 24I11 variable regions were substituted for the human framework amino acids. This was done at positions 27, 28, 29, 30, 48, 66, 67 and 71 (according to Kabat numbering system; see, Kabat et al., Sequences of Proteins of Immunological Interests, Fifth edition, NIH Publication No. 91-3242, U.S. Department of Health and Human Services, 1991) to generate humanized 24I11 (Hu24I11) VH (FIG. 6). For the light chain, replacements were made at residues 70 and 71 to generate humanized 24I11 (Hu24I11) VL (FIG. 7). The alignments of 24I11, designed Hu24I11, and the human acceptor amino acid sequence are shown for VH in FIG. 6 and for VL in FIG. 7.

A gene encoding each of Hu24I11 VH and VL was designed as an exon including a signal peptide, a splice donor signal, and appropriate restriction enzyme sites for subsequent cloning into a mammalian expression vector. The splice donor signals of the Hu24I11 VH and VL exons were derived from the human germline JH4 and Jκ1 sequences, respectively. The signal peptide sequences in the Hu24I11 VH and VL exons were derived from the corresponding mouse 24I11 VH and VL sequences, respectively. The Hu24I11 VH and VL genes were constructed by extension and PCR amplification of several overlapping synthetic oligonucleotide primers using ThermalAce DNA polymerase (Invitrogen) as outlined by He et al. (J. Immunol. 160: 1029-1035, 1998). The oligonucleotides used for construction of Hu24I11 VH and VL genes are listed in FIGS. 8 and 9, respectively. The location of the oligonucleotides in the Hu24I11 VH and VL genes is shown in FIGS. 10 and 11, respectively. PCR-amplified fragments were gel-purified using QIAquick Gel Extraction Kit (Qiagen) and cloned into pCR4Blunt-TOPO vector for sequence determination. After digestion with SpeI and HindIII (for VH) or NheI and EcoRI (for VL), Hu24I11 VH and VL genes were subcloned into corresponding sites in a mammalian expression vector for production in the human IgG1/κ form. The schematic structure of the resulting expression vector, pHu24I11, is shown in FIG. 5. The nucleotide sequences of the obtained Hu24I11 VH and VL genes along with deduced amino acid sequences are shown in FIGS. 12 and 13, respectively.

6.7.4. Transient Expression of Chimeric and Humanized 24I11 IgG1/κ

Chimeric and humanized 24I11 IgG1/κ antibodies were transiently expressed by transfecting pCh24I11 and pHu24I11 plasmid DNA, respectively, to HEK293 cells using polyethylenimine according to Durocher et al. (Nucl. Acids Res. 30: e9, 2002). Transiently transfected HEK293 cells were maintained for four days in DMEM containing 10% FBS at 37° C. in a 7.5% $CO_2$ incubator. The expression level of each of Ch24I11 and Hu24I11 1gG1/κ antibodies in culture supernatant was measured by sandwich ELISA. An ELISA plate was coated overnight at 4° C. with 100 μl/well of 1/2,000-diluted goat anti-human IgG Fcγ-chain-specific polyclonal antibodies (SouthernBiotech, Birmingham, Ala.) in PBS, washed with Wash Buffer (PBS containing 0.05% Tween 20), and blocked for 1 hr at room temperature with 300 μl/well of Blocking Buffer (PBS containing 2% Skim Milk and 0.05% Tween 20). After washing with Wash Buffer, 100 μl/well of samples appropriately diluted in ELISA Buffer (PBS containing 1% Skim Milk and 0.025% Tween 20) were applied to the ELISA plate. Human IgG1/κ antibody purified from human myeloma serum (SouthernBiotech) was used as a standard. After incubating the ELISA plate for 2 hr at room temperature and washing with Wash Buffer, bound antibodies were detected using 100 μl/well of 1/2,000-diluted horse radish peroxidase (HRP)-conjugated goat anti-human kappa chain polyclonal antibodies (SouthernBiotech). After incubating for 1 hr at room temperature and washing with Wash Buffer, color development was performed by adding 100 μl/well of ABTS substrate (bioWORLD, Dublin, Ohio). Color development was stopped by adding 100 μl/well of 2% oxalic acid. Absorbance was read at 405 nm.

6.7.5. Characterization of Humanized 24I11

Binding of chimeric and humanized 24I11 antibodies to human α9 integrin was examined by cell ELISA. CHO-K1 stable transfectants expressing recombinant human α9 integrin on the surface (CHO/huα9; provided by Gene Techno Science) were seeded at $2 \times 10^5$ cells/well in 50 μl of F12/DMEM (HyClone) containing 10% FBS in a 96-well tissue culture plate and grown overnight at 37° C. in a 7.5% $CO_2$ incubator. For testing of binding to human α9 integrin, 50 μl of chimeric 24I11, humanized 24I11 or irrelevant human IgG1/κ myeloma antibody (SouthernBiotech) in F12/DMEM containing 10% FBS was added to each well. After incubating for 1 hr at 4° C. and washing cells twice with ice-cold PBS, 100 μl of 1/1,000-diluted HRP-conjugated goat anti-human IgG polyclonal antibodies (SouthernBiotech) was added to each well. After incubating for 1 hr at 4° C., cells were washed three times with ice-cold PBS. For color development, 100 μl of ABTS substrate was added. Color development was stopped by adding 100 μl of 2% oxalic acid. Absorbance was read at 405 nm. The result showed that the binding of chimeric 24I11 antibody to human α9 integrin was almost same as that of humanized 24I11 antibody at both 0.5 and 1 μg/ml (FIG. 14).

Antigen binding of mouse, chimeric and humanized 24I11 monoclonal antibodies was also examined in a FACS binding assay using CHO/huα9 cells. Purified mouse 24I11 monoclonal antibody was provided by Gene Techno Sciences. Approximately $8 \times 10^5$ CHO/huα9 cells/test were washed with FACS Binding Buffer (PBS containing 0.5% BSA and 0.05% $NaN_3$) and suspended in 200 μl of FACS Binding Buffer containing various amounts of test antibody. After 30 min on ice, the cells were washed twice with FACS Binding Buffer. The cells stained with mouse 24I11 were then suspended in 200 μl of 1/200-diluted FITC-labeled goat anti-mouse IgG polyclonal antibody (SouthernBiotech) in FACS Binding Buffer. The cells stained with chimeric or humanized 24I11 were suspended in 200 μl of 1/200-diluted FITC-labeled goat anti-human IgG polyclonal antibody (SouthernBiotech) in FACS Binding Buffer. After 30 min on ice, the cells were washed with FACS Binding Buffer, suspended in 200 μl of FACS Binding Buffer, and analyzed using a FACScan flow cytometer (BD Biosciences, Franklin Lakes, N.J.). The binding of chimeric and humanized 24I11 antibodies to CHO/huα9 cells was very similar to each other in this analysis (FIG. 15).

The results of the cell ELISA and FACS experiments using transiently expressed antibodies suggest that humanization of mouse 24I11 antibody is successful.

Humanization of the other mouse anti-human α9 antibodies disclosed herein (i.e., 1K11, 21C5, 25B6 and 28S1) can be also carried out by employing the same procedure described herein. The DNA sequences and the amino acid sequences of the VH and VL regions, respectively, of these mouse monoclonal antibodies are summarized below.

| Mouse monoclonal antibodies | DNA sequence of VH region (SEQ ID NO:)[1] | Deduced amino acid sequence of mature VH (SEQ ID NO:)[2] | DNA sequence of VL region (SEQ ID NO:)[1] | Deduced amino acid sequence of mature VL (SEQ ID NO:) |
|---|---|---|---|---|
| 1K11 | 35 | 36 | 40 | 41 |
| 21C5 | 45 | 46 | 50 | 51 |
| 25B6 | 55 | 56 | 60 | 61 |
| 28S1 | 65 | 66 | 70 | 71 |

[1]The V genes of each antibody were cloned by a method using Amersham's degenerate primers.
[2]The deduced amino acid sequence starts from the 2nd residue of VH region (according to the Kabat numbering system) for each clone.

7. DEPOSITION

The hybridomas designated herein as 1K11, 21C5, 24I11, 25B6 and 28S1 producing mouse anti-human α9 integrin monoclonal antibodies were deposited on Feb. 15, 2006 with International Patent Organism Depositary, National Institute of Advanced Industrial Science and Technology, located at AIST Tsukuba Central 6, 1-1, Higashi 1-chome Tsukuba-shi, Ibaraki-ken 305-8566 Japan in accordance with the Budapest Treaty on the Deposit of Microorganisms, and accorded Accession Nos. FERM BP-10510, FERM BP-10511, FERM BP-10512, FERM BP-10513 and FERM BP-10832, respectively, all of which are incorporated herein by reference in their entireties.

8. Industrial Applicability

The humanized monoclonal antibodies of the present invention inhibit the function of α9 integrin to exhibit therapeutic effects on cancer, e.g., the growth or metastasis of cancer cells, and an inflammatory disease, e.g., rheumatoid arthritis, osteoarthritis, hepatitis, bronchial asthma, fibrosis, diabetes mellitus, cancer metastasis, arteriosclerosis, multiple sclerosis, granuloma, an inflammatory bowel disease (ulcerative colitis and Crohn's disease), an autoimmune disease, and the like. The pharmaceutical composition comprising both the anti-α9 integrin antibody and anti-α4 integrin antibody of the present invention exerts more improved therapeutic effects on cancer and an inflammatory disease.

9. List of Sequences

The sequences referenced throughout the specification are summarized below.

| SEQ ID NO. | TYPE | DESCRIPTION | SEQUENCE |
|---|---|---|---|
| 1 | AA | OPN adhesion sequence | GRGDS |
| 2 | AA | HuOPN's α4β1/α9β1-binding site | SVVYGLR |
| 3 | AA | MuOPN's α4β1/α9β1-binding site | SLAYGLR |
| 4 | AA | CDRH1 of 24I11 (FERM BP-10512) | DTYVH |
| 5 | AA | CDRH2 of 24I11 (FERM BP-10512) | NIDPANGNTKYDPKFQG |
| 6 | AA | CDRH3 of 24I11 (FERM BP-10512) | WLRHFYYAMDY |
| 7 | DNA | VH of 24I11 (FERM BP-10512) including sequence encoding signal peptide (1-57) | ATGAAATGCAGCTGGGTTATCTTCTTCCTGATG GCAGTGGTTACAGGGGTCAATTCAGAGGTTCA GCTGCAGCAGTCTGGGGCAGAGCTTGTGAAG CCAGGGGCCTCAGTCAAGTTGTCCTGCACAG CTTCTGGCTTCAACATTAAAGACACCTATGTG CACTGGGTGAAGCAGAGGCCTGAACAGGGCC TGGAGTGGATTGGAAATATTGATCCTGCGAAT GGTAATACTAAATATGACCCGAAGTTCCAGGG CAAGGCCACTATAACAGCAGACACATCCTCCA ACACAGCCTACCTGCACCTCAGCAGCCTGACA TCTGAGGACACTGCCGTCTATTACTGTGCTAG ATGGTTACGACATTTTTACTATGCTATGGACTA CTGGGGTCAAGGAACCTCAGTCACCGTCTCCT CA |

| SEQ ID NO. | TYPE | DESCRIPTION | SEQUENCE |
|---|---|---|---|
| 8 | AA | VH of 24I11 (FERM BP-10512) including signal peptide (1-19) | MKCSWVIFFLMAVVTGVNSEVQLQQSGAELVKP GASVKLSCTASGFNIKDTYVHWVKQRPEQGLE WIGNIDPANGNTKYDPKFQGKATITADTSSNTAY LHLSSLTSEDTAVYYCARWLRHFYYAMDYWGQ GTSVTVSS |
| 9 | AA | Mature VH of 24I11 (FERM BP-10512) | EVQLQQSGAELVKPGASVKLSCTASGFNIKDTY VHWVKQRPEQGLEWIGNIDPANGNTKYDPKFQ GKATITADTSSNTAYLHLSSLTSEDTAVYYCARW LRHFYYAMDYWGQGTSVTVSS |
| 10 | AA | Signal peptide of 24I11 H-chain | MKCSWVIFFLMAVVTGVNS |
| 11 | AA | CDRL1 of 24I11 (FERM BP-10512) | RASENIYYSLA |
| 12 | AA | CDRL2 of 24I11 (FERM BP-10512) | NANSLED |
| 13 | AA | CDRL3 of 24I11 (FERM BP-10512) | KQAYDVPYT |
| 14 | DNA | VL of 24I11 (FERM BP-10512) including sequence encoding signal peptide (1-60) | ATGAGTGTGCCCACTCAACTCCTGGGGTTGCT GCTGCTGTGGCTTACAGACGCAGGATGTGACA TCCAGATGACTCAGTCTCCAGCCTCCCTGGCT GCATCTGTGGGAGAAACTGTCACCGACATCCA GATGACTCAGTCTCCAGCCTCCCTGGCTGCAT CTGTGGGAGAAACTGTCACCGGGAAATCTCCT CAGCTCCTGATCTATAATGCAAACAGCTTGGA AGATGGTGTCCCATCGAGGTTCAGTGGCAGTG GATCTGGGACACAGTATTCTATGAAGATCAAC AGCATGCAGCCTGAAGATACCGCAACTTATTT CTGTAAACAGGCTTATGACGTTCCGTACACGT TCGGAGGGGGGACCAAGCTGGAAATAAAA |
| 15 | AA | VL of 24I11 (FERM BP-10512) including signal peptide (1-20) | MSVPTQLLGLLLLWLTDAGCDIQMTQSPASLAAS VGETVTITCRASENIYYSLAWYQQKQGKSPQLL IYNANSLEDGVPSRFSGSGSGTQYSMKINSMQP EDTATYFCKQAYDVPYTFGGGTKLEIK |
| 16 | AA | Mature VL of 24I11 (FERM BP-10512) | DIQMTQSPASLAASVGETVTITCRASENIYYSLA WYQQKQGKSPQLLIYNANSLEDGVPSRFSGSGS GTQYSMKINSMQPEDTATYFCKQAYDVPYTFG GGTKLEIK |
| 17 | AA | Signal peptide of 24I11 L-chain | MSVPTQLLGLLLLWLTDAGC |
| 18 | DNA | X65891 | ATGGACTGGACCTGGAGGGTCCTCTTTTTGGT GGCAGCAGCCACAGGTGCCCACTCCCAGGTC CAGCTTGTGCAGTCTGGGGCTGAGGTGAAGA AGCCTGGGGCCTCAGTGAAGGTTTCCTGCAA GGCTTCTGGATACACCTTCACTAGCTATGCTAT GCATTGGGTGCGCCAGGCCCCCGGACAAAGG CTTGAGTGGATGGGATGGATCAACGCTGGCAA TGGTAACACAAAATATTCACAGAAGTTCCAGG GCAGAGTCACCATTACCAGGGACACATCCGCG AGCACAGCCTACATGGAGCTGAGCAGCCTGA GATCTGAAGACACGGCTGTGTATTACTGTGCG AGAATACCCCGTATTAGCAGTGGCTGGTTGGG GGACTACTTTGACTACTGGGGCCAGGGAACCC TGGTCACCGTCTCCTCA |
| 19 | AA | FRH1 of X65891 | QVQLVQSGAEVKKPGASVKVSCKASGYTFT |

-continued

| SEQ ID NO. | TYPE | DESCRIPTION | SEQUENCE |
|---|---|---|---|
| 20 | AA | FRH2 of X65891 | WVRQAPGQRLEWMG |
| 21 | AA | FRH3 of X65891 | RVTITRDTSASTAYMELSSLRSEDTAVYYCAR |
| 22 | AA | FRH4 of X65891 | WGQGTLVTVSS |
| 23 | DNA | X72441 | CGCTCAGCTCCTGGGGCTCCTGCTACTCTGGCTCCGAGGTGCCAGATGTGACATCCAGATGACCCAGTCTCCATCCTCCCTGTCTGCATCTGTAGGAGACAGAGTCACCATCACTTGCCGGGCAAGTCAGAGCATTAGCAGCTATTTAAATTGGTATCAGCAGAAACCAGGGAAAGCCCCTAAGCTCCTGATCTATGCTGCATCCAGTTTGCAAAGTGGGGTCCCATCAAGGTTCAGTGGCAGTGGATCTGGGACAGATTTCACTCTCACCATCAGCAGTCTGCAACCTGAAGATTTTGCAACTTACTACTGTCAACAGAGTTACAGTACCCCTCGGACGTTCGGCCAAGGGACCAAGGTGGAAATCAAA |
| 24 | AA | FRL1 of X72441 | DIQMTQSPSSLSASVGDRVTITC |
| 25 | AA | FRL2 of X72441 | WYQQKPGKAPKLLIY |
| 26 | AA | FRL3 of X72441 | GVPSRFSGSGSGTDFTLTISSLQPEDFATYYC |
| 27 | AA | FRL4 of X72441 | FGQGTKVEIK |
| 28 | DNA | VH of Hu24I11 | CAGGTTCAGCTGGTGCAGTCTGGGGCAGAGGTGAAGAAGCCAGGGGCCTCAGTCAAGGTTTCCTGCAAGGCTTCTGGCTTCAACATTAAAGACACCTATGTGCACTGGGTGCGCCAGGCCCCTGGACAGAGGCTGGAGTGGATTGGAAATATTGATCCTGCGAATGGTAATACTAAATATGACCCGAAGTTCCAGGGCAAGGCCACTATAACAGCAGACACATCCGCGAGCACAGCCTACATGGAGCTCAGCAGCCTGAGATCTGAGGACACTGCCGTCTATTACTGTGCTAGATGGTTACGACATTTTTACTATGCTATGGACTACTGGGGTCAAGGAACCCTGGTCACCGTCTCCTCA |
| 29 | AA | VH of Hu24I11 | QVQLVQSGAEVKKPGASVKVSCKASGFNIKDTYVHWVRQAPGQRLEWIGNIDPANGNTKYDPKFQGKATITADTSASTAYMELSSLRSEDTAVYYCARWLRHFYYAMDYWGQGTLVTVSS |
| 30 | DNA | VL of Hu24I11 | GACATCCAGATGACTCAGTCTCCATCCTCCCTGTCTGCATCTGTGGGAGACAGAGTCACCATCACATGTCGAGCAAGTGAGAACATTTACTACAGTTTAGCATGGTATCAGCAGAAGCCAGGGAAAGCCCCTAAGCTCCTGATCTATAATGCAAACAGCTTGGAAGATGGTGTCCCATCGAGGTTCAGTGGCAGTGGATCTGGGACACAGTATACTCTCACCATCAGCAGCCTGCAGCCTGAAGATTTTGCAACTTATTACTGTAAACAGGCTTATGACGTTCCGTACACGTTCGGACAAGGGACCAAGGTGGAAATCAA |
| 31 | AA | VL of Hu24I11 | DIQMTQSPSSLSASVGDRVTITCRASENIYYSLAWYQQKPGKAPKLLIYNANSLEDGVPSRFSGSGSGTQYTLTISSLQPEDFATYYCKQAYDVPYTFGQGTKVEIK |
| 32 | AA | CDRH1 of 1K11 (FERM BP-10510) | DYNMD |
| 33 | AA | CDRH2 of 1K11 (FERM BP-10510) | DINPNNGGTIYNQKFQG |

| SEQ ID NO. | TYPE | DESCRIPTION | SEQUENCE |
|---|---|---|---|
| 34 | AA | CDRH3 of 1K11 (FERM BP-10510) | SGVISTDY |
| 35 | DNA | VH of 1K11 (FERM BP-10510) | GTGCAGCTGCAGGAGTCAGGACCTGAGCTGG TGAAGCCTGGGGCTTCAGTGAAGATACCCTGC AAGGCTTCTGGATACACATTCACTGACTACAA CATGGACTGGGTGAAGCAGAGCCATGGAAAG AGCCTTGAGTGGATTGGAGATATTAATCCTAAC AACGGTGGTACAATCTACAACCAGAAGTTCCA GGGCAAGGCCACATTGACTGTAGACAAGTCC TCCAGCACAGCCTACATGGAGCTCCGCAGCCT GACATCTGAGGACACTGCAGTCTATTACTGTG CAAGATCGGGGGTTATTAGTACGGACTACTGG GGCCAAGGGACCACGGTCACCGTCTCCTCA |
| 36 | AA | Mature VH of 1K11 (FERM BP-10510) starting from 2nd residue according to Kabat numbering | ?VQLQESGPELVKPGASVKIPCKASGYTFTDYN MDWVKQSHGKSLEWIGDINPNNGGTIYNQKFQ GKATLTVDKSSSTAYMELRSLTSEDTAVYYCARS GVISTDYWGQGTTVTVSS |
| 37 | AA | CDRL1 of 1K11 (FERM BP-10510) | RASQEISGYLI |
| 38 | AA | CDRL2 of 1K11 (FERM BP-10510) | AASTLDS |
| 39 | AA | CDRL3 of 1K11 (FERM BP-10510) | LQYANYPPT |
| 40 | DNA | VL of 1K11 (FERM BP-10510) | GACATCCAGATGACACAGTCTCCACCCTCCCT ATCTGCCTCTCTGGGAGAAAGAGTCAGTCTCA CTTGTCGGGCAAGTCAGGAAATTAGTGGTTAC TTAATCTGGCTTCAACAGAAACCAGATGGAAC TATTCAACGCCTGATCTACGCCGCATCCACTTT AGATTCTGGTGTCCCAAAAAGGTTCAGTGGCA GTAGGTCTGGGTCAGATTATTCTCTCACCATCA GCAGCCTTGAGTCTGAAGATTTTGCAGACTAT TACTGTCTACAATATGCTAATTATCCTCCGACG TTCGGTGGAGGCACCAAGCTGGAAATCAAAC GG |
| 41 | AA | Mature VL of 1K11 (FERM BP-10510) | DIQMTQSPPSLSASLGERVSLTCRASQEISGYLIW LQQKPDGTIQRLIYAASTLDSGVPKRFSGSRSGS DYSLTISSLESEDFADYYCLQYANYPPTFGGGTK LEIKR |
| 42 | AA | CDRH1 of 21C5 (FERM BP-10511) | DYYMY |
| 43 | AA | CDRH2 of 21C5 (FERM BP-10511) | TISDGGNYTYYPDSVKG |
| 44 | AA | CDRH3 of 21C5 (FERM BP-10511) | DRDGSSLFAY |
| 45 | DNA | VH of 21C5 (FERM BP-10511) | GTGCAGCTGCAGGAGTCTGGGGGAGGCTTAG TGAAGCCTGGAGGGTCCCTGAAACTCTCCTGT GCAGCCTCTGGATTCACTTTCAGTGACTATTAC ATGTATTGGGTTCGCCAGACTCCGGAAAAGAG GCTGGAGTGGGTCGCAACCATTAGTGATGGTG GTAATTACACCTACTATCCAGACAGTGTGAAG GGGCGATTCACCATCTCCAGAGACAATGCCAA GAATAACCTGTACCTGCAAATGAGCAGTCTGA AGTCTGAGGACACAGCCATGTATTACTGTGCA |

| SEQ ID NO. | TYPE | DESCRIPTION | SEQUENCE |
|---|---|---|---|
| | | | AGAGATCGGGACGGTAGTAGCCTGTTTGCTTA CTGGGGCCAAGGGACCACGGTCACCGTCTCC TCA |
| 46 | AA | Mature VH of 21C5 (FERM BP-10511) starting from 2nd residue according to Kabat numbering | ?VQLQESGGGLVKPGGSLKLSCAASGFTFSDYY MYWVRQTPEKRLEWVATISDGGNYTYYPDSVK GRFTISRDNAKNNLYLQMSSLKSEDTAMYYCA RDRDGSSLFAYWGQGTTVTVSS |
| 47 | AA | CDRL1 of 21C5 (FERM BP-10511) | KASQDVNIAVA |
| 48 | AA | CDRL2 of 21C5 (FERM BP-10511) | WASTRHT |
| 49 | AA | CDRL3 of 21C5 (FERM BP-10511) | QQHYNTPW |
| 50 | DNA | VL of 21C5 (FERM BP-10511) | CATCCAGATGACACAGTCTCCAAATTCATGTC CACATCAGTAGGAGACAGGGTCAGCATCACCT GCAAGGCCAGTCAGGATGTGAATATTGCTGTA GCCTGGTATCAACAAAGACCAGGGCAATCTCC TAAACTACTGATTTACTGGGCATCCACCCGGC ACACTGGAGTCCCTGATCGCTTCACAGGCAGT GGATCTGGGACAGATTATACTCTCACCATCAG CAGTGTGCAGGCTGAAGACCTGGCACTTTATT ACTGTCAGCAACATCATAACACTCCGTGGACG TTCGGTGGAGGCACCAAGCTGGAAATCAAAC GG |
| 51 | AA | Mature VL of 21C5 (FERM BP-10511) | HPDDTVSKFMSTSVGDRVSITCKASQDVNIAVA WYQQRPGQSPKLLIYWASTRHTGVPDRFTGSGS GTDYTLTISSVQAEDLALYYCQQHYNTPWTFGG GTKLEIKR |
| 52 | AA | CDRH1 of 25B6 (FERM BP-10513) | SYGVH |
| 53 | AA | CDRH2 of 25B6 (FERM BP-10513) | VIWSGGSTNYNSALMS |
| 54 | AA | CDRH3 of 25B6 (FERM BP-10513) | DYGNYPWFAY |
| 55 | DNA | VH of 25B6 (FERM BP-10513) | GTCAAGCTGCAGCAGTCTGGACCTGGCCTGG TGGCGCCCTCACAGAGCCTGTCCATCACTTGC ACTGTCTCTGGGTTTTCATTAACCAGTTATGGT GTACACTGGGTTCGCCAGCCTCCAGGAAAGG GTCTGGAGTGGCTGGGAGTAATATGGTCTGGT GGAAGCACAAATTATAATTCGGCTCTCATGTCC AGACTGAGCATCAGTAAAGACAATTTTAAGAG CCAAGTTTTCTTAAAAATGAACAGTCTGCAAA CTGATGACACAGCCATATACTACTGTGCCAGA GACTATGGTAACTACCCCTGGTTTGCTTACTGG GGCCAAGGGACCACGGTCACCGTCTCCTCA |
| 56 | AA | Mature VH of 25B6 (FERM BP-10513) starting from 2nd residue according to Kabat numbering | ?VKLQQSGPGLVAPSQSLSITCTVSGFSLTSYGV HWVRQPPGKGLEWLGVIWSGGSTNYNSALMS RLSISKDNFKSQVFLKMNSLQTDDTAIYYCARD YGNYPWFAYWGQGTTVTVS |

| SEQ ID NO. | TYPE | DESCRIPTION | SEQUENCE |
|---|---|---|---|
| 57 | AA | CDRL1 of 25B6 (FERM BP-10513) | KASQDVNTAVA |
| 58 | AA | CDRL2 of 25B6 (FERM BP-10513) | SASYRYT |
| 59 | AA | CDRL3 of 25B6 (FERM BP-10513) | QQHYSTPCA |
| 60 | DNA | VL of 25B6 (FERM BP-10513) | CATCCAGATGACACAGTCTCCAAATTCATGTC CACATCAGTAGGAGACAGGGTCAGCATCACCT GCAAGGCCAGTCAGGATGTGAATACTGCTGTG GCCTGGTATCAACAGAAACCAGGACAATCCCC TAAACTACTGATTTACTCGGCATCCTACCGGTA CACTGGAGTCCCTGATCGCTTCACTGGCAGTG GATCTGGGACGGATTTCACTTTCACCATCAGC AGTGTGCAGGCTGAAGACCTGGCAGTTTATTA CTGTCAGCAACATTATAGTACTCCGTGCGCGTT CGGAGGGGGGACAAAGTTGGAAATAAAACGG |
| 61 | AA | Mature VL of 25B6 (FERM BP-10513) | HPDDTVSKFMSTSVGDRVSITCKASQDVNTAVA WYQQKPGQSPKLLIYSASYRYTGVPDRFTGSGS GTDFTFTISSVQAEDLAVYYCQQHYSTPCAFGG GTKLEIKR |
| 62 | AA | CDRH1 of 28S1 (FERM BP-10832) | GYGVN |
| 63 | AA | CDRH2 of 28S1 (FERM BP-10832) | MIWGDGITEYNSALKS |
| 64 | AA | CDRH3 of 28S1 (FERM BP-10832) | RDASSGYGFA |
| 65 | DNA | VH of 28S1 (FERM BP-10832) | AGGTGAAGCTGCAGGAGTCAGGACCTGGCCT GGTGGCGCCCTCACAGAGCCTGTCCATCACAT GCACCGTCTCAGGGTTCTCATTAACCGGCTAT GGTGTAAACTGGGTTCGCCAGCCTCCAGGAA AGGGTCTGGAGTGGCTGGGAATGATATGGGGT GATGGAATCACAGAGTATAATTCAGCTCTCAA ATCCAGACTGAGCATCAGCAAGGACAACTCC AAGAGCCAAGTTTTCTTAAAAATGAACAGTCT GCAAACTGATGACACAGCCAGGTACTACTGTG CCAGAGATGCCAGCTCGGGCTACGGGTTTGCT TACTGGGGCCAAGGGACCACGGTCACCGTCT CCTCA |
| 66 | AA | Mature VH of 28S1 (FERM BP-10832) starting from 2nd residue according to Kabat numbering | ?VKLQESGPGLVAPSQSLSITCTVSGFSLTGYGV NWVRQPPGKGLEWLGMIWGDGITEYNSALKSR LSISKDNSKSQVFLKMNSLQTDDTARYYCARDA SSGYGFAYWGQGTTVTVSS |
| 67 | AA | CDRL1 of 28S1 (FERM BP-10832) | TASSSVSSSYLH |
| 68 | AA | CDRL2 of 28S1 (FERM BP-10832) | STSNLAS |
| 69 | AA | CDRL3 of 28S1 (FERM BP-10832) | HQYHRSPYT |

| SEQ ID NO. | TYPE | DESCRIPTION | SEQUENCE |
|---|---|---|---|
| 70 | DNA | VL of 28S1 (FERM BP-10832) | TACATTGTGCTGACCCAGTCTCCAGCAATCAT GTCTGCATCTCTAGGGGAACGGGTCACCATGA CCTGCACTGCCAGCTCAAGTGTAAGTTCCAGT TACTTGCACTGGTACCAGCAGAAGCCAGGATC CTCCCCCAAACTCTGGATTTATAGCACATCCAA CCTGGCTTCTGGAGTCCCAGCTCGCTTCAGTG GCAGTGGGTCTGGGACCTCTTACTCTCTCACA ATCAGCAGCATGGAGGCTGAAGATGCTGCCAC TTATTACTGCCACCAGTATCATCGTTCCCCGTA CACGTTCGGAGGGGGGACAAAGTTGGAAATA AAACGG |
| 71 | AA | Mature VL of 28S1 (FERM BP-10832) | YIVLTQSPAIMSASLGERVTMTCTASSSVSSSYL HWYQQKPGSSPKLWIYSTSNLASGVPARFSGSG SGTSYSLTISSMEAEDAATYYCHQYHRSPYTFG GGTKLEIKR |
| 72 | DNA | VH of 24I11 (FERM BP-10512) including sequence encoding signal peptide (1-57), flanked by SpeI and HindIII sites | ACTAGTACCACCATGAAATGCAGCTGGGTTAT CTTCTTCCTGATGGCAGTGGTTACAGGGGTCA ATTCAGAGGTTCAGCTGCAGCAGTCTGGGGC AGAGCTTGTGAAGCCAGGGGCCTCAGTCAAG TTGTCCTGCACAGCTTCTGGCTTCAACATTAA AGACACCTATGTGCACTGGGTGAAGCAGAGG CCTGAACAGGGCCTGGAGTGGATTGGAAATAT TGATCCTGCGAATGGTAATACTAAATATGACCC GAAGTTCCAGGGCAAGGCCACTATAACAGCA GACACATCCTCCAACACAGCCTACCTGCACCT CAGCAGCCTGACATCTGAGGACACTGCCGTCT ATTACTGTGCTAGATGGTTACGACATTTTTACT ATGCTATGGACTACTGGGGTCAAGGAACCTCA GTCACCGTCTCCTCAGGTAAGAATGGCCTCTA AGCTT |
| 73 | DNA | VL of 24I11 (FERM BP-10512) including sequence encoding signal peptide (1-60), flanked by NheI and EcoRI sites | GCTAGCACCACCATGAGTGTGCCCACTCAACT CCTGGGGTTGCTGCTGCTGTGGCTTACAGACG CAGGATGTGACATCCAGATGACTCAGTCTCCA GCCTCCCTGGCTGCATCTGTGGGAGAAACTGT CACCGACATCCAGATGACTCAGTCTCCAGCCT CCCTGGCTGCATCTGTGGGAGAAACTGTCACC GGGAAATCTCCTCAGCTCCTGATCTATAATGCA AACAGCTTGGAAGATGGTGTCCCATCGAGGTT CAGTGGCAGTGGATCTGGGACACAGTATTCTA TGAAGATCAACAGCATGCAGCCTGAAGATACC GCAACTTATTTCTGTAAACAGGCTTATGACGTT CCGTACACGTTCGGAGGGGGGACCAAGCTGG AAATAAAACGTAAGTAGTCTTCTCAGAATTC |
| 74 | DNA | FIG. 10 (w/ 5'-GGG & CCC-) and FIG. 12 Hu24I11 VH gene flanked by SpeI and HindIII sites | ACTAGTACCACCATGAAATGCAGCTGGGTTAT CTTCTTCCTGATGGCAGTGGTTACAGGGGTCA ATTCACAGGTTCAGCTGGTGCAGTCTGGGGCA GAGGTGAAGAAGCCAGGGGCCTCAGTCAAGG TTTCCTGCAAGGCTTCTGGCTTCAACATTAAA GACACCTATGTGCACTGGGTGCGCCAGGCCCC TGGACAGAGGCTGGAGTGGATTGGAAATATTG ATCCTGCGAATGGTAATACTAAATATGACCCGA AGTTCCAGGGCAAGGCCACTATAACAGCAGA CACATCCGCGAGCACAGCCTACATGGAGCTCA GCAGCCTGAGATCTGAGGACACTGCCGTCTAT TACTGTGCTAGATGGTTACGACATTTTTACTAT GCTATGGACTACTGGGGTCAAGGAACCCTGGT CACCGTCTCCTCAGGTGAGTCCTCACAAAAGC TT |
| 75 | DNA | FIG. 11 (w/ 5'-GGG & CCC-) and FIG. 13 Hu24I11 VL gene flanked by NheI and EcoRI sites | GCTAGCACCACCATGAGTGTGCCCACTCAACT CCTGGGGTTGCTGCTGCTGTGGCTTACAGACG CACGATGTGACATCCAGATGACTCAGTCTCCA TCCTCCCTGTCTGCATCTGTGGGAGACAGAGT CACCATCACATGTCGAGCAAGTGAGAACATTT ACTACAGTTTAGCATGGTATCAGCAGAAGCCA GGGAAAGCCCCTAAGCTCCTGATCTATAATGC AAACAGCTTGGAAGATGGTGTCCCATCGAGGT TCAGTGGCAGTGGATCTGGGACACAGTATACT CTCACCATCAGCAGCCTGCAGCCTGAAGATTT TGCAACTTATTACTGTAAACAGGCTTATGACGT TCCGTACACGTTCGGACAAGGGACCAAGGTG GAAATCAAACGTGAGTAGAATTTAAAGAATTC |

| SEQ ID NO. | TYPE | DESCRIPTION | SEQUENCE |
|---|---|---|---|
| 76 | AA | Human α9 integrin (signal peptide; 1-29 residues; in italic) | *MGGPAAPRGAGRLRALLLALVVAGIPAGA*YNLDPQ RPVHFQGPADSFFGYAVLEHFHDNTRWVLVGAP KADSKYSPSVKSPGAVFKCRVHTNPDRRCTELD MARGKNRGTSCGKTCREDRDDEWMGVSLARQ PKADGRVLACAHRWKNIYYEADHILPHGFCYII PSNLQAKGRTLIPCYEEYKKKYGEEHGSCQAGI AGFFTEELVVMGAPGSFYWAGTIKVLNLTDNTY LKLNDEVIMNRRYTYLGYAVTAGHFSHPSTIDV VGGAPQDKGIGKVYIFRADRRSGTLIKIFQASGK KMGSYFGSSLCAVDLNGDGLSDLLVGAPMFSEI RDEGGQVTVYINRGNGALEEQLALTGDGAYNAH FGESIASLDDLDNDGFPDVAIGAPKEDDFAGAV YIYHGDAGGIVPQYSMKLSGQKINPVLRMFGQS ISGGIDMDGNGYPDVTVGAFMSDSVVLLRARP VITVDVSIFLPGSINITAPQCHDGQQPVNCLNVT TCFSFHGKHVPGEIGLNYVLMADVAKKEKGQM PRVYFVLLGETMGQVTEKLQLTYMEETCRHYV AHVKRRVQDVISPIVFEAAYSLSEHVTGEEEREL PPLTPVLRWKKGQKIAQKNQTVFERNCRSEDCA ADLQLQGKLLLSSMDEKTLYLALGAVKNISLNI SISNLGDDAYDANVSFNVSRELFFINMWQKEEM GISCELLESDFLKCSVGFPFMRSKSKYEFSVIFDT SHLSGEEEVLSFIVTAQSGNTERSESLHDNTLVL MVPLMHEVDTSITGIMSPTSFVYGESVDAANFI QLDDLECHFQPINITLQVYNTGPSTLPGSSVSISF PNRLSSGGAEMFHVQEMVVGQEKGNCSFQKNP TPCIIPQEQENIFHTIFAFFTKSGRKVLDCEKPGIS CLTAHCNFSALAKEESRTIDIYMLLNTEILKKDS SSVIQFMSRAKVKVDPALRVVEIAHGNPEEVTV VFEALHNLEPRGYVVGWIIAISLLVGILIFLLLAV LLWKMGFFRRRYKEIIEAEKNRKENEDSWDWV QKNQ |
| 77 | AA | Partial aa sequence of huα9 integrin | FQGPADSFFGYA |
| 78 | AA | Partial aa sequence of huα9 integrin | KSPGAVFKCRVHTNPDRR |
| 79 | AA | Partial aa sequence of huα9 integrin | WMGVSLARQPKADGRVLA |
| 80 | aa | Partial aa sequence of huα9 integrin | CAHRWKNIYYEADHI |
| 81 | aa | Partial aa sequence of huα9 integrin | GFCYIIPSNLQAKGRTLI |
| 82 | aa | Partial aa sequence of huα9 integrin | VMGAPGSFYWAGTIKVLN |
| 83 | aa | Partial aa sequence of huα9 integrin | VIMNRRYTYLGYAVT |
| 84 | aa | Partial aa sequence of huα9 integrin | VYIFRADRRSGTLIKIFQ |
| 85 | aa | Partial aa sequence of huα9 integrin | QYSMKLSGQKINPVLRMFGQSISG |
| 86 | aa | Partial aa sequence of huα9 integrin | VVLLRARPVITVDVSIFL |

| SEQ ID NO. | TYPE | DESCRIPTION | SEQUENCE |
|---|---|---|---|
| 87 | aa | Partial aa sequence of huα9 integrin | RHYVAHVKRRVQDVISPI |
| 88 | aa | Partial aa sequence of huα9 integrin | ELPPLTPVLRWKKGQKIAQKNQTVFERNCR |
| 89 | aa | Partial aa sequence of huα9 integrin | YLALGAVKNISL |
| 90 | aa | Partial aa sequence of huα9 integrin | CSVGFPFMRSKSKYEFSV |
| 91 | aa | Partial aa sequence of huα9 integrin | SSSVIQFMSRAKVKVDPALRV |
| 92 | aa | Tenascin-C huα9-binding site | AEIDGIEL |
| 93 | aa | Human fibronectin huα9-binding site | CPEDGIHELFP |
| 94 | DNA | GeneRacer 5' primer | CGACTGGAGCACGAGGACACTGA |
| 95 | DNA | VH primer | GCCAGTGGATAGACAGATGG |
| 96 | DNA | VL primer | GATGGATACAGTTGGTGCAGC |
| 97 | DNA | VH 5' primer w/ SpeI site | GGGACTAGTACCACCATGAAATGCAGCTGGGTTATCTTC |
| 98 | DNA | VH primer w/ HindIII site | GGGAAGCTTAGAGGCCATTCTTACCTGAGGAGACGGTGACTGAGGTTCC3 |
| 99 | DNA | VL 5' primer w/ NheI site | GGGGCTAGCACCACCATGAGTGTGCCCACTCAACTCCTG |
| 100 |  | VL 5' primer w/ EcpRI site | GGGGAATTCTGAGAAGACTACTTACGTTTTATTTCCAGCTTGGTCCCCCC |
| 101 | DNA | JNJ120 | GGGACTAGTACCACCATGAAATGCAGC |
| 102 | DNA | JNJ137 | GGGACTAGTACCACCATGAAATGCAGCTGGGTTATCTTCTTCCTGATGGCAGTGGTT |
| 103 | DNA | JNJ138 | AGACTGCACCAGCTGAACCTGTGAATTGACCCCTGTAACCACTGCCATCAGGAAGAA |
| 104 | DNA | JNJ139 | CAGGTTCAGCTGGTGCAGTCTGGGGCAGAGGTGAAGAAGCCAGGGGCCTCAGTCAAG |
| 105 | DNA | JNJ140 | GTCTTTAATGTTGAAGCCAGAAGCCTTGCAGGAAACCTTGACTGAGGCCCCTGGCTT |
| 106 | DNA | JNJ141 | TCTGGCTTCAACATTAAAGACACCTATGTGCACTGGGTGCGCCAGGCCCCTGGACAGAGG |
| 107 | DNA | JNJ142 | ACCATTCGCAGGATCAATATTTCCAATCCACTCCAGCCTCTGTCCAGGGGCCTGGCG |
| 108 | DNA | JNJ143 | AATATTGATCCTGCGAATGGTAATACTAAATATGACCCGAAGTTCCAGGGCAAGGCCACT |
| 109 | DNA | JNJ144 | CATGTAGGCTGTGCTCGCGGATGTGTCTGCTGTTATAGTGGCCTTGCCCTGGAACTT |

-continued

| SEQ ID NO. | TYPE | DESCRIPTION | SEQUENCE |
|---|---|---|---|
| 110 | DNA | JNJ145 | TCCGCGAGCACAGCCTACATGGAGCTCAGCA GCCTGAGATCTGAGGACACTGCCGTC |
| 111 | DNA | JNJ146 | ATAGTAAAAATGTCGTAACCATCTAGCACAGT AATAGACGGCAGTGTCCTCAGA |
| 112 | DNA | JNJ147 | TGGTTACGACATTTTTACTATGCTATGGACTAC TGGGGTCAAGGAACCCTGGTCACC |
| 113 | DNA | JNJ148 | GGGAAGCTTTTGTGAGGACTCACCTGAGGAG ACGGTGACCAGGGTTCCTTGACC |
| 114 | DNA | JNJ149 | GGGAAGCTTTTGTGAGGACTC |
| 115 | DNA | JNJ150 | GGGGCTAGCACCACCATGAGT |
| 116 | DNA | JNJ126 | GGGGCTAGCACCACCATGAGTGTGCCCACTCA ACTCCTGGGGTTGCTGCTGCTGTGG |
| 117 | DNA | JNJ127 | AGACTGAGTCATCTGGATGTCACATCGTGCGT CTGTAAGCCACAGCAGCAGCAACCCCAG |
| 118 | DNA | JNJ128 | GACATCCAGATGACTCAGTCTCCATCCTCCCT GTCTGCATCTGTGGGAGACAGA |
| 119 | DNA | JNJ129 | GTAAATGTTCTCACTTGCTCGACATGTGATGGT GACTCTGTCTCCCACAGATGCAGA |
| 120 | DNA | JNJ130 | CGAGCAAGTGAGAACATTTACTACAGTTTAGC ATGGTATCAGCAGAAGCCAGGGAAA |
| 121 | DNA | JNJ131 | CAAGCTGTTTGCATTATAGATCAGGAGCTTAG GGGCTTTCCCTGGCTTCTGCTGATA |
| 122 | DNA | JNJ132 | ATCTATAATGCAAACAGCTTGGAAGATGGTGT CCCATCGAGGTTCAGTGGCAGTGGA |
| 123 | DNA | JNJ133 | CAGGCTGCTGATGGTGAGAGTATACTGTGTCC CAGATCCACTGCCACTGAACCTCGA |
| 124 | DNA | JNJ134 | ACTCTCACCATCAGCAGCCTGCAGCCTGAAGA TTTTGCAACTTATTACTGTAAACAG |
| 125 | DNA | JNJ135 | GGTCCCTTGTCCGAACGTGTACGGAACGTCAT AAGCCTGTTTACAGTAATAAGTTGC |
| 126 | DNA | JNJ136 | TACACGTTCGGACAAGGGACCAAGGTGGAAA TCAAACGTGAGTAG |
| 127 | DNA | JNJ101 | GGGGAATTCTTTAAATTCTACTCACGTTTGATT TCCA |
| 128 | DNA | JNJ117 | GGGGAATTCTTTAAATTCTA |
| 129 | DNA | Primer for mouse γ1, γ2a, γ2b and γ3 H-chains | GCCAGTGGATAGACTGATGG |
| 130 | DNA | Primer for mouse κ L-chain primer | GATGGATACAGTTGGTGCAGC |

The invention claimed is:

1. A humanized antibody or an antigen-binding fragment thereof that immunospecifically recognizes human α9integrin, comprising:
   (i) a H-chain comprising the amino acid sequence of SEQ ID NO:29; and
   (ii) a L-chain comprising the amino acid sequence of SEQ ID NO:31.

2. A pharmaceutical composition comprising the humanized antibody or an antigen-binding fragment thereof of claim 1, and a pharmaceutically acceptable carrier.

* * * * *

SEQUENCE LISTING

<160> NUMBER OF SEQ ID NOS: 130

<210> SEQ ID NO 1
<211> LENGTH: 5
<212> TYPE: PRT
<213> ORGANISM: Unknown
<220> FEATURE:
<221> NAME/KEY: misc_feature
<222> LOCATION: (1)...(5)
<223> OTHER INFORMATION: Osteopontin adhesion sequence

<400> SEQUENCE: 1

Gly Arg Gly Asp Ser
1               5

<210> SEQ ID NO 2
<211> LENGTH: 7
<212> TYPE: PRT
<213> ORGANISM: Homo sapiens
<220> FEATURE:
<221> NAME/KEY: misc_feature
<222> LOCATION: (1)...(7)
<223> OTHER INFORMATION: Human osteopontin alpha4 beta1/alpha9
      beta1-binding site

<400> SEQUENCE: 2

Ser Val Val Tyr Gly Leu Arg
1               5

<210> SEQ ID NO 3
<211> LENGTH: 7
<212> TYPE: PRT
<213> ORGANISM: Mus musculus
<220> FEATURE:
<221> NAME/KEY: misc_feature
<222> LOCATION: (1)...(7)
<223> OTHER INFORMATION: Mouse osteopontin alpha4 beta1/alpha9
      beta1-binding site

<400> SEQUENCE: 3

Ser Leu Ala Tyr Gly Leu Arg
1               5

<210> SEQ ID NO 4
<211> LENGTH: 5
<212> TYPE: PRT
<213> ORGANISM: Artificial Sequence
<220> FEATURE:
<223> OTHER INFORMATION: synthetically constructed CDRH1 of 24I11 (FERM
      BP-10512)

<400> SEQUENCE: 4

Asp Thr Tyr Val His
1               5

<210> SEQ ID NO 5
<211> LENGTH: 17
<212> TYPE: PRT
<213> ORGANISM: Artificial Sequence
<220> FEATURE:
<223> OTHER INFORMATION: synthetically constructed CDRH2 of 24I11 (FERM
      BP-10512)

<400> SEQUENCE: 5

Asn Ile Asp Pro Ala Asn Gly Asn Thr Lys Tyr Asp Pro Lys Phe Gln
1               5                   10                  15

Gly

<210> SEQ ID NO 6
<211> LENGTH: 11
<212> TYPE: PRT
<213> ORGANISM: Artificial Sequence
<220> FEATURE:
<223> OTHER INFORMATION: synthetically constructed CDRH3 of 24I11 (FERM BP-10512)

<400> SEQUENCE: 6

Trp Leu Arg His Phe Tyr Tyr Ala Met Asp Tyr
1               5                   10

<210> SEQ ID NO 7
<211> LENGTH: 417
<212> TYPE: DNA
<213> ORGANISM: Mus musculus
<220> FEATURE:
<221> NAME/KEY: misc_feature
<222> LOCATION: (1)...(417)
<223> OTHER INFORMATION: VH of 24I11 (FERM BP-10512)
<220> FEATURE:
<221> NAME/KEY: misc_feature
<222> LOCATION: (1)...(57)
<223> OTHER INFORMATION: sequence encoding signal peptide

<400> SEQUENCE: 7

```
atgaaatgca gctgggttat cttcttcctg atggcagtgg ttacaggggt caattcagag      60
gttcagctgc agcagtctgg ggcagagctt gtgaagccag gggcctcagt caagttgtcc     120
tgcacagctt ctggcttcaa cattaaagac acctatgtgc actgggtgaa gcagaggcct     180
gaacagggcc tggagtggat tggaaatatt gatcctgcga atggtaatac taaatatgac     240
ccgaagttcc agggcaaggc cactataaca gcagacacat cctccaacac agcctacctg     300
cacctcagca gcctgacatc tgaggacact gccgtctatt actgtgctag atggttacga     360
cattttact atgctatgga ctactgggt caaggaacct cagtcaccgt ctcctca         417
```

<210> SEQ ID NO 8
<211> LENGTH: 139
<212> TYPE: PRT
<213> ORGANISM: Mus musculus
<220> FEATURE:
<221> NAME/KEY: misc_feature
<222> LOCATION: (1)...(139)
<223> OTHER INFORMATION: VH of 24I11 (FERM BP-10512)
<220> FEATURE:
<221> NAME/KEY: SIGNAL
<222> LOCATION: (1)...(19)
<223> OTHER INFORMATION: signal peptide

<400> SEQUENCE: 8

Met Lys Cys Ser Trp Val Ile Phe Phe Leu Met Ala Val Val Thr Gly
1               5                   10                  15

Val Asn Ser Glu Val Gln Leu Gln Gln Ser Gly Ala Glu Leu Val Lys
            20                  25                  30

Pro Gly Ala Ser Val Lys Leu Ser Cys Thr Ala Ser Gly Phe Asn Ile
        35                  40                  45

Lys Asp Thr Tyr Val His Trp Val Lys Gln Arg Pro Glu Gln Gly Leu
    50                  55                  60

Glu Trp Ile Gly Asn Ile Asp Pro Ala Asn Gly Asn Thr Lys Tyr Asp
65                  70                  75                  80

Pro Lys Phe Gln Gly Lys Ala Thr Ile Thr Ala Asp Thr Ser Ser Asn
                85                  90                  95

Thr Ala Tyr Leu His Leu Ser Ser Leu Thr Ser Glu Asp Thr Ala Val

```
              100                 105                 110
Tyr Tyr Cys Ala Arg Trp Leu Arg His Phe Tyr Tyr Ala Met Asp Tyr
        115                 120                 125
Trp Gly Gln Gly Thr Ser Val Thr Val Ser Ser
        130                 135

<210> SEQ ID NO 9
<211> LENGTH: 120
<212> TYPE: PRT
<213> ORGANISM: Mus musculus
<220> FEATURE:
<221> NAME/KEY: misc_feature
<222> LOCATION: (1)...(120)
<223> OTHER INFORMATION: mature VH of 24I11 (FERM BP-10512)

<400> SEQUENCE: 9

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Val His Trp Val Lys Gln Arg Pro Glu Gln Gly Leu Glu Trp Ile
        35                  40                  45

Gly Asn Ile Asp Pro Ala Asn Gly Asn Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu His Leu Ser Ser Leu Thr Ser Glu Asp Thr Ala Val Tyr Tyr Cys
                85                  90                  95

Ala Arg Trp Leu Arg His Phe Tyr Tyr Ala Met Asp Tyr Trp Gly Gln
            100                 105                 110

Gly Thr Ser Val Thr Val Ser Ser
        115                 120

<210> SEQ ID NO 10
<211> LENGTH: 19
<212> TYPE: PRT
<213> ORGANISM: Mus musculus
<220> FEATURE:
<221> NAME/KEY: SIGNAL
<222> LOCATION: (1)...(19)
<223> OTHER INFORMATION: signal peptide of 24I11 H-chain

<400> SEQUENCE: 10

Met Lys Cys Ser Trp Val Ile Phe Phe Leu Met Ala Val Val Thr Gly
1               5                   10                  15

Val Asn Ser

<210> SEQ ID NO 11
<211> LENGTH: 11
<212> TYPE: PRT
<213> ORGANISM: Mus musculus
<220> FEATURE:
<221> NAME/KEY: misc_feature
<222> LOCATION: (1)...(11)
<223> OTHER INFORMATION: CDRL1 of 24I11 (FERM BP-10512)

<400> SEQUENCE: 11

Arg Ala Ser Glu Asn Ile Tyr Tyr Ser Leu Ala
1               5                   10

<210> SEQ ID NO 12
<211> LENGTH: 7
```

```
<212> TYPE: PRT
<213> ORGANISM: Mus musculus
<220> FEATURE:
<221> NAME/KEY: misc_feature
<222> LOCATION: (1)...(7)
<223> OTHER INFORMATION: CDRL2 of 24I11 (FERM BP-10512)

<400> SEQUENCE: 12

Asn Ala Asn Ser Leu Glu Asp
1               5

<210> SEQ ID NO 13
<211> LENGTH: 9
<212> TYPE: PRT
<213> ORGANISM: Mus musculus
<220> FEATURE:
<221> NAME/KEY: misc_feature
<222> LOCATION: (1)...(9)
<223> OTHER INFORMATION: CDRL3 of 24I11 (FERM BP-10512)

<400> SEQUENCE: 13

Lys Gln Ala Tyr Asp Val Pro Tyr Thr
1               5

<210> SEQ ID NO 14
<211> LENGTH: 381
<212> TYPE: DNA
<213> ORGANISM: Mus musculus
<220> FEATURE:
<221> NAME/KEY: misc_feature
<222> LOCATION: (1)...(381)
<223> OTHER INFORMATION: VL of 24I11 (FERM BP-10512)
<220> FEATURE:
<221> NAME/KEY: misc_feature
<222> LOCATION: (1)...(60)
<223> OTHER INFORMATION: sequence encoding signal peptide

<400> SEQUENCE: 14
atgagtgtgc ccactcaact cctggggttg ctgctgctgt ggcttacaga cgcaggatgt      60
gacatccaga tgactcagtc tccagcctcc ctggctgcat ctgtgggaga aactgtcacc     120
gacatccaga tgactcagtc tccagcctcc ctggctgcat ctgtgggaga aactgtcacc     180
gggaaatctc ctcagctcct gatctataat gcaaacagct tggaagatgg tgtcccatcg     240
aggttcagtg gcagtggatc tgggacacag tattctatga agatcaacag catgcagcct     300
gaagataccg caacttattt ctgtaaacag gcttatgacg ttccgtacac gttcggaggg     360
gggaccaagc tggaaataaa a                                               381

<210> SEQ ID NO 15
<211> LENGTH: 127
<212> TYPE: PRT
<213> ORGANISM: Mus musculus
<220> FEATURE:
<221> NAME/KEY: misc_feature
<222> LOCATION: (1)...(127)
<223> OTHER INFORMATION: VL of 24I11 (FERM BP-10512)
<220> FEATURE:
<221> NAME/KEY: SIGNAL
<222> LOCATION: (1)...(20)
<223> OTHER INFORMATION: signal peptide

<400> SEQUENCE: 15

Met Ser Val Pro Thr Gln Leu Leu Gly Leu Leu Leu Leu Trp Leu Thr
1               5                   10                  15

Asp Ala Gly Cys Asp Ile Gln Met Thr Gln Ser Pro Ala Ser Leu Ala
            20                  25                  30
```

Ala Ser Val Gly Glu Thr Val Thr Ile Thr Cys Arg Ala Ser Glu Asn
            35                  40                  45

Ile Tyr Tyr Ser Leu Ala Trp Tyr Gln Gln Lys Gln Gly Lys Ser Pro
 50                  55                  60

Gln Leu Leu Ile Tyr Asn Ala Asn Ser Leu Glu Asp Gly Val Pro Ser
 65                  70                  75                  80

Arg Phe Ser Gly Ser Gly Ser Gly Thr Gln Tyr Ser Met Lys Ile Asn
                85                  90                  95

Ser Met Gln Pro Glu Asp Thr Ala Thr Tyr Phe Cys Lys Gln Ala Tyr
            100                 105                 110

Asp Val Pro Tyr Thr Phe Gly Gly Gly Thr Lys Leu Glu Ile Lys
        115                 120                 125

<210> SEQ ID NO 16
<211> LENGTH: 107
<212> TYPE: PRT
<213> ORGANISM: Mus musculus
<220> FEATURE:
<221> NAME/KEY: misc_feature
<222> LOCATION: (1)...(107)
<223> OTHER INFORMATION: mature VL of 24I11 (FERM BP-10512)

<400> SEQUENCE: 16

Asp Ile Gln Met Thr Gln Ser Pro Ala Ser Leu Ala Ala Ser Val Gly
 1               5                  10                  15

Glu Thr Val Thr Ile Thr Cys Arg Ala Ser Glu Asn Ile Tyr Tyr Ser
                20                  25                  30

Leu Ala Trp Tyr Gln Gln Lys Gln Gly Lys Ser Pro Gln Leu Leu Ile
            35                  40                  45

Tyr Asn Ala Asn Ser Leu Glu Asp Gly Val Pro Ser Arg Phe Ser Gly
 50                  55                  60

Ser Gly Ser Gly Thr Gln Tyr Ser Met Lys Ile Asn Ser Met Gln Pro
 65                  70                  75                  80

Glu Asp Thr Ala Thr Tyr Phe Cys Lys Gln Ala Tyr Asp Val Pro Tyr
                85                  90                  95

Thr Phe Gly Gly Gly Thr Lys Leu Glu Ile Lys
            100                 105

<210> SEQ ID NO 17
<211> LENGTH: 20
<212> TYPE: PRT
<213> ORGANISM: Mus musculus
<220> FEATURE:
<221> NAME/KEY: SIGNAL
<222> LOCATION: (1)...(20)
<223> OTHER INFORMATION: signal peptide of 24I11 L-chain

<400> SEQUENCE: 17

Met Ser Val Pro Thr Gln Leu Leu Gly Leu Leu Leu Leu Trp Leu Thr
 1               5                  10                  15

Asp Ala Gly Cys
            20

<210> SEQ ID NO 18
<211> LENGTH: 429
<212> TYPE: DNA
<213> ORGANISM: Homo sapiens
<220> FEATURE:
<221> NAME/KEY: misc_feature
<222> LOCATION: (1)...(429)
<223> OTHER INFORMATION: Human H-chain (X65891)

-continued

<400> SEQUENCE: 18

```
atggactgga cctggagggt cctcttttg gtggcagcag ccacaggtgc ccactcccag    60
gtccagcttg tgcagtctgg ggctgaggtg aagaagcctg gggcctcagt gaaggtttcc   120
tgcaaggctt ctggatacac cttcactagc tatgctatgc attgggtgcg ccaggccccc   180
ggacaaaggc ttgagtggat gggatggatc aacgctggca atggtaacac aaaatattca   240
cagaagttcc agggcagagt caccattacc agggacacat ccgcgagcac agcctacatg   300
gagctgagca gcctgagatc tgaagacacg gctgtgtatt actgtgcgag aatacccgt    360 attagcagtg ctggttggg ggactacttt gactactggg gccagggaac cctggtcacc    420
gtctcctca                                                           429
```

<210> SEQ ID NO 19
<211> LENGTH: 30
<212> TYPE: PRT
<213> ORGANISM: Homo sapiens
<220> FEATURE:
<221> NAME/KEY: misc_feature
<222> LOCATION: (1)...(30)
<223> OTHER INFORMATION: FRH1 of (X65891)

<400> SEQUENCE: 19

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr
            20                  25                  30

<210> SEQ ID NO 20
<211> LENGTH: 14
<212> TYPE: PRT
<213> ORGANISM: Homo sapiens
<220> FEATURE:
<221> NAME/KEY: misc_feature
<222> LOCATION: (1)...(14)
<223> OTHER INFORMATION: FRH2 of (X65891)

<400> SEQUENCE: 20

Trp Val Arg Gln Ala Pro Gly Gln Arg Leu Glu Trp Met Gly
1               5                   10

<210> SEQ ID NO 21
<211> LENGTH: 32
<212> TYPE: PRT
<213> ORGANISM: Homo sapiens
<220> FEATURE:
<221> NAME/KEY: misc_feature
<222> LOCATION: (1)...(32)
<223> OTHER INFORMATION: FRH3 of (X65891)

<400> SEQUENCE: 21

Arg Val Thr Ile Thr Arg Asp Thr Ser Ala Ser Thr Ala Tyr Met Glu
1               5                   10                  15
Leu Ser Ser Leu Arg Ser Glu Asp Thr Ala Val Tyr Tyr Cys Ala Arg
            20                  25                  30

<210> SEQ ID NO 22
<211> LENGTH: 11
<212> TYPE: PRT
<213> ORGANISM: Homo sapiens
<220> FEATURE:
<221> NAME/KEY: misc_feature
<222> LOCATION: (1)...(11)
<223> OTHER INFORMATION: FRH4 of (X65891)

<400> SEQUENCE: 22

Trp Gly Gln Gly Thr Leu Val Thr Val Ser Ser
1               5                   10

<210> SEQ ID NO 23
<211> LENGTH: 370
<212> TYPE: DNA
<213> ORGANISM: Homo sapiens
<220> FEATURE:
<221> NAME/KEY: misc_feature
<222> LOCATION: (1)...(370)
<223> OTHER INFORMATION: Human kappa L-chain (X72441)

<400> SEQUENCE: 23

```
cgctcagctc ctggggctcc tgctactctg gctccgaggt gccagatgtg acatccagat     60
gacccagtct ccatcctccc tgtctgcatc tgtaggagac agagtcacca tcacttgccg    120
ggcaagtcag agcattagca gctatttaaa ttggtatcag cagaaaccag ggaaagcccc    180
taagctcctg atctatgctg catccagttt gcaaagtggg gtcccatcaa ggttcagtgg    240
cagtggatct gggacagatt tcactctcac catcagcagt ctgcaacctg aagattttgc    300
aacttactac tgtcaacaga gttacagtac ccctcggacg ttcggccaag ggaccaaggt    360
ggaaatcaaa                                                            370
```

<210> SEQ ID NO 24
<211> LENGTH: 23
<212> TYPE: PRT
<213> ORGANISM: Homo sapiens
<220> FEATURE:
<221> NAME/KEY: misc_feature
<222> LOCATION: (1)...(23)
<223> OTHER INFORMATION: FRL1 of X72441

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 25
<211> LENGTH: 15
<212> TYPE: PRT
<213> ORGANISM: Homo sapiens
<220> FEATURE:
<221> NAME/KEY: misc_feature
<222> LOCATION: (1)...(15)
<223> OTHER INFORMATION: FRL2 of X72441

<400> SEQUENCE: 25

Trp Tyr Gln Gln Lys Pro Gly Lys Ala Pro Lys Leu Leu Ile Tyr
1               5                   10                  15

<210> SEQ ID NO 26
<211> LENGTH: 32
<212> TYPE: PRT
<213> ORGANISM: Homo sapiens
<220> FEATURE:
<221> NAME/KEY: misc_feature
<222> LOCATION: (1)...(32)
<223> OTHER INFORMATION: FRL3 of X72441

<400> SEQUENCE: 26

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
              20                  25                  30

<210> SEQ ID NO 27
<211> LENGTH: 10
<212> TYPE: PRT
<213> ORGANISM: Homo sapiens
<220> FEATURE:
<221> NAME/KEY: misc_feature
<222> LOCATION: (1)...(10)
<223> OTHER INFORMATION: FRL4 of X72441

<400> SEQUENCE: 27

Phe Gly Gln Gly Thr Lys Val Glu Ile Lys
1               5                   10

<210> SEQ ID NO 28
<211> LENGTH: 360
<212> TYPE: DNA
<213> ORGANISM: Artificial Sequence
<220> FEATURE:
<223> OTHER INFORMATION: synthetically constructed VH of Hu24I11

<400> SEQUENCE: 28
caggttcagc tggtgcagtc tggggcagag gtgaagaagc caggggcctc agtcaaggtt      60
tcctgcaagg cttctggctt caacattaaa gacacctatg tgcactgggt gcgccaggcc     120
cctggacaga ggctggagtg gattggaaat attgatcctg cgaatggtaa tactaaatat     180
gacccgaagt tccagggcaa ggccactata acagcagaca catccgcgag cacagcctac     240
atggagctca gcagcctgag atctgaggac actgccgtct attactgtgc tagatggtta     300
cgacattttt actatgctat ggactactgg ggtcaaggaa ccctggtcac cgtctcctca     360

<210> SEQ ID NO 29
<211> LENGTH: 120
<212> TYPE: PRT
<213> ORGANISM: Artificial Sequence
<220> FEATURE:
<223> OTHER INFORMATION: synthetically constructed VH encoded by Hu24I11

<400> SEQUENCE: 29

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
              20                  25                  30

Tyr Val His Trp Val Arg Gln Ala Pro Gly Gln Arg Leu Glu Trp Ile
          35                  40                  45

Gly Asn Ile Asp Pro Ala Asn Gly Asn Thr Lys Tyr Asp Pro Lys Phe
      50                  55                  60

Gln Gly Lys Ala Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
              85                  90                  95

Ala Arg Trp Leu Arg His Phe Tyr Tyr Ala Met Asp Tyr Trp Gly Gln
          100                 105                 110

Gly Thr Leu Val Thr Val Ser Ser
      115                 120

<210> SEQ ID NO 30
<211> LENGTH: 321
<212> TYPE: DNA
<213> ORGANISM: Artificial Sequence

```
<220> FEATURE:
<223> OTHER INFORMATION: synthetically constructed VL of Hu24I11

<400> SEQUENCE: 30
gacatccaga tgactcagtc tccatcctcc ctgtctgcat ctgtgggaga cagagtcacc      60
atcacatgtc gagcaagtga aaacatttac tacagtttag catggtatca gcagaagcca     120
gggaaagccc ctaagctcct gatctataat gcaaacagct tggaagatgg tgtcccatcg     180
aggttcagtg gcagtggatc tgggacacag tatactctca ccatcagcag cctgcagcct     240
gaagattttg caacttatta ctgtaaacag gcttatgacg ttccgtacac gttcggacaa     300
gggaccaagg tggaaatcaa a                                               321

<210> SEQ ID NO 31
<211> LENGTH: 107
<212> TYPE: PRT
<213> ORGANISM: Artificial Sequence
<220> FEATURE:
<223> OTHER INFORMATION: synthetically constructed VL encoded by Hu24I11

<400> SEQUENCE: 31

Asp Ile Gln Met Thr Gln Ser Pro Ser Ser Leu Ser Ala Ser Val Gly
1               5                  10                  15

Asp Arg Val Thr Ile Thr Cys Arg Ala Ser Glu Asn Ile Tyr Tyr Ser
            20                  25                  30

Leu Ala Trp Tyr Gln Gln Lys Pro Gly Lys Ala Pro Lys Leu Leu Ile
        35                  40                  45

Tyr Asn Ala Asn Ser Leu Glu Asp Gly Val Pro Ser Arg Phe Ser Gly
    50                  55                  60

Ser Gly Ser Gly Thr Gln Tyr Thr Leu Thr Ile Ser Ser Leu Gln Pro
65                  70                  75                  80

Glu Asp Phe Ala Thr Tyr Tyr Cys Lys Gln Ala Tyr Asp Val Pro Tyr
                85                  90                  95

Thr Phe Gly Gln Gly Thr Lys Val Glu Ile Lys
            100                 105

<210> SEQ ID NO 32
<211> LENGTH: 5
<212> TYPE: PRT
<213> ORGANISM: Artificial Sequence
<220> FEATURE:
<223> OTHER INFORMATION: synthetically constructed CDRH1 of 1K11 (FERM
      BP-10510)

<400> SEQUENCE: 32

Asp Tyr Asn Met Asp
1               5

<210> SEQ ID NO 33
<211> LENGTH: 17
<212> TYPE: PRT
<213> ORGANISM: Artificial Sequence
<220> FEATURE:
<223> OTHER INFORMATION: synthetically constructed CDRH2 of 1K11 (FERM
      BP-10510)

<400> SEQUENCE: 33

Asp Ile Asn Pro Asn Asn Gly Gly Thr Ile Tyr Asn Gln Lys Phe Gln
1               5                  10                  15

Gly
```

```
<210> SEQ ID NO 34
<211> LENGTH: 8
<212> TYPE: PRT
<213> ORGANISM: Artificial Sequence
<220> FEATURE:
<223> OTHER INFORMATION: synthetically constructed CDRH3 of 1K11 (FERM
      BP-10510)

<400> SEQUENCE: 34

Ser Gly Val Ile Ser Thr Asp Tyr
1               5

<210> SEQ ID NO 35
<211> LENGTH: 348
<212> TYPE: DNA
<213> ORGANISM: Artificial Sequence
<220> FEATURE:
<223> OTHER INFORMATION: synthetically constructed VH of 1K11 (FERM
      BP-10510)

<400> SEQUENCE: 35
gtgcagctgc aggagtcagg acctgagctg gtgaagcctg ggcttcagt gaagataccc      60 tgcaaggctt ctggatacac attcactgac tacaacatgg actgggtgaa gcagagccat    120
ggaaagagcc ttgagtggat tggagatatt aatcctaaca acgtggtac aatctacaac     180 cagaagttcc agggcaaggc cacattgact gtagacaagt cctccagcac agcctacatg    240
gagctccgca gcctgacatc tgaggacact gcagtctatt actgtgcaag atcgggggtt    300
attagtacgg actactgggg ccaagggacc acggtcaccg tctcctca                 348

<210> SEQ ID NO 36
<211> LENGTH: 116
<212> TYPE: PRT
<213> ORGANISM: Artificial Sequence
<220> FEATURE:
<223> OTHER INFORMATION: synthetically constructed mature VH of 1K11
      (FERM BP-10510) starting from 2nd residue according to Kabat
      numbering

<400> SEQUENCE: 36

Val Gln Leu Gln Glu Ser Gly Pro Glu Leu Val Lys Pro Gly Ala Ser
1               5                   10                  15

Val Lys Ile Pro Cys Lys Ala Ser Gly Tyr Thr Phe Thr Asp Tyr Asn
            20                  25                  30

Met Asp Trp Val Lys Gln Ser His Gly Lys Ser Leu Glu Trp Ile Gly
        35                  40                  45

Asp Ile Asn Pro Asn Asn Gly Gly Thr Ile Tyr Asn Gln Lys Phe Gln
    50                  55                  60

Gly Lys Ala Thr Leu Thr Val Asp Lys Ser Ser Ser Thr Ala Tyr Met
65                  70                  75                  80

Glu Leu Arg Ser Leu Thr Ser Glu Asp Thr Ala Val Tyr Tyr Cys Ala
                85                  90                  95

Arg Ser Gly Val Ile Ser Thr Asp Tyr Trp Gly Gln Gly Thr Thr Val
            100                 105                 110

Thr Val Ser Ser
        115

<210> SEQ ID NO 37
<211> LENGTH: 11
<212> TYPE: PRT
<213> ORGANISM: Artificial Sequence
<220> FEATURE:
<223> OTHER INFORMATION: synthetically constructed CDRL1 of 1K11 (FERM
```

```
BP-10510)

<400> SEQUENCE: 37

Arg Ala Ser Gln Glu Ile Ser Gly Tyr Leu Ile
1               5                   10

<210> SEQ ID NO 38
<211> LENGTH: 7
<212> TYPE: PRT
<213> ORGANISM: Artificial Sequence
<220> FEATURE:
<223> OTHER INFORMATION: synthetically constructed CDRL2 of 1K11 (FERM
      BP-10510)

<400> SEQUENCE: 38

Ala Ala Ser Thr Leu Asp Ser
1               5

<210> SEQ ID NO 39
<211> LENGTH: 9
<212> TYPE: PRT
<213> ORGANISM: Artificial Sequence
<220> FEATURE:
<223> OTHER INFORMATION: synthetically constructed CDRL3 of 1K11 (FERM
      BP-10510)

<400> SEQUENCE: 39

Leu Gln Tyr Ala Asn Tyr Pro Pro Thr
1               5

<210> SEQ ID NO 40
<211> LENGTH: 324
<212> TYPE: DNA
<213> ORGANISM: Artificial Sequence
<220> FEATURE:
<223> OTHER INFORMATION: synthetically constructed VL of 1K11 (FERM
      BP-10510)

<400> SEQUENCE: 40
gacatccaga tgacacagtc tccaccctcc ctatctgcct ctctgggaga aagagtcagt    60
ctcacttgtc gggcaagtca ggaaattagt ggttacttaa tctggcttca acagaaacca   120
gatggaacta ttcaacgcct gatctacgcc gcatccactt tagattctgg tgtcccaaaa   180
aggttcagtg gcagtaggtc tgggtcagat tattctctca ccatcagcag ccttgagtct   240
gaagattttg cagactatta ctgtctacaa tatgctaatt atcctccgac gttcggtgga   300
ggcaccaagc tggaaatcaa acgg                                          324

<210> SEQ ID NO 41
<211> LENGTH: 108
<212> TYPE: PRT
<213> ORGANISM: Artificial Sequence
<220> FEATURE:
<223> OTHER INFORMATION: synthetically constructed mature VL of 1K11
      (FERM BP-10510)

<400> SEQUENCE: 41

Asp Ile Gln Met Thr Gln Ser Pro Pro Ser Leu Ser Ala Ser Leu Gly
1               5                   10                  15

Glu Arg Val Ser Leu Thr Cys Arg Ala Ser Gln Glu Ile Ser Gly Tyr
                20                  25                  30

Leu Ile Trp Leu Gln Gln Lys Pro Asp Gly Thr Ile Gln Arg Leu Ile
        35                  40                  45

Tyr Ala Ala Ser Thr Leu Asp Ser Gly Val Pro Lys Arg Phe Ser Gly
```

```
                       50                  55                  60
Ser Arg Ser Gly Ser Asp Tyr Ser Leu Thr Ile Ser Ser Leu Glu Ser
 65                  70                  75                  80

Glu Asp Phe Ala Asp Tyr Tyr Cys Leu Gln Tyr Ala Asn Tyr Pro Pro
                 85                  90                  95

Thr Phe Gly Gly Gly Thr Lys Leu Glu Ile Lys Arg
            100                 105
```

<210> SEQ ID NO 42
<211> LENGTH: 5
<212> TYPE: PRT
<213> ORGANISM: Artificial Sequence
<220> FEATURE:
<223> OTHER INFORMATION: synthetically constructed CDRH1 of 21C5 (FERM
      BP-10511)

<400> SEQUENCE: 42

```
Asp Tyr Tyr Met Tyr
1               5
```

<210> SEQ ID NO 43
<211> LENGTH: 17
<212> TYPE: PRT
<213> ORGANISM: Artificial Sequence
<220> FEATURE:
<223> OTHER INFORMATION: synthetically constructed CDRH2 of 21C5 (FERM
      BP-10511)

<400> SEQUENCE: 43

```
Thr Ile Ser Asp Gly Gly Asn Tyr Thr Tyr Tyr Pro Asp Ser Val Lys
1               5                   10                  15

Gly
```

<210> SEQ ID NO 44
<211> LENGTH: 10
<212> TYPE: PRT
<213> ORGANISM: Artificial Sequence
<220> FEATURE:
<223> OTHER INFORMATION: synthetically constructed CDRH3 of 21C5 (FERM
      BP-10511)

<400> SEQUENCE: 44

```
Asp Arg Asp Gly Ser Ser Leu Phe Ala Tyr
1               5                   10
```

<210> SEQ ID NO 45
<211> LENGTH: 354
<212> TYPE: DNA
<213> ORGANISM: Artificial Sequence
<220> FEATURE:
<223> OTHER INFORMATION: synthetically constructed VH of 21C5 (FERM
      BP-10511))

<400> SEQUENCE: 45

```
gtgcagctgc aggagtctgg gggaggctta gtgaagcctg agggtccct gaaactctcc      60 tgtgcagcct ctggattcac tttcagtgac tattacatgt attgggttcg ccagactccg    120
gaaaagaggc tggagtgggt cgcaaccatt agtgatggtg gtaattacac ctactatcca    180
gacagtgtga agggccgatt caccatctcc agagacaatg ccaagaataa cctgtacctg    240
caaatgagca gtctgaagtc tgaggacaca gccatgtatt actgtgcaag agatcgggac    300
ggtagtagcc tgtttgctta ctggggccaa gggaccacgg tcaccgtctc ctca          354
```

```
<210> SEQ ID NO 46
<211> LENGTH: 118
<212> TYPE: PRT
<213> ORGANISM: Artificial Sequence
<220> FEATURE:
<223> OTHER INFORMATION: synthetically constructed mature VH of 21C5
      (FERM BP-10511) starting from 2nd residue according to Kabat
      numbering

<400> SEQUENCE: 46

Val Gln Leu Gln Glu Ser Gly Gly Leu Val Lys Pro Gly Ser
1               5                   10                  15

Leu Lys Leu Ser Cys Ala Ala Ser Gly Phe Thr Phe Ser Asp Tyr Tyr
            20                  25                  30

Met Tyr Trp Val Arg Gln Thr Pro Glu Lys Arg Leu Glu Trp Val Ala
        35                  40                  45

Thr Ile Ser Asp Gly Gly Asn Tyr Thr Tyr Tyr Pro Asp Ser Val Lys
    50                  55                  60

Gly Arg Phe Thr Ile Ser Arg Asp Asn Ala Lys Asn Asn Leu Tyr Leu
65                  70                  75                  80

Gln Met Ser Ser Leu Lys Ser Glu Asp Thr Ala Met Tyr Tyr Cys Ala
                85                  90                  95

Arg Asp Arg Asp Gly Ser Ser Leu Phe Ala Tyr Trp Gly Gln Gly Thr
            100                 105                 110

Thr Val Thr Val Ser Ser
        115

<210> SEQ ID NO 47
<211> LENGTH: 11
<212> TYPE: PRT
<213> ORGANISM: Artificial Sequence
<220> FEATURE:
<223> OTHER INFORMATION: synthetically constructed CDRL1 of 21C5 (FERM
      BP-10511)

<400> SEQUENCE: 47

Lys Ala Ser Gln Asp Val Asn Ile Ala Val Ala
1               5                   10

<210> SEQ ID NO 48
<211> LENGTH: 7
<212> TYPE: PRT
<213> ORGANISM: Artificial Sequence
<220> FEATURE:
<223> OTHER INFORMATION: synthetically constructed CDRL2 of 21C5 (FERM
      BP-10511)

<400> SEQUENCE: 48

Trp Ala Ser Thr Arg His Thr
1               5

<210> SEQ ID NO 49
<211> LENGTH: 8
<212> TYPE: PRT
<213> ORGANISM: Artificial Sequence
<220> FEATURE:
<223> OTHER INFORMATION: synthetically constructed CDRL3 of 21C5 (FERM
      BP-10511)

<400> SEQUENCE: 49

Gln Gln His Tyr Asn Thr Pro Trp
1               5

<210> SEQ ID NO 50
```

<211> LENGTH: 321
<212> TYPE: DNA
<213> ORGANISM: Artificial Sequence
<220> FEATURE:
<223> OTHER INFORMATION: synthetically constructed VL of 21C5 (FERM BP-10511)

<400> SEQUENCE: 50

```
catccagatg acacagtctc caaattcatg tccacatcag taggagacag ggtcagcatc      60
acctgcaagg ccagtcagga tgtgaatatt gctgtagcct ggtatcaaca agaccaggg     120
caatctccta aactactgat ttactgggca tccacccggc acactggagt ccctgatcgc    180
ttcacaggca gtggatctgg gacagattat actctcacca tcagcagtgt gcaggctgaa    240
gacctggcac tttattactg tcagcaacat cataacactc cgtggacgtt cggtggaggc    300
accaagctgg aaatcaaacg g                                              321
```

<210> SEQ ID NO 51
<211> LENGTH: 107
<212> TYPE: PRT
<213> ORGANISM: Artificial Sequence
<220> FEATURE:
<223> OTHER INFORMATION: synthetically constructed mature VL of 21C5 (FERM BP-10511)

<400> SEQUENCE: 51

```
His Pro Asp Asp Thr Val Ser Lys Phe Met Ser Thr Ser Val Gly Asp
1               5                   10                  15
Arg Val Ser Ile Thr Cys Lys Ala Ser Gln Asp Val Asn Ile Ala Val
            20                  25                  30
Ala Trp Tyr Gln Gln Arg Pro Gly Gln Ser Pro Lys Leu Leu Ile Tyr
        35                  40                  45
Trp Ala Ser Thr Arg His Thr Gly Val Pro Asp Arg Phe Thr Gly Ser
    50                  55                  60
Gly Ser Gly Thr Asp Tyr Thr Leu Thr Ile Ser Ser Val Gln Ala Glu
65                  70                  75                  80
Asp Leu Ala Leu Tyr Tyr Cys Gln Gln His Tyr Asn Thr Pro Trp Thr
                85                  90                  95
Phe Gly Gly Gly Thr Lys Leu Glu Ile Lys Arg
            100                 105
```

<210> SEQ ID NO 52
<211> LENGTH: 5
<212> TYPE: PRT
<213> ORGANISM: Artificial Sequence
<220> FEATURE:
<223> OTHER INFORMATION: synthetically constructed CDRH1 of 25B6 (FERM BP-10513)

<400> SEQUENCE: 52

```
Ser Tyr Gly Val His
1               5
```

<210> SEQ ID NO 53
<211> LENGTH: 16
<212> TYPE: PRT
<213> ORGANISM: Artificial Sequence
<220> FEATURE:
<223> OTHER INFORMATION: synthetically constructed CDRH2 of 25B6 (FERM BP-10513)

<400> SEQUENCE: 53

```
Val Ile Trp Ser Gly Gly Ser Thr Asn Tyr Asn Ser Ala Leu Met Ser
```

-continued

<210> SEQ ID NO 54
<211> LENGTH: 10
<212> TYPE: PRT
<213> ORGANISM: Artificial Sequence
<220> FEATURE:
<223> OTHER INFORMATION: synthetically constructed CDRH3 of 25B6 (FERM BP-10513)

<400> SEQUENCE: 54

```
Asp Tyr Gly Asn Tyr Pro Trp Phe Ala Tyr
1               5                   10
```

<210> SEQ ID NO 55
<211> LENGTH: 351
<212> TYPE: DNA
<213> ORGANISM: Artificial Sequence
<220> FEATURE:
<223> OTHER INFORMATION: synthetically constructed VH of 25B6 (FERM BP-10513)

<400> SEQUENCE: 55

```
gtcaagctgc agcagtctgg acctggcctg gtggcgccct cacagagcct gtccatcact    60
tgcactgtct ctgggttttc attaaccagt tatggtgtac actgggttcg ccagcctcca   120
ggaaagggtc tggagtggct gggagtaata tggtctggtg aagcacaaa ttataattcg    180
gctctcatgt ccagactgag catcagtaaa gacaatttta gagccaagt tttcttaaaa    240
atgaacagtc tgcaaactga tgacacagcc atatactact gtgccagaga ctatggtaac   300
taccccctggt ttgcttactg gggccaaggg accacggtca ccgtctcctc a           351
```

<210> SEQ ID NO 56
<211> LENGTH: 116
<212> TYPE: PRT
<213> ORGANISM: Artificial Sequence
<220> FEATURE:
<223> OTHER INFORMATION: synthetically constructed mature VH of 25B6 (FERM BP-10513) starting from 2nd residue according to Kabat numbering

<400> SEQUENCE: 56

```
Val Lys Leu Gln Gln Ser Gly Pro Gly Leu Val Ala Pro Ser Gln Ser
1               5                   10                  15

Leu Ser Ile Thr Cys Thr Val Ser Gly Phe Ser Leu Thr Ser Tyr Gly
            20                  25                  30

Val His Trp Val Arg Gln Pro Pro Gly Lys Gly Leu Glu Trp Leu Gly
        35                  40                  45

Val Ile Trp Ser Gly Gly Ser Thr Asn Tyr Asn Ser Ala Leu Met Ser
    50                  55                  60

Arg Leu Ser Ile Ser Lys Asp Asn Phe Lys Ser Gln Val Phe Leu Lys
65                  70                  75                  80

Met Asn Ser Leu Gln Thr Asp Asp Thr Ala Ile Tyr Tyr Cys Ala Arg
                85                  90                  95

Asp Tyr Gly Asn Tyr Pro Trp Phe Ala Tyr Trp Gly Gln Gly Thr Thr
            100                 105                 110

Val Thr Val Ser
        115
```

<210> SEQ ID NO 57
<211> LENGTH: 11
<212> TYPE: PRT

```
<213> ORGANISM: Artificial Sequence
<220> FEATURE:
<223> OTHER INFORMATION: synthetically constructed CDRL1 of 25B6 (FERM
      BP-10513)

<400> SEQUENCE: 57

Lys Ala Ser Gln Asp Val Asn Thr Ala Val Ala
1               5                   10

<210> SEQ ID NO 58
<211> LENGTH: 7
<212> TYPE: PRT
<213> ORGANISM: Artificial Sequence
<220> FEATURE:
<223> OTHER INFORMATION: synthetically constructed CDRL2 of 25B6 (FERM
      BP-10513)

<400> SEQUENCE: 58

Ser Ala Ser Tyr Arg Tyr Thr
1               5

<210> SEQ ID NO 59
<211> LENGTH: 9
<212> TYPE: PRT
<213> ORGANISM: Artificial Sequence
<220> FEATURE:
<223> OTHER INFORMATION: synthetically constructed CDRL3 of 25B6 (FERM
      BP-10513)

<400> SEQUENCE: 59

Gln Gln His Tyr Ser Thr Pro Cys Ala
1               5

<210> SEQ ID NO 60
<211> LENGTH: 321
<212> TYPE: DNA
<213> ORGANISM: Artificial Sequence
<220> FEATURE:
<223> OTHER INFORMATION: synthetically constructed VL of 25B6 (FERM
      BP-10513)

<400> SEQUENCE: 60
catccagatg acacagtctc caaattcatg tccacatcag taggagacag ggtcagcatc      60
acctgcaagg ccagtcagga tgtgaatact gctgtggcct ggtatcaaca gaaaccagga     120
caatccccta aactactgat ttactcggca tcctaccggt acactggagt ccctgatcgc     180
ttcactggca gtggatctgg gacggatttc actttcacca tcagcagtgt gcaggctgaa     240
gacctggcag tttattactg tcagcaacat tatagtactc cgtgcgcgtt cggagggggg     300
acaaagttgg aaataaaacg g                                               321

<210> SEQ ID NO 61
<211> LENGTH: 107
<212> TYPE: PRT
<213> ORGANISM: Artificial Sequence
<220> FEATURE:
<223> OTHER INFORMATION: synthetically constructed mature VL of 25B6
      (FERM BP-10513)

<400> SEQUENCE: 61

His Pro Asp Asp Thr Val Ser Lys Phe Met Ser Thr Ser Val Gly Asp
1               5                   10                  15

Arg Val Ser Ile Thr Cys Lys Ala Ser Gln Asp Val Asn Thr Ala Val
            20                  25                  30

Ala Trp Tyr Gln Gln Lys Pro Gly Gln Ser Pro Lys Leu Leu Ile Tyr
```

```
                35                  40                  45
Ser Ala Ser Tyr Arg Tyr Thr Gly Val Pro Asp Arg Phe Thr Gly Ser
        50                  55                  60

Gly Ser Gly Thr Asp Phe Thr Phe Thr Ile Ser Ser Val Gln Ala Glu
65                  70                  75                  80

Asp Leu Ala Val Tyr Tyr Cys Gln Gln His Tyr Ser Thr Pro Cys Ala
                85                  90                  95

Phe Gly Gly Gly Thr Lys Leu Glu Ile Lys Arg
            100                 105

<210> SEQ ID NO 62
<211> LENGTH: 5
<212> TYPE: PRT
<213> ORGANISM: Artificial Sequence
<220> FEATURE:
<223> OTHER INFORMATION: synthetically constructed CDRH1 of 28S1 (FERM
      BP-10832)

<400> SEQUENCE: 62

Gly Tyr Gly Val Asn
1               5

<210> SEQ ID NO 63
<211> LENGTH: 16
<212> TYPE: PRT
<213> ORGANISM: Artificial Sequence
<220> FEATURE:
<223> OTHER INFORMATION: synthetically constructed CDRH2 of 28S1 (FERM
      BP-10832)

<400> SEQUENCE: 63

Met Ile Trp Gly Asp Gly Ile Thr Glu Tyr Asn Ser Ala Leu Lys Ser
1               5                   10                  15

<210> SEQ ID NO 64
<211> LENGTH: 10
<212> TYPE: PRT
<213> ORGANISM: Artificial Sequence
<220> FEATURE:
<223> OTHER INFORMATION: synthetically constructed CDRH3 of 28S1 (FERM
      BP-10832)

<400> SEQUENCE: 64

Arg Asp Ala Ser Ser Gly Tyr Gly Phe Ala
1               5                   10

<210> SEQ ID NO 65
<211> LENGTH: 353
<212> TYPE: DNA
<213> ORGANISM: Artificial Sequence
<220> FEATURE:
<223> OTHER INFORMATION: synthetically constructed VH of 28S1 (FERM
      BP-10832)

<400> SEQUENCE: 65
aggtgaagct gcaggagtca ggacctggcc tggtggcgcc ctcacagagc ctgtccatca     60
catgcaccgt ctcagggttc tcattaaccg gctatggtgt aaactgggtt cgccagcctc    120
caggaaaggg tctggagtgg ctgggaatga tatggggtga tggaatcaca gagtataatt    180
cagctctcaa atccagactg agcatcagca ggacaactc caagagccaa gttttcttaa    240
aaatgaacag tctgcaaact gatgacacag ccagtacta ctgtgccaga gatgccagct    300
cgggctacgg gtttgcttac tggggccaag ggaccacggt caccgtctcc tca          353
```

<210> SEQ ID NO 66
<211> LENGTH: 117
<212> TYPE: PRT
<213> ORGANISM: Artificial Sequence
<220> FEATURE:
<223> OTHER INFORMATION: synthetically constructed mature VH of 28S1
      (FERM BP-10832) starting from 2nd residue according to Kabat
      numbering

<400> SEQUENCE: 66

```
Val Lys Leu Gln Glu Ser Gly Pro Gly Leu Val Ala Pro Ser Gln Ser
1               5                   10                  15

Leu Ser Ile Thr Cys Thr Val Ser Gly Phe Ser Leu Thr Gly Tyr Gly
            20                  25                  30

Val Asn Trp Val Arg Gln Pro Pro Gly Lys Gly Leu Glu Trp Leu Gly
        35                  40                  45

Met Ile Trp Gly Asp Gly Ile Thr Glu Tyr Asn Ser Ala Leu Lys Ser
    50                  55                  60

Arg Leu Ser Ile Ser Lys Asp Asn Ser Lys Ser Gln Val Phe Leu Lys
65                  70                  75                  80

Met Asn Ser Leu Gln Thr Asp Asp Thr Ala Arg Tyr Tyr Cys Ala Arg
                85                  90                  95

Asp Ala Ser Ser Gly Tyr Gly Phe Ala Tyr Trp Gly Gln Gly Thr Thr
            100                 105                 110

Val Thr Val Ser Ser
        115
```

<210> SEQ ID NO 67
<211> LENGTH: 12
<212> TYPE: PRT
<213> ORGANISM: Artificial Sequence
<220> FEATURE:
<223> OTHER INFORMATION: synthetically constructed CDRL1 of 28S1 (FERM
      BP-10832)

<400> SEQUENCE: 67

```
Thr Ala Ser Ser Ser Val Ser Ser Ser Tyr Leu His
1               5                   10
```

<210> SEQ ID NO 68
<211> LENGTH: 7
<212> TYPE: PRT
<213> ORGANISM: Artificial Sequence
<220> FEATURE:
<223> OTHER INFORMATION: synthetically constructed CDRL2 of 28S1 (FERM
      BP-10832)

<400> SEQUENCE: 68

```
Ser Thr Ser Asn Leu Ala Ser
1               5
```

<210> SEQ ID NO 69
<211> LENGTH: 9
<212> TYPE: PRT
<213> ORGANISM: Artificial Sequence
<220> FEATURE:
<223> OTHER INFORMATION: synthetically constructed CDRL3 of 28S1 (FERM
      BP-10832)

<400> SEQUENCE: 69

```
His Gln Tyr His Arg Ser Pro Tyr Thr
1               5
```

-continued

```
<210> SEQ ID NO 70
<211> LENGTH: 327
<212> TYPE: DNA
<213> ORGANISM: Artificial Sequence
<220> FEATURE:
<223> OTHER INFORMATION: synthetically constructed VL of 28S1 (FERM
      BP-10832)

<400> SEQUENCE: 70
tacattgtgc tgacccagtc tccagcaatc atgtctgcat ctctagggga acgggtcacc      60
atgacctgca ctgccagctc aagtgtaagt tccagttact gcactggta ccagcagaag     120 ccaggatcct cccccaaact ctggatttat agcacatcca acctggcttc tggagtccca     180
gctcgcttca gtggcagtgg gtctgggacc tcttactctc tcacaatcag cagcatggag     240
gctgaagatg ctgccactta ttactgccac cagtatcatc gttccccgta cacgttcgga     300 gggggacaa agttggaaat aaaacgg                                          327

<210> SEQ ID NO 71
<211> LENGTH: 109
<212> TYPE: PRT
<213> ORGANISM: Artificial Sequence
<220> FEATURE:
<223> OTHER INFORMATION: synthetically constructed mature VL of 28S1
      (FERM BP-10832)

<400> SEQUENCE: 71

Tyr Ile Val Leu Thr Gln Ser Pro Ala Ile Met Ser Ala Ser Leu Gly
1               5                  10                  15

Glu Arg Val Thr Met Thr Cys Thr Ala Ser Ser Val Ser Ser Ser
            20                  25                  30

Tyr Leu His Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Gln Tyr His Arg Ser Pro
                85                  90                  95

Tyr Thr Phe Gly Gly Gly Thr Lys Leu Glu Ile Lys Arg
            100                 105

<210> SEQ ID NO 72
<211> LENGTH: 451
<212> TYPE: DNA
<213> ORGANISM: Artificial Sequence
<220> FEATURE:
<223> OTHER INFORMATION: synthetically constructed VH of 24I11 (FERM
      BP-10512)
<220> FEATURE:
<221> NAME/KEY: misc_feature
<222> LOCATION: (1)...(57)
<223> OTHER INFORMATION: sequence encoding signal peptide
<220> FEATURE:
<221> NAME/KEY: misc_feature
<222> LOCATION: (1)...(6)
<223> OTHER INFORMATION: SpeI site
<220> FEATURE:
<221> NAME/KEY: misc_feature
<222> LOCATION: (446)...(451)
<223> OTHER INFORMATION: HindIII site

<400> SEQUENCE: 72
actagtacca ccatgaaatg cagctgggtt atcttcttcc tgatggcagt ggttacaggg      60
```

```
gtcaattcag aggttcagct gcagcagtct ggggcagagc ttgtgaagcc aggggcctca    120
gtcaagttgt cctgcacagc ttctggcttc aacattaaag acacctatgt gcactgggtg    180
aagcagaggc ctgaacaggg cctggagtgg attggaaata ttgatcctgc gaatggtaat    240
actaaatatg acccgaagtt ccagggcaag gccactataa cagcagacac atcctccaac    300
acagcctacc tgcacctcag cagcctgaca tctgaggaca ctgccgtcta ttactgtgct    360
agatggttac gacatttta ctatgctatg gactactggg gtcaaggaac ctcagtcacc    420
gtctcctcag gtaagaatgg cctctaagct t                                   451
```

<210> SEQ ID NO 73
<211> LENGTH: 416
<212> TYPE: DNA
<213> ORGANISM: Artificial Sequence
<220> FEATURE:
<223> OTHER INFORMATION: synthetically constructed VL of 24I11 (FERM
      BP-10512)
<220> FEATURE:
<221> NAME/KEY: misc_feature
<222> LOCATION: (1)...(60)
<223> OTHER INFORMATION: sequence encoding signal peptide
<220> FEATURE:
<221> NAME/KEY: misc_feature
<222> LOCATION: (1)...(6)
<223> OTHER INFORMATION: NheI site
<220> FEATURE:
<221> NAME/KEY: misc_feature
<222> LOCATION: (411)...(416)
<223> OTHER INFORMATION: EcoRI site

<400> SEQUENCE: 73

```
gctagcacca ccatgagtgt gcccactcaa ctcctggggt tgctgctgct gtggcttaca     60
gacgcaggat gtgacatcca gatgactcag tctccagcct ccctggctgc atctgtggga    120
gaaactgtca ccgacatcca gatgactcag tctccagcct ccctggctgc atctgtggga    180
gaaactgtca ccgggaaatc tcctcagctc ctgatctata tgcaaacag cttggaagat    240 ggtgtcccat cgaggttcag tggcagtgga tctgggacac agtattctat gaagatcaac    300
agcatgcagc ctgaagatac cgcaacttat ttctgtaaac aggcttatga cgttccgtac    360
acgttcggag gggggaccaa gctggaaata aaacgtaagt agtcttctca gaattc        416
```

<210> SEQ ID NO 74
<211> LENGTH: 450
<212> TYPE: DNA
<213> ORGANISM: Artificial Sequence
<220> FEATURE:
<223> OTHER INFORMATION: synthetically constructed Hu24I11 VH gene
<220> FEATURE:
<221> NAME/KEY: misc_feature
<222> LOCATION: (1)...(6)
<223> OTHER INFORMATION: SpeI site
<220> FEATURE:
<221> NAME/KEY: misc_feature
<222> LOCATION: (445)...(450)
<223> OTHER INFORMATION: HindIII site

<400> SEQUENCE: 74

```
actagtacca ccatgaaatg cagctgggtt atcttcttcc tgatggcagt ggttacaggg     60
gtcaattcac aggttcagct ggtgcagtct ggggcagagg tgaagaagcc aggggcctca    120
gtcaaggttt cctgcaaggc ttctggcttc aacattaaag acacctatgt gcactgggtg    180
cgccaggccc ctggacagag gctggagtgg attggaaata ttgatcctgc gaatggtaat    240
actaaatatg acccgaagtt ccagggcaag gccactataa cagcagacac atccgcgagc    300
```

```
acagcctaca tggagctcag cagcctgaga tctgaggaca ctgccgtcta ttactgtgct    360
agatggttac gacatttttta ctatgctatg gactactggg gtcaaggaac cctggtcacc    420
gtctcctcag gtgagtcctc acaaaagctt                                     450
```

<210> SEQ ID NO 75
<211> LENGTH: 416
<212> TYPE: DNA
<213> ORGANISM: Artificial Sequence
<220> FEATURE:
<223> OTHER INFORMATION: synthetically constructed Hu24I11 VL gene

<400> SEQUENCE: 75

```
gctagcacca ccatgagtgt gcccactcaa ctcctggggt tgctgctgct gtggcttaca     60
gacgcacgat gtgacatcca gatgactcag tctccatcct ccctgtctgc atctgtggga    120
gacagagtca ccatcacatg tcgagcaagt gagaacattt actacagttt agcatggtat    180
cagcagaagc cagggaaagc ccctaagctc ctgatctata atgcaaacag cttggaagat    240
ggtgtcccat cgaggttcag tggcagtgga tctgggacac agtatactct caccatcagc    300
agcctgcagc ctgaagattt tgcaacttat tactgtaaac aggcttatga cgttccgtac    360
acgttcggac aagggaccaa ggtggaaatc aaacgtgagt agaatttaaa gaattc        416
```

<210> SEQ ID NO 76
<211> LENGTH: 1035
<212> TYPE: PRT
<213> ORGANISM: Homo sapiens
<220> FEATURE:
<221> NAME/KEY: SIGNAL
<222> LOCATION: (1)...(29)
<223> OTHER INFORMATION: signal peptide
<220> FEATURE:
<221> NAME/KEY: misc_feature
<222> LOCATION: (1)...(1035)
<223> OTHER INFORMATION: Human alpha9 integrin

<400> SEQUENCE: 76

```
Met Gly Gly Pro Ala Ala Pro Arg Gly Ala Gly Arg Leu Arg Ala Leu
1               5                   10                  15

Leu Leu Ala Leu Val Val Ala Gly Ile Pro Ala Gly Ala Tyr Asn Leu
            20                  25                  30

Asp Pro Gln Arg Pro Val His Phe Gln Gly Pro Ala Asp Ser Phe Phe
        35                  40                  45

Gly Tyr Ala Val Leu Glu His Phe His Asp Asn Thr Arg Trp Val Leu
    50                  55                  60

Val Gly Ala Pro Lys Ala Asp Ser Lys Tyr Ser Pro Ser Val Lys Ser
65                  70                  75                  80

Pro Gly Ala Val Phe Lys Cys Arg Val His Thr Asn Pro Asp Arg Arg
                85                  90                  95

Cys Thr Glu Leu Asp Met Ala Arg Gly Lys Asn Arg Gly Thr Ser Cys
            100                 105                 110

Gly Lys Thr Cys Arg Glu Asp Arg Asp Asp Glu Trp Met Gly Val Ser
        115                 120                 125

Leu Ala Arg Gln Pro Lys Ala Asp Gly Arg Val Leu Ala Cys Ala His
    130                 135                 140

Arg Trp Lys Asn Ile Tyr Tyr Glu Ala Asp His Ile Leu Pro His Gly
145                 150                 155                 160

Phe Cys Tyr Ile Ile Pro Ser Asn Leu Gln Ala Lys Gly Arg Thr Leu
                165                 170                 175
```

```
Ile Pro Cys Tyr Glu Glu Tyr Lys Lys Lys Tyr Gly Glu His Gly
            180                 185                 190

Ser Cys Gln Ala Gly Ile Ala Gly Phe Phe Thr Glu Glu Leu Val Val
        195                 200                 205

Met Gly Ala Pro Gly Ser Phe Tyr Trp Ala Gly Thr Ile Lys Val Leu
    210                 215                 220

Asn Leu Thr Asp Asn Thr Tyr Leu Lys Leu Asn Asp Glu Val Ile Met
225                 230                 235                 240

Asn Arg Arg Tyr Thr Tyr Leu Gly Tyr Ala Val Thr Ala Gly His Phe
                245                 250                 255

Ser His Pro Ser Thr Ile Asp Val Val Gly Gly Ala Pro Gln Asp Lys
            260                 265                 270

Gly Ile Gly Lys Val Tyr Ile Phe Arg Ala Asp Arg Ser Gly Thr
        275                 280                 285

Leu Ile Lys Ile Phe Gln Ala Ser Gly Lys Lys Met Gly Ser Tyr Phe
    290                 295                 300

Gly Ser Ser Leu Cys Ala Val Asp Leu Asn Gly Asp Gly Leu Ser Asp
305                 310                 315                 320

Leu Leu Val Gly Ala Pro Met Phe Ser Glu Ile Arg Asp Glu Gly Gln
                325                 330                 335

Val Thr Val Tyr Ile Asn Arg Gly Asn Gly Ala Leu Glu Glu Gln Leu
            340                 345                 350

Ala Leu Thr Gly Asp Gly Ala Tyr Asn Ala His Phe Gly Glu Ser Ile
        355                 360                 365

Ala Ser Leu Asp Asp Leu Asp Asn Asp Gly Phe Pro Asp Val Ala Ile
370                 375                 380

Gly Ala Pro Lys Glu Asp Asp Phe Ala Gly Ala Val Tyr Ile Tyr His
385                 390                 395                 400

Gly Asp Ala Gly Gly Ile Val Pro Gln Tyr Ser Met Lys Leu Ser Gly
                405                 410                 415

Gln Lys Ile Asn Pro Val Leu Arg Met Phe Gly Gln Ser Ile Ser Gly
            420                 425                 430

Gly Ile Asp Met Asp Gly Asn Gly Tyr Pro Asp Val Thr Val Gly Ala
        435                 440                 445

Phe Met Ser Asp Ser Val Val Leu Leu Arg Ala Arg Pro Val Ile Thr
    450                 455                 460

Val Asp Val Ser Ile Phe Leu Pro Gly Ser Ile Asn Ile Thr Ala Pro
465                 470                 475                 480

Gln Cys His Asp Gly Gln Gln Pro Val Asn Cys Leu Asn Val Thr Thr
                485                 490                 495

Cys Phe Ser Phe His Gly Lys His Val Pro Gly Glu Ile Gly Leu Asn
            500                 505                 510

Tyr Val Leu Met Ala Asp Val Ala Lys Lys Glu Lys Gly Gln Met Pro
        515                 520                 525

Arg Val Tyr Phe Val Leu Leu Gly Glu Thr Met Gly Asn Val Thr Glu
    530                 535                 540

Lys Leu Gln Leu Thr Tyr Met Glu Glu Thr Cys Arg His Tyr Val Ala
545                 550                 555                 560

His Val Lys Arg Arg Val Gln Asp Val Ile Ser Pro Ile Val Phe Glu
                565                 570                 575

Ala Ala Tyr Ser Leu Ser Glu His Val Thr Gly Glu Glu Arg Glu
            580                 585                 590

Leu Pro Pro Leu Thr Pro Val Leu Arg Trp Lys Lys Gly Gln Lys Ile
```

-continued

```
                595                 600                 605
Ala Gln Lys Asn Gln Thr Val Phe Glu Arg Asn Cys Arg Ser Glu Asp
610                 615                 620
Cys Ala Ala Asp Leu Gln Leu Gln Gly Lys Leu Leu Leu Ser Ser Met
625                 630                 635                 640
Asp Glu Lys Thr Leu Tyr Leu Ala Leu Gly Ala Val Lys Asn Ile Ser
                645                 650                 655
Leu Asn Ile Ser Ile Ser Asn Leu Gly Asp Asp Ala Tyr Asp Ala Asn
                660                 665                 670
Val Ser Phe Asn Val Ser Arg Glu Leu Phe Phe Ile Asn Met Trp Gln
                675                 680                 685
Lys Glu Glu Met Gly Ile Ser Cys Glu Leu Leu Glu Ser Asp Phe Leu
690                 695                 700
Lys Cys Ser Val Gly Phe Pro Phe Met Arg Ser Lys Ser Lys Tyr Glu
705                 710                 715                 720
Phe Ser Val Ile Phe Asp Thr Ser His Leu Ser Gly Glu Glu Val
                725                 730                 735
Leu Ser Phe Ile Val Thr Ala Gln Ser Gly Asn Thr Glu Arg Ser Glu
                740                 745                 750
Ser Leu His Asp Asn Thr Leu Val Leu Met Val Pro Leu Met His Glu
                755                 760                 765
Val Asp Thr Ser Ile Thr Gly Ile Met Ser Pro Thr Ser Phe Val Tyr
770                 775                 780
Gly Glu Ser Val Asp Ala Ala Asn Phe Ile Gln Leu Asp Asp Leu Glu
785                 790                 795                 800
Cys His Phe Gln Pro Ile Asn Ile Thr Leu Gln Val Tyr Asn Thr Gly
                805                 810                 815
Pro Ser Thr Leu Pro Gly Ser Ser Val Ser Ile Ser Phe Pro Asn Arg
                820                 825                 830
Leu Ser Ser Gly Gly Ala Glu Met Phe His Val Gln Glu Met Val Val
                835                 840                 845
Gly Gln Glu Lys Gly Asn Cys Ser Phe Gln Lys Asn Pro Thr Pro Cys
850                 855                 860
Ile Ile Pro Gln Glu Gln Asn Ile Phe His Thr Ile Phe Ala Phe
865                 870                 875                 880
Phe Thr Lys Ser Gly Arg Lys Val Leu Asp Cys Glu Lys Pro Gly Ile
                885                 890                 895
Ser Cys Leu Thr Ala His Cys Asn Phe Ser Ala Leu Ala Lys Glu Glu
                900                 905                 910
Ser Arg Thr Ile Asp Ile Tyr Met Leu Leu Asn Thr Glu Ile Leu Lys
                915                 920                 925
Lys Asp Ser Ser Ser Val Ile Gln Phe Met Ser Arg Ala Lys Val Lys
930                 935                 940
Val Asp Pro Ala Leu Arg Val Val Glu Ile Ala His Gly Asn Pro Glu
945                 950                 955                 960
Glu Val Thr Val Val Phe Glu Ala Leu His Asn Leu Glu Pro Arg Gly
                965                 970                 975
Tyr Val Val Gly Trp Ile Ala Ile Ser Leu Leu Val Gly Ile Leu
                980                 985                 990
Ile Phe Leu Leu Leu Ala Val Leu  Leu Trp Lys Met Gly  Phe Phe Arg
                995                  1000                 1005
Arg Arg  Tyr Lys Glu Ile Ile  Glu Ala Glu Lys Asn  Arg Lys Glu
     1010                1015                1020
```

```
Asn Glu  Asp Ser Trp Asp Trp  Val Gln Lys Asn Gln
    1025            1030             1035
```

<210> SEQ ID NO 77
<211> LENGTH: 12
<212> TYPE: PRT
<213> ORGANISM: Homo sapiens
<220> FEATURE:
<221> NAME/KEY: misc_feature
<222> LOCATION: (1)...(12)
<223> OTHER INFORMATION: Partial aa sequence of human alpha9 integrin

<400> SEQUENCE: 77

```
Phe Gln Gly Pro Ala Asp Ser Phe Phe Gly Tyr Ala
1               5                   10
```

<210> SEQ ID NO 78
<211> LENGTH: 18
<212> TYPE: PRT
<213> ORGANISM: Homo sapiens
<220> FEATURE:
<221> NAME/KEY: misc_feature
<222> LOCATION: (1)...(18)
<223> OTHER INFORMATION: Partial aa sequence of human alpha9 integrin

<400> SEQUENCE: 78

```
Lys Ser Pro Gly Ala Val Phe Lys Cys Arg Val His Thr Asn Pro Asp
1               5                   10                  15

Arg Arg
```

<210> SEQ ID NO 79
<211> LENGTH: 18
<212> TYPE: PRT
<213> ORGANISM: Homo sapiens
<220> FEATURE:
<221> NAME/KEY: misc_feature
<222> LOCATION: (1)...(18)
<223> OTHER INFORMATION: Partial aa sequence of human alpha9 integrin

<400> SEQUENCE: 79

```
Trp Met Gly Val Ser Leu Ala Arg Gln Pro Lys Ala Asp Gly Arg Val
1               5                   10                  15

Leu Ala
```

<210> SEQ ID NO 80
<211> LENGTH: 15
<212> TYPE: PRT
<213> ORGANISM: Homo sapiens
<220> FEATURE:
<221> NAME/KEY: misc_feature
<222> LOCATION: (1)...(15)
<223> OTHER INFORMATION: Partial aa sequence of human alpha9 integrin

<400> SEQUENCE: 80

```
Cys Ala His Arg Trp Lys Asn Ile Tyr Tyr Glu Ala Asp His Ile
1               5                   10                  15
```

<210> SEQ ID NO 81
<211> LENGTH: 18
<212> TYPE: PRT
<213> ORGANISM: Homo sapiens
<220> FEATURE:
<221> NAME/KEY: misc_feature
<222> LOCATION: (1)...(18)
<223> OTHER INFORMATION: Partial aa sequence of human alpha9 integrin

<400> SEQUENCE: 81

```
Gly Phe Cys Tyr Ile Ile Pro Ser Asn Leu Gln Ala Lys Gly Arg Thr
1               5                   10                  15

Leu Ile

<210> SEQ ID NO 82
<211> LENGTH: 18
<212> TYPE: PRT
<213> ORGANISM: Homo sapiens
<220> FEATURE:
<221> NAME/KEY: misc_feature
<222> LOCATION: (1)...(18)
<223> OTHER INFORMATION: Partial aa sequence of human alpha9 integrin

<400> SEQUENCE: 82

Val Met Gly Ala Pro Gly Ser Phe Tyr Trp Ala Gly Thr Ile Lys Val
1               5                   10                  15

Leu Asn

<210> SEQ ID NO 83
<211> LENGTH: 15
<212> TYPE: PRT
<213> ORGANISM: Homo sapiens
<220> FEATURE:
<221> NAME/KEY: misc_feature
<222> LOCATION: (1)...(15)
<223> OTHER INFORMATION: Partial aa sequence of human alpha9 integrin

<400> SEQUENCE: 83

Val Ile Met Asn Arg Arg Tyr Thr Tyr Leu Gly Tyr Ala Val Thr
1               5                   10                  15

<210> SEQ ID NO 84
<211> LENGTH: 18
<212> TYPE: PRT
<213> ORGANISM: Homo sapiens
<220> FEATURE:
<221> NAME/KEY: misc_feature
<222> LOCATION: (1)...(18)
<223> OTHER INFORMATION: Partial aa sequence of human alpha9 integrin

<400> SEQUENCE: 84

Val Tyr Ile Phe Arg Ala Asp Arg Arg Ser Gly Thr Leu Ile Lys Ile
1               5                   10                  15

Phe Gln

<210> SEQ ID NO 85
<211> LENGTH: 24
<212> TYPE: PRT
<213> ORGANISM: Homo sapiens
<220> FEATURE:
<221> NAME/KEY: misc_feature
<222> LOCATION: (1)...(24)
<223> OTHER INFORMATION: Partial aa sequence of human alpha9 integrin

<400> SEQUENCE: 85

Gln Tyr Ser Met Lys Leu Ser Gly Gln Lys Ile Asn Pro Val Leu Arg
1               5                   10                  15

Met Phe Gly Gln Ser Ile Ser Gly
            20

<210> SEQ ID NO 86
<211> LENGTH: 18
<212> TYPE: PRT
<213> ORGANISM: Homo sapiens
<220> FEATURE:
```

```
<221> NAME/KEY: misc_feature
<222> LOCATION: (1)...(18)
<223> OTHER INFORMATION: Partial aa sequence of human alpha9 integrin

<400> SEQUENCE: 86

Val Val Leu Leu Arg Ala Arg Pro Val Ile Thr Val Asp Val Ser Ile
1               5                   10                  15

Phe Leu

<210> SEQ ID NO 87
<211> LENGTH: 18
<212> TYPE: PRT
<213> ORGANISM: Homo sapiens
<220> FEATURE:
<221> NAME/KEY: misc_feature
<222> LOCATION: (1)...(18)
<223> OTHER INFORMATION: Partial aa sequence of human alpha9 integrin

<400> SEQUENCE: 87

Arg His Tyr Val Ala His Val Lys Arg Arg Val Gln Asp Val Ile Ser
1               5                   10                  15

Pro Ile

<210> SEQ ID NO 88
<211> LENGTH: 30
<212> TYPE: PRT
<213> ORGANISM: Homo sapiens
<220> FEATURE:
<221> NAME/KEY: misc_feature
<222> LOCATION: (1)...(30)
<223> OTHER INFORMATION: Partial aa sequence of human alpha9 integrin

<400> SEQUENCE: 88

Glu Leu Pro Pro Leu Thr Pro Val Leu Arg Trp Lys Lys Gly Gln Lys
1               5                   10                  15

Ile Ala Gln Lys Asn Gln Thr Val Phe Glu Arg Asn Cys Arg
                20                  25                  30

<210> SEQ ID NO 89
<211> LENGTH: 12
<212> TYPE: PRT
<213> ORGANISM: Homo sapiens
<220> FEATURE:
<221> NAME/KEY: misc_feature
<222> LOCATION: (1)...(12)
<223> OTHER INFORMATION: Partial aa sequence of human alpha9 integrin

<400> SEQUENCE: 89

Tyr Leu Ala Leu Gly Ala Val Lys Asn Ile Ser Leu
1               5                   10

<210> SEQ ID NO 90
<211> LENGTH: 18
<212> TYPE: PRT
<213> ORGANISM: Homo sapiens
<220> FEATURE:
<221> NAME/KEY: misc_feature
<222> LOCATION: (1)...(18)
<223> OTHER INFORMATION: Partial aa sequence of human alpha9 integrin

<400> SEQUENCE: 90

Cys Ser Val Gly Phe Pro Phe Met Arg Ser Lys Ser Lys Tyr Glu Phe
1               5                   10                  15

Ser Val
```

```
<210> SEQ ID NO 91
<211> LENGTH: 21
<212> TYPE: PRT
<213> ORGANISM: Homo sapiens
<220> FEATURE:
<221> NAME/KEY: misc_feature
<222> LOCATION: (1)...(21)
<223> OTHER INFORMATION: Partial aa sequence of human alpha9 integrin

<400> SEQUENCE: 91

Ser Ser Ser Val Ile Gln Phe Met Ser Arg Ala Lys Val Lys Val Asp
1               5                   10                  15

Pro Ala Leu Arg Val
            20

<210> SEQ ID NO 92
<211> LENGTH: 8
<212> TYPE: PRT
<213> ORGANISM: Homo sapiens
<220> FEATURE:
<221> NAME/KEY: misc_feature
<222> LOCATION: (1)...(8)
<223> OTHER INFORMATION: alpha9 integrin binding site of Tenascin-C

<400> SEQUENCE: 92

Ala Glu Ile Asp Gly Ile Glu Leu
1               5

<210> SEQ ID NO 93
<211> LENGTH: 11
<212> TYPE: PRT
<213> ORGANISM: Homo sapiens
<220> FEATURE:
<221> NAME/KEY: misc_feature
<222> LOCATION: (1)...(11)
<223> OTHER INFORMATION: alpha9 integrin binding site of human
      fibronectin

<400> SEQUENCE: 93

Cys Pro Glu Asp Gly Ile His Glu Leu Phe Pro
1               5                   10

<210> SEQ ID NO 94
<211> LENGTH: 23
<212> TYPE: DNA
<213> ORGANISM: Artificial Sequence
<220> FEATURE:
<223> OTHER INFORMATION: synthetically constructed GeneRacer primer

<400> SEQUENCE: 94
cgactggagc acgaggacac tga                                           23

<210> SEQ ID NO 95
<211> LENGTH: 20
<212> TYPE: DNA
<213> ORGANISM: Artificial Sequence
<220> FEATURE:
<223> OTHER INFORMATION: synthetically constructed VH primer

<400> SEQUENCE: 95
gccagtggat agacagatgg                                               20

<210> SEQ ID NO 96
<211> LENGTH: 21
<212> TYPE: DNA
<213> ORGANISM: Artificial Sequence
<220> FEATURE:
<223> OTHER INFORMATION: synthetically constructed VL primer
```

<400> SEQUENCE: 96
gatggataca gttggtgcag c                                              21

<210> SEQ ID NO 97
<211> LENGTH: 39
<212> TYPE: DNA
<213> ORGANISM: Artificial Sequence
<220> FEATURE:
<223> OTHER INFORMATION: synthetically constructed VH primer
<220> FEATURE:
<221> NAME/KEY: misc_feature
<222> LOCATION: (4)...(9)
<223> OTHER INFORMATION: SpeI site

<400> SEQUENCE: 97
gggactagta ccaccatgaa atgcagctgg gttatcttc                           39

<210> SEQ ID NO 98
<211> LENGTH: 49
<212> TYPE: DNA
<213> ORGANISM: Artificial Sequence
<220> FEATURE:
<223> OTHER INFORMATION: synthetically constructed VH primer
<220> FEATURE:
<221> NAME/KEY: misc_feature
<222> LOCATION: (4)...(9)
<223> OTHER INFORMATION: HindIII site

<400> SEQUENCE: 98
gggaagctta gaggccattc ttacctgagg agacggtgac tgaggttcc                49

<210> SEQ ID NO 99
<211> LENGTH: 39
<212> TYPE: DNA
<213> ORGANISM: Artificial Sequence
<220> FEATURE:
<223> OTHER INFORMATION: synthetically constructed VL primer
<220> FEATURE:
<221> NAME/KEY: misc_feature
<222> LOCATION: (4)...(9)
<223> OTHER INFORMATION: NheI site

<400> SEQUENCE: 99
ggggctagca ccaccatgag tgtgcccact caactcctg                           39

<210> SEQ ID NO 100
<211> LENGTH: 50
<212> TYPE: DNA
<213> ORGANISM: Artificial Sequence
<220> FEATURE:
<223> OTHER INFORMATION: synthetically constructed VL primer
<220> FEATURE:
<221> NAME/KEY: misc_feature
<222> LOCATION: (4)...(9)
<223> OTHER INFORMATION: EcoRI site

<400> SEQUENCE: 100
ggggaattct gagaagacta cttacgtttt atttccagct tggtcccccc               50

<210> SEQ ID NO 101
<211> LENGTH: 27
<212> TYPE: DNA
<213> ORGANISM: Artificial Sequence
<220> FEATURE:
<223> OTHER INFORMATION: synthetically constructed JNJ120 primer

<400> SEQUENCE: 101

```
gggactagta ccaccatgaa atgcagc                                              27

<210> SEQ ID NO 102
<211> LENGTH: 57
<212> TYPE: DNA
<213> ORGANISM: Artificial Sequence
<220> FEATURE:
<223> OTHER INFORMATION: synthetically constructed JNJ137 primer

<400> SEQUENCE: 102
gggactagta ccaccatgaa atgcagctgg gttatcttct tcctgatggc agtggtt          57

<210> SEQ ID NO 103
<211> LENGTH: 57
<212> TYPE: DNA
<213> ORGANISM: Artificial Sequence
<220> FEATURE:
<223> OTHER INFORMATION: synthetically constructed JNJ138 primer

<400> SEQUENCE: 103
agactgcacc agctgaacct gtgaattgac ccctgtaacc actgccatca ggaagaa          57

<210> SEQ ID NO 104
<211> LENGTH: 57
<212> TYPE: DNA
<213> ORGANISM: Artificial Sequence
<220> FEATURE:
<223> OTHER INFORMATION: synthetically constructed JNJ139 primer

<400> SEQUENCE: 104
caggttcagc tggtgcagtc tggggcagag gtgaagaagc caggggcctc agtcaag          57

<210> SEQ ID NO 105
<211> LENGTH: 57
<212> TYPE: DNA
<213> ORGANISM: Artificial Sequence
<220> FEATURE:
<223> OTHER INFORMATION: synthetically constructed JNJ140 primer

<400> SEQUENCE: 105
gtctttaatg ttgaagccag aagccttgca ggaaaccttg actgaggccc ctggctt          57

<210> SEQ ID NO 106
<211> LENGTH: 60
<212> TYPE: DNA
<213> ORGANISM: Artificial Sequence
<220> FEATURE:
<223> OTHER INFORMATION: synthetically constructed JNJ141 primer

<400> SEQUENCE: 106
tctggcttca acattaaaga cacctatgtg cactgggtgc gccaggcccc tggacagagg      60

<210> SEQ ID NO 107
<211> LENGTH: 57
<212> TYPE: DNA
<213> ORGANISM: Artificial Sequence
<220> FEATURE:
<223> OTHER INFORMATION: synthetically constructed JNJ142 primer

<400> SEQUENCE: 107
accattcgca ggatcaatat ttccaatcca ctccagcctc tgtccagggg cctggcg          57

<210> SEQ ID NO 108
<211> LENGTH: 60
<212> TYPE: DNA
<213> ORGANISM: Artificial Sequence
```

```
<220> FEATURE:
<223> OTHER INFORMATION: synthetically constructed JNJ143 primer

<400> SEQUENCE: 108
aatattgatc ctgcgaatgg taatactaaa tatgacccga agttccaggg caaggccact     60

<210> SEQ ID NO 109
<211> LENGTH: 57
<212> TYPE: DNA
<213> ORGANISM: Artificial Sequence
<220> FEATURE:
<223> OTHER INFORMATION: synthetically constructed JNJ144 primer

<400> SEQUENCE: 109
catgtaggct gtgctcgcgg atgtgtctgc tgttatagtg gccttgccct ggaactt       57

<210> SEQ ID NO 110
<211> LENGTH: 57
<212> TYPE: DNA
<213> ORGANISM: Artificial Sequence
<220> FEATURE:
<223> OTHER INFORMATION: synthetically constructed JNJ145 primer

<400> SEQUENCE: 110
tccgcgagca cagcctacat ggagctcagc agcctgagat ctgaggacac tgccgtc       57

<210> SEQ ID NO 111
<211> LENGTH: 54
<212> TYPE: DNA
<213> ORGANISM: Artificial Sequence
<220> FEATURE:
<223> OTHER INFORMATION: synthetically constructed JNJ146 primer

<400> SEQUENCE: 111
atagtaaaaa tgtcgtaacc atctagcaca gtaatagacg gcagtgtcct caga          54

<210> SEQ ID NO 112
<211> LENGTH: 57
<212> TYPE: DNA
<213> ORGANISM: Artificial Sequence
<220> FEATURE:
<223> OTHER INFORMATION: synthetically constructed JNJ147 primer

<400> SEQUENCE: 112
tggttacgac attttactat gctatggac tactggggtc aaggaaccct ggtcacc        57

<210> SEQ ID NO 113
<211> LENGTH: 54
<212> TYPE: DNA
<213> ORGANISM: Artificial Sequence
<220> FEATURE:
<223> OTHER INFORMATION: synthetically constructed JNJ148 primer

<400> SEQUENCE: 113
gggaagcttt tgtgaggact cacctgagga gacggtgacc agggttcctt gacc          54

<210> SEQ ID NO 114
<211> LENGTH: 21
<212> TYPE: DNA
<213> ORGANISM: Artificial Sequence
<220> FEATURE:
<223> OTHER INFORMATION: synthetically constructed JNJ149 primer

<400> SEQUENCE: 114
gggaagcttt tgtgaggact c                                              21
```

<210> SEQ ID NO 115
<211> LENGTH: 21
<212> TYPE: DNA
<213> ORGANISM: Artificial Sequence
<220> FEATURE:
<223> OTHER INFORMATION: synthetically constructed JNJ150 primer

<400> SEQUENCE: 115
ggggctagca ccaccatgag t                                       21

<210> SEQ ID NO 116
<211> LENGTH: 57
<212> TYPE: DNA
<213> ORGANISM: Artificial Sequence
<220> FEATURE:
<223> OTHER INFORMATION: synthetically constructed JNJ126 primer

<400> SEQUENCE: 116
ggggctagca ccaccatgag tgtgcccact caactcctgg ggttgctgct gctgtgg       57

<210> SEQ ID NO 117
<211> LENGTH: 60
<212> TYPE: DNA
<213> ORGANISM: Artificial Sequence
<220> FEATURE:
<223> OTHER INFORMATION: synthetically constructed JNJ127 primer

<400> SEQUENCE: 117
agactgagtc atctggatgt cacatcgtgc gtctgtaagc cacagcagca gcaaccccag    60

<210> SEQ ID NO 118
<211> LENGTH: 54
<212> TYPE: DNA
<213> ORGANISM: Artificial Sequence
<220> FEATURE:
<223> OTHER INFORMATION: synthetically constructed JNJ128 primer

<400> SEQUENCE: 118
gacatccaga tgactcagtc tccatcctcc ctgtctgcat ctgtgggaga caga          54

<210> SEQ ID NO 119
<211> LENGTH: 57
<212> TYPE: DNA
<213> ORGANISM: Artificial Sequence
<220> FEATURE:
<223> OTHER INFORMATION: synthetically constructed JNJ129 primer

<400> SEQUENCE: 119
gtaaatgttc tcacttgctc gacatgtgat ggtgactctg tctcccacag atgcaga       57

<210> SEQ ID NO 120
<211> LENGTH: 57
<212> TYPE: DNA
<213> ORGANISM: Artificial Sequence
<220> FEATURE:
<223> OTHER INFORMATION: synthetically constructed JNJ130 primer

<400> SEQUENCE: 120
cgagcaagtg agaacattta ctacagttta gcatggtatc agcagaagcc agggaaa       57

<210> SEQ ID NO 121
<211> LENGTH: 57
<212> TYPE: DNA
<213> ORGANISM: Artificial Sequence
<220> FEATURE:
<223> OTHER INFORMATION: synthetically constructed JNJ131 primer

<400> SEQUENCE: 121
caagctgttt gcattataga tcaggagctt aggggctttc cctggcttct gctgata 57

<210> SEQ ID NO 122
<211> LENGTH: 57
<212> TYPE: DNA
<213> ORGANISM: Artificial Sequence
<220> FEATURE:
<223> OTHER INFORMATION: synthetically constructed JNJ132 primer

<400> SEQUENCE: 122
atctataatg caaacagctt ggaagatggt gtcccatcga ggttcagtgg cagtgga 57

<210> SEQ ID NO 123
<211> LENGTH: 57
<212> TYPE: DNA
<213> ORGANISM: Artificial Sequence
<220> FEATURE:
<223> OTHER INFORMATION: synthetically constructed JNJ133 primer

<400> SEQUENCE: 123
caggctgctg atggtgagag tatactgtgt cccagatcca ctgccactga acctcga 57

<210> SEQ ID NO 124
<211> LENGTH: 57
<212> TYPE: DNA
<213> ORGANISM: Artificial Sequence
<220> FEATURE:
<223> OTHER INFORMATION: synthetically constructed JNJ134 primer

<400> SEQUENCE: 124
actctcacca tcagcagcct gcagcctgaa gattttgcaa cttattactg taaacag 57

<210> SEQ ID NO 125
<211> LENGTH: 57
<212> TYPE: DNA
<213> ORGANISM: Artificial Sequence
<220> FEATURE:
<223> OTHER INFORMATION: synthetically constructed JNJ135 primer

<400> SEQUENCE: 125
ggtcccttgt ccgaacgtgt acggaacgtc ataagcctgt ttacagtaat aagttgc 57

<210> SEQ ID NO 126
<211> LENGTH: 45
<212> TYPE: DNA
<213> ORGANISM: Artificial Sequence
<220> FEATURE:
<223> OTHER INFORMATION: synthetically constructed JNJ136 primer

<400> SEQUENCE: 126
tacacgttcg gacaagggac caaggtggaa atcaaacgtg agtag 45

<210> SEQ ID NO 127
<211> LENGTH: 37
<212> TYPE: DNA
<213> ORGANISM: Artificial Sequence
<220> FEATURE:
<223> OTHER INFORMATION: synthetically constructed JNJ101 primer

<400> SEQUENCE: 127
ggggaattct ttaaattcta ctcacgtttg atttcca 37

<210> SEQ ID NO 128

```
<211> LENGTH: 20
<212> TYPE: DNA
<213> ORGANISM: Artificial Sequence
<220> FEATURE:
<223> OTHER INFORMATION: synthetically constructed JNJ117 primer

<400> SEQUENCE: 128
ggggaattct ttaaattcta                                               20

<210> SEQ ID NO 129
<211> LENGTH: 20
<212> TYPE: DNA
<213> ORGANISM: Artificial Sequence
<220> FEATURE:
<223> OTHER INFORMATION: synthetically constructed primer for mouse
      gamma1, gamma2a, gamma2b and gamma3 H-chains

<400> SEQUENCE: 129
gccagtggat agactgatgg                                               20

<210> SEQ ID NO 130
<211> LENGTH: 21
<212> TYPE: DNA
<213> ORGANISM: Artificial sequence
<220> FEATURE:
<223> OTHER INFORMATION: synthetically constructed primer for mouse
      kappa L-chain

<400> SEQUENCE: 130
gatggataca gttggtgcag c                                             21
```